United States Patent
Furukawa

(12) 
(10) Patent No.: US 6,333,413 B1
(45) Date of Patent: Dec. 25, 2001

(54) PRODUCTION OF PYRIDAZINE HERBICIDES

(75) Inventor: Takashi Furukawa, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/617,797

(22) Filed: Jul. 17, 2000

Related U.S. Application Data (6262) Division of application No. 09/284,265, filed as application No. PCT/JP97/03726 on Oct. 16, 1997, now Pat. No. 6,156,891.

(30) Foreign Application Priority Data

Oct. 21, 1996 (JP) .................................................. 8-278255
Jun. 4, 1997 (JP) .................................................. 9-146241

(51) Int. Cl.[7] ............ C07D 237/14; C07D 403/10; C07D 405/10; C07D 413/10
(52) U.S. Cl. ............ 544/238; 544/239; 544/52; 544/105
(58) Field of Search .................. 544/239, 238, 544/52, 105

(56) References Cited

U.S. PATENT DOCUMENTS 6,090,753 * 7/2000 Katayama et al. ................. 504/238

FOREIGN PATENT DOCUMENTS

A0143281 6/1985 (EP) .
A9707104 2/1997 (WO) .

OTHER PUBLICATIONS

Schober et al., *J. Heterocycl. Chem.* (JHTCAD,0022152X), 89, vol. 26, pp. 169–176.
Rokhlin, *Chemical Abstracts*, vol. 60, No. 5, Mar. 2, 1964.
Bradbury, *Chemical Abstracts*, vol. 51, No. 4, 1956.

* cited by examiner

Primary Examiner—Mark L Berch
Assistant Examiner—Kahsay Habte

(74) *Attorney, Agent, or Firm*—Birch, Stewart, Kolasch & Birch, LLP.

(57) ABSTRACT

Carboxylic acids of formula (1):

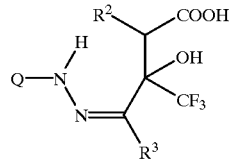

wherein $R^2$ and $R^3$ are independently hydrogen or $C_1$–$C_3$ alkyl, and Q is optionally substituted phenyl, can be easily converted by ring closing into pyridazin-3-one derivatives of formula (7):

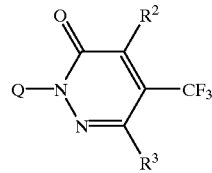

The carboxylic acids of formula (1) can be produced by reacting hydrazone compounds of formula (5):

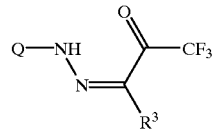

wherein $R^3$ and Q are as defined above, with malonic acid derivatives of formula (6):

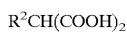

$R^2CH(COOH)_2$ wherein $R^2$ is as defined above, in the presence of a base.

5 Claims, No Drawings

PRODUCTION OF PYRIDAZINE HERBICIDES

This application is a divisional of application Ser. No. 09/284,265, filed on Apr. 9, 1999 U.S. Pat. No. 6,156,891. Application Ser. No. 09/284,265 is the national phase of PCT International Application No. PCT/JP97/03726 filed on Oct. 16, 1997 under 35 U.S.C. §371. The entire contents of each of the above-identified appilcations are hereby incorporated by reference.

TECHNICAL FIELD

The present invention relates to the production of pyridazine herbicides, and more particularly, it relates to carboxylic acids useful as intermediates for the production of pyridazin-3-one derivatives, a process for producing these intermediates, and a process for producing pyridazin-3-one derivatives from these intermediates.

BACKGROUND ART

Pyridazin-3-one derivatives of formula (7):

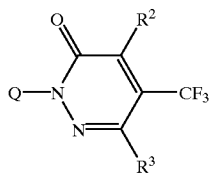

wherein $R^2$ and $R^3$ are independently hydrogen or $C_1$–$C_3$ alkyl, and Q is optionally substituted phenyl, have excellent herbicidal activity, including the following examples:

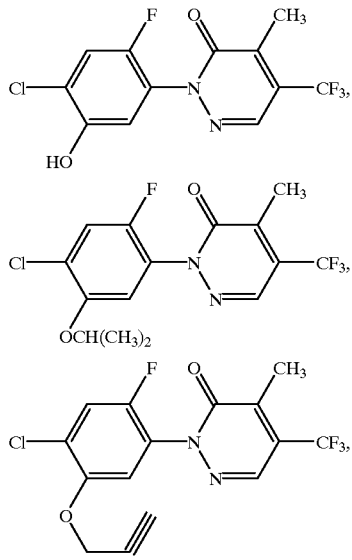

The production of pyridazin-3-one derivatives in a favorable manner is preferred for the development of pyridazine herbicides with excellent activity.

DISCLOSURE OF INVENTION

The present inventors have intensively studied to find a process for producing pyridazin-3-one derivatives in a favorable manner. As a result, they have found that carboxylic acids of formula (1):

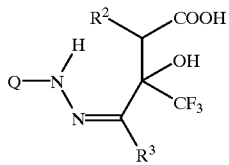

wherein $R^2$, $R^3$ and Q are as defined above, can be easily converted into pyridazin-3-one derivatives of formula (7) and therefore serve as their important intermediates, thereby completing the present invention.

Thus, the present invention provides compounds of formula (1):

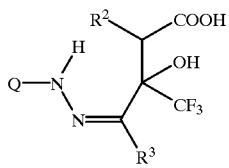

wherein $R^2$, $R^3$ and Q are as defined above, which compounds are hereinafter referred to as the present compound(s), a process for their production, and a process for producing pyridazin-3-one derivatives of formula (7):

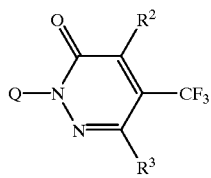

wherein $R^2$, $R^3$ and Q are as defined above, comprising ring closing the compounds of formula (1).

Examples of the optionally substituted phenyl group represented by Q may include, for example, groups Q-1, Q-2, Q-3, Q-4 and Q-5 of formula (2):

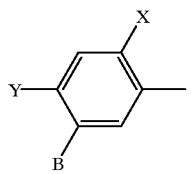

-continued

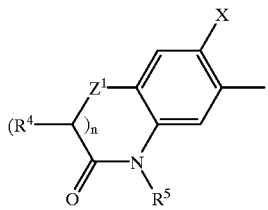

Q-2

Q-3

Q-4

Q-5 wherein X is hydrogen or halogen;
Y is halogen, nitro, cyano or trifluoromethyl;
$Z^1$ and $Z^2$ are independently oxygen or sulfur;
n is 0 or 1;
$R^4$ is hydrogen or $C_1-C_3$ alkyl;
$R^5$ is $C_1-C_6$ alkyl, $C_1-C_6$ haloalkyl, ($C_3-C_6$ cycloalkyl) $C_1-C_6$ alkyl, $C_3-C_6$ alkenyl, $C_3-C_6$ haloalkenyl, $C_3-C_6$ alkynyl, $C_3-C_6$ haloalkynyl, cyano $C_1-C_6$ alkyl, $C_1-C_4$ alkoxy $C_1-C_4$ alkyl, $C_1-C_3$ alkoxy $C_1-C_3$ alkoxy $C_1-C_3$ alkyl, carboxy $C_1-C_6$ alkyl, ($C_1-C_6$ alkoxy)carbonyl $C_1-C_6$ alkyl, {($C_1-C_4$ alkoxy) $C_1-C_4$ alkoxy}carbonyl $C_1-C_6$ alkyl, ($C_3-C_8$ cycloalkoxy)carbonyl $C_1-C_6$ alkyl, —$CH_2CON(R^{12})R^{13}$, —$CH_2COO-N(R^{12})R^{13}$, —$CH(C_1-C_4$ alkyl)$CON(R^{12})R^{13}$, —$CH(C_1-C_4$ alkyl)$COON(R^{12})R^{13}$, $C_1-C_4$ alkylthio $C_1-C_4$ alkyl or hydroxy $C_1-C_6$ alkyl;
$R^{12}$ and $R^{13}$ are independently hydrogen, $C_1-C_6$ alkyl, $C_3-C_8$ cycloalkyl, $C_1-C_6$ haloalkyl, $C_3-C_6$ alkenyl, $C_3-C_6$ alkynyl, cyano $C_1-C_6$ alkyl, $C_1-C_4$ alkoxy $C_1-C_4$ alkyl, $C_1-C_4$ alkylthio $C_1-C_4$ alkyl, carboxy $C_1-C_6$ alkyl, ($C_1-C_6$ alkoxy)carbonyl $C_1-C_6$ alkyl, ($C_3-C_8$ cycloalkoxy)carbonyl $C_1-C_6$ alkyl, ($C_1-C_6$ alkyl)carbonyloxy $C_2-C_6$ alkyl, ($C_1-C_6$ alkyl)carbonylamino $C_2-C_6$ alkyl, hydroxy $C_2-C_6$ alkyl, optionally substituted benzyl, optionally substituted phenyl or {($C_1-C_4$ alkoxy) $C_1-C_4$ alkyl}carbonyl $C_1-C_6$ alkyl, or $R^{12}$ and $R^{13}$ are taken together to form trimethylene, tetramethylene, pentamethylene, ethyleneoxyethylene or ethylenethioethylene;
$R^6$ is $C_1-C_6$ alkyl, $C_1-C_6$ haloalkyl, cyano, carboxyl, hydroxy $C_1-C_6$ alkyl, $C_1-C_6$ alkoxy $C_1-C_6$ alkyl, $C_1-C_6$ alkoxy $C_1-C_6$ alkoxy $C_1-C_6$ alkyl, ($C_1-C_6$ alkyl)carbonyloxy $C_1-C_6$ alkyl, ($C_1-C_6$ haloalkyl)carbonyloxy $C_1-C_6$ alkyl or ($C_1-C_6$ alkoxy)carbonyl;
$R^7$ is hydrogen or $C_1-C_6$ alkyl;
$R^8$ is $C_1-C_6$ alkyl, $C_1-C_6$ haloalkyl, hydroxy $C_1-C_6$ alkyl, $C_1-C_4$ alkoxy $C_1-C_4$ alkyl, $C_1-C_3$ alkoxy $C_1-C_3$ alkoxy $C_1-C_3$ alkyl, ($C_1-C_6$ alkyl)carbonyloxy $C_1-C_6$ alkyl, ($C_1-C_6$ haloalkyl)carbonyl $C_1-C_6$ alkyl, carboxyl, carboxy $C_1-C_6$ alkyl, ($C_1-C_8$ alkoxy)carbonyl, ($C_1-C_6$ haloalkoxy)carbonyl, ($C_3-C_{10}$ cycloalkoxy)carbonyl, ($C_3-C_8$ alkenyloxy)carbonyl, ($C_3-C_8$ alkynyloxy)carbonyl, ($C_1-C_6$ alkyl)aminocarbonyl, di($C_1-C_6$ alkyl)aminocarbonyl, ($C_1-C_6$ alkyl)amninocarbonyloxy $C_1-C_6$ alkyl or di($C_1-C_6$ alkyl)aminocarbonyloxy $C_1-C_6$ alkyl;
B is hydrogen, halogen, nitro, cyano, chlorosulfonyl, $OR^1$, $SR^1$, $SO_2OR^{21}$, $COOR^{22}$, $CR^{23}=CR^{24}COOR^{25}$ or $CH_2CHWCOOR^{25}$;
W is hydrogen, chlorine or bromine;
$R^1$ is hydrogen, $C_1-C_6$ alkyl, $C_1-C_6$ haloalkyl, $C_3-C_8$ cycloalkyl, benzyl, $C_3-C_6$ alkenyl, $C_3-C_6$ haloalkenyl, $C_3-C_6$ alkynyl, $C_3-C_6$ haloalkynyl, cyano $C_1-C_6$ alkyl, $C_1-C_4$ alkoxy $C_1-C_4$ alkyl, $C_1-C_4$ alkylthio $C_1-C_4$ alkyl, carboxy $C_1-C_6$ alkyl, ($C_1-C_8$ alkoxy)carbonyl $C_1-C_6$ alkyl, ($C_1-C_6$ haloalkoxy)carbonyl $C_1-C_6$ alkyl, {($C_1-C_4$ alkoxy) $C_1-C_4$ alkoxy}carbonyl $C_1-C_6$ alkyl, ($C_3-C_8$ cycloalkoxy)carbonyl $C_1-C_6$ alkyl, ($C_3-C_8$ cycloalkyl) $C_1-C_6$ alkoxycarbonyl $C_1-C_6$ alkyl, —$CH_2COON(R^{12})R^{13}$—$CH-(C_1-C_4$ alkyl)$COON(R^{12})R^{13}$, —$CH_2CON(R^{12})R^{13}$, —$CH(C_1-C_4$ alkyl)$CON(R^{12})R^{13}$, $C_2-C_6$ alkenyloxycarbonyl $C_1-C_6$ alkyl, $C_3-C_6$ haloalkenyloxycarbonyl $C_1-C_6$ alkyl, $C_3-C_6$ alkynyloxycarbonyl $C_1-C_6$ alkyl, $C_3-C_6$ haloalkynyloxycarbonyl $C_1-C_6$ alkyl, ($C_1-C_6$ alkylthio)carbonyl $C_1-C_6$ alkyl, ($C_1-C_6$ haloalkylthio)carbonyl $C_1-C_6$ alkyl, ($C_3-C_6$ alkenylthio)carbonyl $C_1-C_6$ alkyl, ($C_3-C_6$ haloalkenylthio)carbonyl $C_1-C_6$ alkyl, ($C_3-C_6$ alkenylthio)carbonyl $C_1-C_6$ alkyl, ($C_3-C_6$ haloalkenylthio)carbonyl $C_1-C_6$ alkyl, ($C_3-C_8$ cycloalkylthio)carbonyl $C_1-C_6$ alkyl, ($C_3-C_8$ cyclohaloalkylthio)carbonyl $C_1-C_6$ alkyl, (($C_3-C_8$ cycloalkyl) $C_1-C_6$ alkylthio)carbonyl $C_1-C_6$ alkyl, di($C_1-C_6$ alkyl)C=NO carbonyl $C_1-C_6$ alkyl, (optionally substituted benzylthio)carbonyl $C_1-C_6$ alkyl, (optionally substituted phenylthio)carbonyl $C_1-C_6$ alkyl, hydroxy $C_2-C_6$ alkoxycarbonyl $C_1-C_6$ alkyl, ($C_1-C_6$ alkyl)carbonyloxy $C_2-C_6$ alkoxycarbonyl $C_1-C_6$ alkyl, ($C_1-C_6$ alkyl)carbonylamino $C_2-C_6$ alkoxycarbonyl $C_1-C_6$ alkyl, {($C_1-C_6$ alkoxy)carbonyl $C_1-C_6$ alkyl}oxycarbonyl $C_1-C_6$ alkyl, hydroxy $C_1-C_6$ alkyl, $C_1-C_6$ alkoxycarbonyl, $C_1-C_6$ haloalkoxycarbonyl, $C_3-C_8$ cycloalkoxycarbonyl, $C_3-C_6$ alkenyloxycarbonyl, benzyloxycarbonyl, $C_1-C_6$ alkylcarbonyl, optionally substituted benzyloxycarbonyl $C_1-C_6$ alkyl, optionally substituted phenoxycarbonyl $C_1-C_6$ alkyl, optionally substituted furyloxycarbonyl $C_1-C_6$ alkyl, optionally substituted furyl $C_1$–$C_6$ alkyloxycarbonyl $C_1$–$C_6$ alkyl, optionally substituted thienyloxycarbonyl $C_1$–$C_6$ alkyl, optionally substituted thienyl $C_1$–$C_6$ alkyloxycarbonyl $C_1$–$C_6$ alkyl, optionally substituted pyrrolyloxycarbonyl $C_1$–$C_6$ alkyl, optionally substituted pyrrolyl $C_1$–$C_6$ alkyloxycarbonyl $C_1$–$C_6$ alkyl, optionally substituted imidazoyloxycarbonyl $C_1$–$C_6$ alkyl, optionally substituted imidazoyl $C_1$–$C_6$ alkyloxycarbonyl $C_1$–$C_6$ alkyl, optionally substituted pyrazoyloxycarbonyl $C_1$–$C_6$ alkyl, optionally substituted pyrazoyl $C_1$–$C_6$ alkyloxycarbonyl $C_1$–$C_6$ alkyl, optionally substituted thiazoyloxycarbonyl $C_1$–$C_6$ alkyl, optionally substituted thiazoyl $C_1$–$C_6$ alkyloxycarbonyl $C_1$–$C_6$ alkyl, optionally substituted oxazoyloxycarbonyl $C_1$–$C_6$ alkyl, optionally substituted oxazoyl $C_1$–$C_6$ alkyloxycarbonyl $C_1$–$C_6$ alkyl, optionally substituted isothiazoyloxycarbonyl $C_1$–$C_6$ alkyl, optionally substituted isothiazoyl $C_1$–$C_6$ alkyloxycarbonyl $C_1$–$C_6$ alkyl, optionally substituted isoxazoyloxycarbonyl $C_1$–$C_6$ alkyl, optionally substituted isoxazoyl $C_1$–$C_6$ alkyloxycarbonyl $C_1$–$C_6$ alkyl, optionally substituted pyridyloxycarbonyl $C_1$–$C_6$ alkyl, optionally substituted pyridyl $C_1$–$C_6$ alkyloxycarbonyl $C_1$–$C_6$ alkyl, optionally substituted pyrazinyloxycarbonyl $C_1$–$C_6$ alkyl, optionally substituted pyrazinyl $C_1$–$C_6$ alkyloxycarbonyl $C_1$–$C_6$ alkyl, optionally substituted pyrimidinyloxycarbonyl $C_1$–$C_6$ alkyl, optionally substituted pyrimidinyl $C_1$–$C_6$ alkyloxycarbonyl $C_1$–$C_6$ alkyl, optionally substituted pyridazinyloxycarbonyl $C_1$–$C_6$ alkyl, optionally substituted pyridazinyl $C_1$–$C_6$ alkyloxycarbonyl $C_1$–$C_6$ alkyl, optionally substituted indolidinyloxycarbonyl $C_1$–$C_6$ alkyl, optionally substituted indolidinyl $C_1$–$C_6$ alkyloxycarbonyl $C_1$–$C_6$ alkyl, optionally substituted indolyloxycarbonyl $C_1$–$C_6$ alkyl, optionally substituted indolyl $C_1$–$C_6$ alkyloxycarbonyl $C_1$–$C_6$ alkyl, optionally substituted indazolyloxycarbonyl $C_1$–$C_6$ alkyl, optionally substituted indazolyl $C_1$–$C_6$ alkyloxycarbonyl $C_1$–$C_6$ alkyl, optionally substituted quinolyloxycarbonyl $C_1$–$C_6$ alkyl, optionally substituted quinolyl $C_1$–$C_6$ alkyloxycarbonyl $C_1$–$C_6$ alkyl, optionally substituted isoquinolyloxycarbonyl $C_1$–$C_6$ alkyl, optionally substituted isoquinolyl $C_1$–$C_6$ alkyloxycarbonyl $C_1$–$C_6$ alkyl, or a group of formula (3):

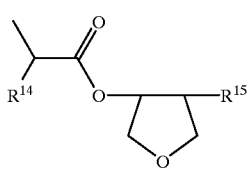

wherein $R^{14}$ is $C_1$–$C_5$ alkyl; $R^{15}$ is hydrogen, hydroxyl or a group of —O—$COR^{16}$; and $R^{16}$ is $C_1$–$C_6$ alkyl, $C_1$–$C_6$ haloalkyl, $C_3$–$C_6$ alkenyl, $C_3$–$C_8$ cycloalkyl, optionally substituted phenyl, optionally substituted benzyl or $C_1$–$C_6$ alkoxy, or a group of formula (4):

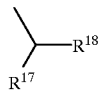

wherein $R^{17}$ is hydrogen, halogen or $C_1$–$C_6$ alkyl; $R^{18}$ is $C_3$–$C_8$ cycloalkyl, benzyl, $C_2$–$C_{10}$ alkyl with an epoxide group, $C_3$–$C_8$ cycloalkyl $C_1$–$C_6$ alkyl, $C_3$–$C_8$ cycloalkyl $C_2$–$C_6$ alkenyl, $C_1$–$C_6$ alkyl substituted with $OR^{19}$ and $OR^{20}$ on the same carbon atom, $C_2$–$C_6$ alkenyl substituted with $OR^{19}$ and $OR^{20}$ on the same carbon atom, $C_1$–$C_6$ alkyl substituted with $SR^{19}$ and $SR^{20}$ on the same carbon atom, $C_2$–$C_6$ alkenyl substituted with $SR^{19}$ and $SR^{20}$ on the same carbon atom, carboxy $C_2$–$C_6$ alkenyl, ($C_1$–$C_8$ alkoxy)carbonyl $C_2$–$C_6$ alkenyl, ($C_1$–$C_8$ haloalkoxy)carbonyl $C_2$–$C_6$ alkenyl, {($C_1$–$C_4$ alkoxy) $C_1$–$C_4$ alkoxy}carbonyl $C_2$–$C_6$ alkenyl or ($C_3$–$C_8$ cycloalkoxy)carbonyl $C_2$–$C_6$ alkenyl; $R^{19}$ and $R^{20}$ are independently $C_1$–$C_6$ alkyl or $C_1$–$C_6$ haloalkyl, or $R^{19}$ and $R^{20}$ are taken together with to form ethylene optionally substituted with halogen, trimethylene optionally substituted with halogen, tetramethylene optionally substituted with halogen, pentamethylene optionally substituted with halogen, or ethyleneoxyethylene optionally substituted with halogen;

$R^{21}$ is $C_1$–$C_6$ alkyl, $C_1$–$C_6$ haloalkyl, $C_3$–$C_8$ cycloalkyl, $C_3$–$C_6$ alkenyl, $C_3$–$C_6$ haloalkenyl, $C_3$–$C_6$ alkynyl, $C_3$–$C_6$ haloalkynyl or benzyl;

$R^{22}$ is hydrogen, $C_1$–$C_6$ alkyl, $C_1$–$C_6$ haloalkyl, $C_3$–$C_8$ cycloalkyl, benzyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_1$–$C_4$ alkoxy $C_1$–$C_4$ alkyl, $C_1$–$C_4$ alkylthio $C_1$–$C_4$ alkyl, carboxy $C_1$–$C_6$ alkyl; ($C_1$–$C_8$ alkoxy)carbonyl $C_1$–$C_6$ alkyl, ($C_1$–$C_6$ haloalkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, ($C_1$–$C_6$ alkyl)carbonyl $C_1$–$C_6$ alkyl, ($C_1$–$C_6$ haloalkyl)carbonyl $C_1$–$C_6$ alkyl, {($C_1$–$C_4$ alkoxy) $C_1$–$C_4$ alkyl}carbonyl $C_1$–$C_6$ alkyl, ($C_3$–$C_8$ cycloalkyl)carbonyl $C_1$–$C_6$ alkyl, —$CH_2COON$($R^{26}$)$R^{27}$, —$CH$($C_1$–$C_4$ alkyl)$COON$($R^{26}$)$R^{27}$, —$CH_2CON$($R^{26}$)$R^{27}$—$CH$—($C_1$–$C_4$ alkyl)$CON$($R^{26}$)$R^{27}$, {($C_1$–$C_6$ alkoxy)carbonyl $C_1$–$C_6$ alkyl}oxycarbonyl $C_1$–$C_6$ alkyl or hydroxy $C_1$–$C_6$ alkyl;

$R^{26}$ and $R^{27}$ are independently hydrogen, $C_1$–$C_6$ alkyl, $C_1$–$C_6$ haloalkyl, $C_3$–$C_6$ alkenyl, $C_3$–$C_6$ alkynyl, cyano $C_1$–$C_6$ alkyl, $C_1$–$C_4$ alkoxy $C_1$–$C_4$ alkyl, $C_1$–$C_4$ alkylthio $C_1$–$C_4$ alkyl, carboxy $C_1$–$C_6$ alkyl, ($C_1$–$C_6$ alkoxy)carbonyl $C_1$–$C_6$ alkyl, ($C_3$–$C_8$ cycloalkoxy)carbonyl $C_1$–$C_6$ alkyl or {($C_1$–$C_4$ alkoxy) $C_1$–$C_4$ alkyl}carbonyl $C_1$–$C_6$ alkyl, or $R^{26}$ and $R^{27}$ are taken together to form tetramethylene, pentamethylene or ethyleneoxyethylene;

$R^{23}$ and $R^{24}$ are independently hydrogen, halogen or $C_1$–$C_6$ alkyl; and $R^{25}$ is hydrogen, $C_1$–$C_6$ alkyl, $C_1$–$C_6$ haloalkyl, $C_3$–$C_8$ cycloalkyl or $C_3$–$C_6$ alkenyl.

In the above definition of the present compounds, the respective substituents are exemplified as follows:

Examples of the halogen represented by X and Y may include fluorine, chlorine, bromine and iodine.

Examples of the $C_1$–$C_3$ alkyl represented by $R^2$ and $R^3$ may include methyl and ethyl.

Examples of the $C_1$–$C_6$ alkyl represented by $R^1$ may include methyl, ethyl, propyl, isopropyl, butyl, isobutyl, t-butyl, amyl, isoamyl and t-amyl, wherein "t-" means "tertiary-" and is hereinafter used in the same meaning.

Examples of the $C_1$–$C_6$ haloalkyl represented by $R^1$ may include 2-chloroethyl, 2-bromoethyl and 2,2,2-trifluoroethyl.

Examples of the $C_3$–$C_8$ cycloalkyl represented by $R^1$ may include cyclopropyl, cyclobutyl, cyclopentyl and cyclohexyl.

Examples of the $C_3$–$C_6$ alkenyl represented by $R^1$ may include allyl, 1-methyl-2-propenyl, 3-butenyl, 2-butenyl, 3-methyl-2-butenyl and 2-methyl-3-butenyl.

Examples of the $C_3$–$C_6$ haloalkenyl represented by $R^1$ may include 2-chloro-2-propenyl and 3,3-dichloro-2-propenyl.

Examples of the $C_3$–$C_6$ alkynyl represented by $R^1$ may include propargyl, 1-methyl-2-propynyl, 2-butynyl and 1,1-dimethyl-2-propynyl.

Examples of the $C_3$–$C_6$ haloalkynyl represented by $R^1$ may include 3-bromopropargyl.

Examples of the cyano $C_1$–$C_6$ alkyl represented by $R^1$ may include cyanomethyl.

Examples of the $C_1$–$C_4$ alkoxy $C_1$–$C_4$ alkyl represented by $R^1$ may include methoxymethyl, methoxyethyl, ethoxymethyl and ethoxyethyl.

Examples of the $C_1$–$C_4$ alkylthio $C_1$–$C_4$ alkyl represented by $R^1$ may include methylthiomethyl and methylthioethyl.

Examples of the carboxy $C_1$–$C_6$ alkyl represented by $R^1$ may include carboxymethyl, 1-carboxyethyl and 2-carboxyethyl.

Examples of the ($C_1$–$C_8$ alkoxy)carbonyl $C_1$–$C_6$ alkyl represented by $R^1$ may include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl and 1-t-amyloxycarbonylethyl.

Examples of the {($C_1$–$C_4$ alkoxy) $C_1$–$C_4$ alkoxy}carbonyl $C_1$–$C_6$ alkyl represented by $R^1$ may include methoxymethoxycarbonylmethyl, methoxyethoxycarbonylmethyl and 1-methoxyethoxycarbonylethyl.

Examples of the ($C_3$–$C_8$ cycloalkoxy)carbonyl $C_1$–$C_6$ alkyl represented by $R^1$ may include cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl and 1-cyclohexyloxycarbonylethyl.

Examples of the $C_1$–$C_6$ alkoxycarbonyl represented by $R^1$ may include methoxycarbonyl, ethoxycarbonyl, propoxycarbonyl, butoxycarbonyl, isopropoxycarbonyl, isobutoxycarbonyl and t-butoxycarbonyl.

Examples of the $C_1$–$C_6$ haloalkoxycarbonyl represented by $R^1$ may include 2,2,2-trichloroethylcarbonyl.

Examples of the $C_3$–$C_8$ cycloalkoxycarbonyl represented by $R^1$ may include cyclopropyloxycarbonyl and cyclobutyloxycarbonyl.

Examples of the $C_3$–$C_6$ alkenyloxycarbonyl represented by $R^1$ may include allyloxycarbonyl.

Examples of the {($C_1$–$C_6$ alkoxy)carbonyl $C_1$–$C_6$ alkyl}oxycarbonyl $C_1$–$C_6$ alkyl represented by $R^1$ may include (methoxycarbonyl)methoxycarbonylmethyl and (ethoxycarbonyl)methoxycarbonylmethyl.

Examples of the $C_1$–$C_6$ alkyl represented by $R^{12}$ and $R^{13}$ may include methyl, ethyl, propyl and isopropyl.

Examples of the $C_1$–$C_3$ alkyl represented by $R^4$ may include methyl.

Examples of the $C_1$–$C_6$ alkyl represented by $R^5$ may include methyl, ethyl, propyl, isopropyl, isobutyl, butyl and isoamyl.

Examples of the $C_1$–$C_6$ haloalkyl represented by $R^5$ may include 2-chloroethyl, 2-bromoethyl, 3-chlorobutyl, 3-bromobutyl and difluoromethyl.

Examples of the ($C_3$–$C_8$ cycloalkyl) $C_1$–$C_6$ alkyl represented by $R^5$ may include cyclopentylmethyl.

Examples of the $C_3$–$C_6$ alkenyl represented by $R^5$ may include allyl, 1-methyl-2-propenyl, 3-butenyl, 2-butenyl, 3-methyl-2-butenyl and 2-methyl-3-butenyl.

Examples of the $C_3$–$C_6$ haloalkenyl represented by $R^5$ may include 2-chloro-2-propenyl and 3,3-dichloro-2-propenyl.

Examples of the $C_3$–$C_6$ alkynyl represented by $R^5$ may include propargyl, 1-methyl-2-propynyl, 2-butynyl, 3-butynyl and 1,1-dimethyl-2-propynyl.

Examples of the $C_3$–$C_6$ haloalkenyl represented by $R^5$ may include 3-iodo-2-propynyl and 3-bromo-2-propynyl.

Examples of the cyano $C_1$–$C_6$ alkyl represented by $R^5$ may include cyano-methyl.

Examples of the $C_1$–$C_4$ alkoxy $C_1$–$C_4$ alkyl represented by $R^5$ may include methoxymethyl, 1-methoxyethyl and ethoxymethyl.

Examples of the carboxy $C_1$–$C_6$ alkyl represented by $R^5$ may include carboxy-methyl, 1-carboxyethyl and 2-carboxyethyl.

Examples of the ($C_1$–$C_6$ alkoxy)carbonyl $C_1$–$C_6$ alkyl represented by $R^5$ may include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl and 1-t-butoxycarbonylethyl.

Examples of the {($C_1$–$C_4$ alkoxy) $C_1$–$C_4$ alkoxy} carbonyl $C_1$–$C_6$ alkyl represented by $R^5$ may include methoxyethoxycarbonylmethyl and 1-methoxymethoxycarbonylethyl.

Examples of the ($C_3$–$C_8$ cycloalkoxy)carbonyl $C_1$–$C_6$ alkyl represented by $R^5$ may include cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl and 1-cyclohexyloxycarbonylethyl.

Examples of the hydroxy $C_1$–$C_6$ alkyl represented by $R^5$ may include hydroxymethyl, hydroxyethyl and hydroxypropyl.

Examples of the $C_1$–$C_6$ alkyl represented by $R^6$ may include methyl and ethyl.

Examples of the $C_1$–$C_6$ haloalkyl represented by $R^6$ may include bromomethyl, dibromomethyl, tribromomethyl, 1-bromoethyl, chloromethyl, dichloromethyl and trichloromethyl.

Examples of the hydroxy $C_1$–$C_6$ alkyl represented by $R^6$ may include hydroxymethyl.

Examples of the ($C_1$–$C_6$ alkoxy) $C_1$–$C_6$ alkyl represented by $R^6$ may include methoxymethyl, ethoxymethyl, propoxymethyl and isopropoxymethyl.

Examples of the {($C_1$–$C_6$ alkoxy) $C_1$–$C_6$ alkoxy} $C_1$–$C_6$ alkyl represented by $R^6$ may include methoxymethoxymethyl, methoxyethoxymethyl and ethoxymethoxymethyl.

Examples of the ($C_1$–$C_6$ alkyl)carbonyloxy $C_1$–$C_6$ alkyl) represented by $R^6$ may include acetyloxymethyl, ethylcarbonyloxymethyl and isopropylcarbonyloxymethyl.

Examples of the ($C_1$–$C_6$ haloalkyl)carbonyloxy $C_1$–$C_6$ alkyl represented by $R^6$ may include trifluoroacetyloxymethyl, chloroacetyloxymethyl and trichloroacetyloxymethyl.

Examples of the ($C_1$–$C_6$ alkoxy)carbonyl represented by $R^6$ may include methoxycarbonyl, ethoxycarbonyl, propoxycarbonyl, butoxycarbonyl, amyloxycarbonyl, isopropoxycarbonyl, isobutoxycarbonyl and isoamyloxycarbonyl.

Examples of the $C_1$–$C_6$ alkyl represented by $R^7$ may include methyl.

Examples of the $C_1$–$C_6$ alkyl represented by $R^8$ may include methyl and ethyl.

Examples of the $C_1$–$C_6$ haloalkyl represented by $R^8$ may include chloromethyl and bromomethyl.

Examples of the $C_1$–$C_6$ hydroxyalkyl represented by $R^8$ may include hydroxymethyl.

Examples of the $C_1$–$C_4$ alkoxy $C_1$–$C_4$ alkyl represented by $R^8$ may include methoxymethyl, ethoxymethyl, isopropoxymethyl, butoxymethyl and isobutoxymethyl.

Examples of the $C_1$–$C_3$ alkoxy $C_1$–$C_3$ alkoxy $C_1$–$C_3$ alkyl represented by $R^8$ may include methoxymethoxymethyl, methoxyethoxymethyl and ethoxymethoxymethyl.

Examples of the ($C_1$–$C_6$ alkyl)carbonyloxy $C_1$–$C_6$ alkyl represented by $R^8$ may include acetyloxymethyl, ethylcarbonyloxymethyl and isopropylcarbonyloxymethyl.

Examples of the ($C_1$–$C_6$ haloalkyl)carbonyl $C_1$–$C_6$ alkyl represented by $R^8$ may include 2-chloroethylcarbonyloxymethyl.

Examples of the carboxy $C_1$–$C_6$ alkyl represented by $R^8$ may include carboxymethyl.

Examples of the ($C_1$–$C_8$ alkoxy)carbonyl represented by $R^8$ may include methoxycarbonyl, ethoxycarbonyl, propoxycarbonyl, butoxycarbonyl, amyloxycarbonyl, isopropoxycarbonyl, isobutoxycarbonyl and isoamyloxycarbonyl.

Examples of the ($C_1$–$C_6$ haloalkoxy)carbonyl represented by $R^8$ may include 2-chloroethoxycarbonyl, 2-bromoethoxycarbonyl, 3-chlorobutoxycarbonyl, 1-chloro-2-propoxycarbonyl, 1,3-dichloro-2-propoxycarbonyl, 2,2-dicholoroethoxycarbonyl, 2,2,2-trifluoroethoxycarbonyl, 2,2,2-trichloroethoxycarbonyl and 2,2,2-tribromoethoxycarbonyl.

Examples of the ($C_3$–$C_{10}$ cycloalkoxy)carbonyl represented by $R^8$ may include cyclobutyloxycarbonyl, cyclopentyloxycarbonyl and cyclohexyloxycarbonyl.

Examples of the ($C_3$–$C_8$ alkenyloxy)carbonyl represented by $R^8$ may include allyloxycarbonyl, 3-butenyloxycarbonyl and 1-methyl-2-propenyloxycarbonyl.

Examples of the ($C_3$–$C_8$ alkynyloxy)carbonyl represented by $R^8$ may include propargyloxycarbonyl, 3-butynyloxycarbonyl and 1-methyl-2-propynyloxycarbonyl.

Examples of the ($C_1$–$C_6$ alkyl)aminocarbonyl represented by $R^8$ may include methylaminocarbonyl, ethylaminocarbonyl and propylaminocarbonyl.

Examples of the di($C_1$–$C_6$ alkyl)aminocarbonyl represented by $R^8$ may include dimethylaminocarbonyl, diethylaminocarbonyl and diisopropylaminocarbonyl.

Examples of the ($C_1$–$C_6$ alkyl)aminocarbonyloxy $C_1$–$C_6$ alkyl represented by $R^8$ may include methylaminocarbonyloxymethyl, ethylaminocarbonyloxymethyl and propylaminocarbonyloxymethyl.

Examples of the di($C_1$–$C_6$ alkyl)aminocarbonyloxy $C_1$–$C_6$ alkyl represented by $R^8$ may include dimethylaminocarbonyloxymethyl and dimethylaminocarbonyloxymethyl.

Examples of the $C_1$–$C_6$ alkyl represented by $R^{22}$ may include methyl, ethyl, propyl, isopropyl, isobutyl, butyl, t-butyl, amyl, isoamyl and t-amyl.

Examples of the $C_1$–$C_6$ haloalkyl represented by $R^{22}$ may include 2-chloroethyl, 2-bromoethyl and 2,2,2-trifluoroethyl.

Examples of the $C_3$–$C_8$ cycloalkyl represented by $R^{22}$ may include cyclopropyl, cyclobutyl, cyclopentyl and cyclohexyl.

Examples of the $C_3$–$C_6$ alkenyl represented by $R^{22}$ may include allyl, 1-methyl-2-propenyl, 3-butenyl, 2-butenyl, 3-methyl-2-butenyl and 2-methyl-3-butenyl.

Examples of the $C_3$–$C_6$ haloalkenyl represented by $R^{22}$ may include 2-chloro-2-propenyl and 3,3-dichloro-2-propenyl.

Examples of the $C_3$–$C_6$ alkynyl represented by $R^{22}$ may include propargyl, 1-methyl-2-propynyl and 2-butynyl.

Examples of the $C_3$–$C_6$ haloalkenyl represented by $R^{22}$ may include 3-bromo-propargyl.

Examples of the cyano $C_1$–$C_6$ alkyl represented by $R^{22}$ may include cyano-ethyl.

Examples of the $C_1$–$C_4$ alkoxy $C_1$–$C_4$ alkyl represented by $R^{22}$ may include methoxymethyl, methoxyethyl, ethoxymethyl and ethoxyethyl.

Examples of the $C_1$–$C_4$ alkylthio $C_1$–$C_4$ alkyl represented by $R^{22}$ may include methylthioethyl.

Examples of the carboxy $C_1$–$C_6$ alkyl represented by $R^{22}$ may include carboxymethyl, 1-carboxyethyl and 2-carboxyethyl.

Examples of the ($C_1$–$C_8$ alkoxy)carbonyl $C_1$–$C_6$ alkyl represented by $R^{22}$ may include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl and 1-t-amyloxycarbonylethyl.

Examples of the {($C_1$–$C_4$ alkoxy) $C_1$–$C_4$ alkoxy}carbonyl $C_1$–$C_6$ alkyl represented by $R^{22}$ may include methoxymethoxycarbonylmethyl, methoxyethoxycarbonylmethyl and 1-methoxyethoxycarbonylethyl.

Examples of the ($C_3$–$C_8$ cycloalkoxy)carbonyl $C_1$–$C_6$ alkyl represented by $R^{22}$ may include cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl and 1-cyclohexyloxycarbonylethyl.

Examples of the $C_1$–$C_6$ alkyl represented by $R^{23}$ and $R^{24}$ may include methyl.

Examples of the halogen represented by $R^{23}$ and $R^{24}$ may include chlorine and bromine.

Examples of the $C_1-C_6$ alkyl represented by $R^{25}$ may include methyl, ethyl, propyl, isopropyl, isobutyl, butyl, t-butyl, amyl, isoamyl and t-amyl.

Examples of the $C_1-C_6$ haloalkyl represented by $R^{25}$ may include 2-chloroethyl, 2-bromoethyl and 2,2,2-trifluoroethyl.

Examples of the $C_3-C_8$ cycloalkyl represented by $R^{25}$ may include cyclopropyl, cyclobutyl, cyclopentyl and cyclohexyl.

Examples of the $C_3-C_6$ alkenyl represented by $R^{25}$ may include allyl, 1-methyl-2-propenyl, 3-butenyl, 2-butenyl, 3-methyl-2-butenyl and 2-methyl-3-butenyl.

Examples of the $C_1-C_6$ alkyl represented by $R^{26}$ and $R^{27}$ may include methyl, ethyl, propyl and isopropyl.

The present compounds have geometrical isomers based on the double bond, optical isomers and diastereomers based on the presence of at least one asymmetric carbon atom, and these isomers and mixtures thereof are, of course, included within the scope of the present invention.

The present compounds are useful for the production of pyridazin-3-one derivatives of formula (7) as described above, and the salts of the present compounds are also used for the production of pyridazin-3-one derivatives of formula (7). Examples of the salt may include alkali metal salts such as lithium, sodium and potassium salts; alkaline earth metal salts such as magnesium and calcium salts; and amine salts such as methylamine, dimethylamine, trimethylamine, ethylamine, diethylamine, triethylamine, diisopropylethylamine, tri-n-propylamine, tri-n-butylamine, pyridine, 4-dimethylamino-pyridine, N,N-dimethylaniline and N,N-diethylaniline salts.

The following illustrates the process for producing the present compounds.

The present compounds can be produced by reacting hydrazone compounds of formula (5):

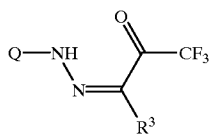

wherein $R^3$ and Q are as defined above, with malonic acid derivatives of formula (6):

wherein $R^2$ is as defined above, in the presence of a base, which process is hereinafter referred to as process 1.

Process 1 can be carried out under the reaction conditions described in the following process 1-1 or 1-2.

Process 1-1 in which the hydrazone compounds of formula (5) are reacted with the malonic acid derivatives of formula (6) in the presence of a secondary amine combined with pyridine and/or quinoline.

The reaction is usually effected in pyridine and/or quinoline. The reaction temperature is usually in the range of 40° to 140° C., preferably 60° to 100° C. The reaction time is usually in the range of a moment to 24 hours.

The amounts of reagents to be used in the reaction are usually 1 to 10 moles of the malonic acid derivative of formula (6) and usually 0.1 to 5 moles, preferably 0.8 to 2 moles, and more preferably 1 to 2 moles of the secondary amine, for each one mole of the hydrazone compound of formula (5).

Examples of the secondary amine used in the reaction may include cyclic amines such as piperidine, morpholine and pyrrolidine; and dialkylamines such as diethylamine and diisopropylamine.

Furthermore, co-solvents can also be used in the reaction, examples of which may include aliphatic hydrocarbons such as hexane, heptane, ligroin and petroleum ether; aromatic hydrocarbons such as benzene, toluene and xylene; halogenated hydrocarbons such as dichloromethane, chloroform, carbon tetrachloride, 1,2-dichloroethane, 1,1,1-trichloroethane, chlorobenzene, dichlorobenzene and benzotrifluoride; ethers such as diethyl ether, diisopropyl ether, 1,4-dioxane, tetrahydrofuran, ethylene glycol dimethyl ether and methyl t-butyl ether; nitriles such as acetonitrile and isobutyronitrile; esters such as ethyl acetate and butyl acetate; alcohols such as methanol, ethanol, propanol, butanol and isopropanol; acid amides such as N,N-dimethylformamide; sulfur compounds such as dimethylsulfoxide and sulforane; and mixtures thereof.

Process 1-2 in which the hydrazone compounds of formula (5) are reacted with the malonic acid derivatives of formula (6) in the presence of a base.

The reaction is usually effected without solvent or in a solvent. The reaction temperature is usually in the range of 20° to 200° C., preferably 40° to 150° C. The reaction time is usually in the range of a moment to 72 hours.

The amounts of reagents to be used in the reaction are usually 1 to 10 moles, preferably 1 to 2 moles, of the malonic acid derivative of formula (6) for each one mole of the hydrazone compound of formula (5), and usually 1 mole to a larger excess, preferably 1 to 10 moles, of the base for each one mole of the malonic acid derivative of formula (6).

Examples of the base used in the reaction may include organic bases, preferably tertiary amines such as dialkylaniline derivatives, e.g., N,N-dimethylaniline and N,N-diethylaniline; triethylamine, diisopropylethylamine, tri-n-propylamine, tri-n-butylamine, benzyldimethylamine, phenethyldimethylamine, N-methylmorpholine, 1,8-diazabicyclo[5,4,0]undec-7-ene, 1,5-diazabicyclo[4,3,0]non-5-ene and 1,4-diazabicyclo[2.2.2]-octane. Preferred are trialkylamines such as triethylamine, diisopropylethylamine, tri-n-propylamine and tri-n-butylamine.

Examples of the solvent used in the reaction may include aliphatic hydrocarbons such as hexane, heptane, ligroin and petroleum ether; aromatic hydrocarbons such as benzene, toluene and xylene; halogenated hydrocarbons such as dichloromethane, chloroform, carbon tetrachloride, 1,2-dichloroethane, 1,1,1-trichloroethane, chlorobenzene, dichlorobenzene and benzotrifluoride; ethers such as diethyl ether, diisopropyl ether, 1,4-dioxane, tetrahydrofuran, ethylene glycol dimethyl ether and methyl t-butyl ether; nitrogen-containing aromatic compounds such as pyridine and quinoline; acid amides such as N,N-dimethylformamide; esters such as ethyl acetate and butyl acetate; ketones such as acetone, methyl ethyl ketone, methyl isobutyl ketone and cyclohexanone; nitriles such as acetonitrile and isobutyronitrile; alcohols such as methanol, ethanol, propanol, butanol and isopropanol; water; and mixtures thereof.

After completion of the reaction in process 1-1 or 1-2, the reaction mixture is subjected to post-treatment that (1) the reaction mixture is directly concentrated, or (2) the reaction mixture is poured into an aqueous solution of a mineral acid such as hydrochloric acid or diluted sulfuric acid, which is then extracted with an organic solvent under acidic conditions, and the organic layer is dried and concentrated, or (3) the reaction mixture is poured into an aqueous solution of a base such as lithium hydroxide, sodium hydroxide, potassium hydroxide, magnesium hydroxide, calcium hydroxide, sodium carbonate or potassium carbonate, from which the organic layer is removed under alkaline conditions, and the water layer is made acidic by the addition of an aqueous solution of a mineral acid such as hydrochloric acid or diluted sulfuric acid, which is then extracted with an organic solvent, and the organic layer is dried and concentrated. If necessary, purification is subsequently carried out by a technique such as recrystallization or column chromatography. Thus, the present compounds can be obtained.

The present compounds can also be purified by the following procedures: According to the process described below, they are converted into salts, which are then dissolved in water. The aqueous solution is extracted with an organic solvent, so that water-insoluble impurities are dissolved in the organic layer, followed by removal of the organic layer. The water layer is made acidic by the addition of an aqueous solution of a mineral acid such as hydrochloric acid or diluted sulfuric acid, which is then extracted with an organic solvent. The organic layer is dried and concentrated.

The following illustrates the process for producing salts of the present compounds.

The salts of the present compounds can be produced by reacting the present compounds with a base.

Examples of the base used in the reaction include, for example, inorganic bases such as lithium hydroxide, sodium hydroxide, potassium hydroxide, magnesium hydroxide, calcium hydroxide, sodium carbonate and potassium carbonate; and organic amines such as alkylamines, e.g., methylamine, dimethylamine, trimethylamine, ethylamine, diethylamine, triethylamine, diisopropylethylamine, tri-n-propylamine and tri-n-butylamine; optionally substituted pyridine compounds, e.g., pyridine and 4-dimethylaminopyridine; and dialkylaniline derivatives, e.g., N,N-dimethylaniline and N,N-diethylaniline.

The reaction is effected, for example, by the following procedures:

(1) The present compounds are added to an aqueous solution of an inorganic base, and the reaction mixture is extracted with an organic solvent, followed by removal of the organic layer. The water layer is concentrated to give the desired salts. In this case, one equivalent of the inorganic base is preferably used for each one equivalent of the present compound.

(2) The present compounds are reacted with an organic base in an organic solvent, and the reaction mixture is concentrated.

The salts of the present compounds obtained by these procedures can be purified, if necessary, by recrystallization or other techniques.

The present compounds are usually obtained as a mixture of diastereomers. These diastereomers can be used as the starting material compounds in the subsequent reaction without particular separation or after fine separation by chromatography.

The malonic acid derivatives of formula (6) used in the above production process are commercially available or can be produced by the known methods.

The hydrazone compounds of formula (5) can be produced by reacting compounds of formula (8):

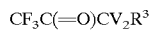

wherein $R^3$ is as defined above and V is iodine, bromine or chlorine, with water in the presence of a base to give carbonyl compounds of formula (9):

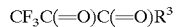

wherein $R^3$ is as defined above, or hydrates or acetal derivatives thereof, which reaction is hereinafter referred to as reaction 1; and then reacting the carbonyl compounds of formula (9), or hydrates or acetal derivatives thereof, with hydrazine derivatives of formula (10):

wherein Q is as defined above, which reaction is hereinafter referred to as reaction 2.

Reaction 1 is usually effected in a solvent. The reaction temperature is usually in the range of 0° to 100° C. The reaction time is usually in the range of a moment to 72 hours.

The amounts of reagents to be used in the reaction are usually 2 moles of water and usually 2 moles of the base for each one mole of the compound of formula (8), which is the stoichiometric ratio. If necessary, these reagents can be used in excess.

As the base, either organic bases or inorganic bases can be used, examples of which may include sodium acetate and potassium acetate.

The carbonyl compounds of formula (9) can also be reacted in the form of hydrates or acetal derivatives in the presence of water or an alcohol.

Reaction 2 is usually effected in a solvent. The reaction temperature is usually in the range of 0° to 100° C. The reaction time is usually in the range of a moment to 72 hours.

The amount of reagent to be used in the reaction is usually 1 mole of the hydrazine derivative of formula (10) for each one mole of the compound of formula (8), which is the stoichiometric ratio. If necessary, the compound of formula (8) can be used in excess. The hydrazine derivative of formula (10) can also be used in the form of salts such as hydrochloride or sulfate salts.

Examples of the solvent used in reactions 1 and 2 may include aliphatic hydrocarbons such as hexane, heptane, ligroin and petroleum ether; aromatic hydrocarbons such as benzene, toluene and xylene; halogenated hydrocarbons such as chlorobenzene, dichlorobenzene and benzotrifluoride; ethers such as diethyl ether, diisopropyl ether, 1,4-dioxane, tetrahydrofuran, ethylene glycol dimethyl ether and methyl t-butyl ether; alcohols such as methanol, ethanol, ethylene glycol and isopropanol; water; and mixtures thereof.

After completion of the reaction, water is added, if necessary, to the reaction mixture and the resulting crystals are collected by filtration, or the reaction mixture is subjected to ordinary post-treatments such as extraction with an organic solvent and concentration. If necessary, purification is subsequently carried out by a technique such as column chromatography or recrystallization. Thus, the desired products can be isolated.

The hydrazine derivatives of formula (10) can be produced by diazotizing aniline derivatives of formula (11):

wherein Q is as defined above, with nitrous acid, sodium nitrite or other agents under acidic conditions, and then reducing the diazonium salts with stannous chloride or other agents (see, e.g., Organic Synthesis Collective Volume 1, p. 442).

The aniline derivatives of formula (11) are known in, for example, European Patent Publication No. 61741-A, U.S. Pat. Nos. 4,670,046, 4,770,695, 4,709,049, 4,640,707, 4,720,297 and 5,169,431, and Japanese Patent Laid-open Publication No. 63-156787, or can be produced according to the methods as described therein.

The hydrazone compounds of formula (5) can also be produced from the aniline derivatives of formula (11) according to the following scheme:

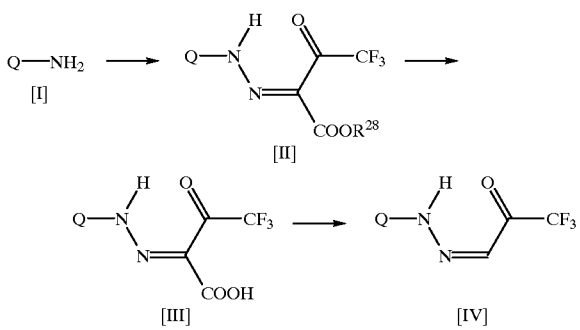

wherein Q is as defined above and $R^{28}$ is $C_1$–$C_6$ alkyl.

The reactions in the respective steps are effected, for example, as follows:

(1) Step of producing compound [II] from compound [I]

Compound [II] can be produced by reacting compound [I] with a nitrite salt such as sodium nitrite or potassium nitrite in water under acidic conditions to give the corresponding diazonium salt, and then reacting the diazonium salt with a compound of formula (12):

wherein Q and $R^{28}$ are as defined above, in the presence of a base such as sodium acetate or pyridine (see Tetrahedron, vol. 35, p. 2013 (1979)).

(2) Step of producing compound [III] from compound [II]

Compound [III] can be usually produced by hydrolyzing compound [II] in the presence of a base in a solvent.

The reaction temperature is usually in the range of 0° to 100° C. The reaction time is usually in the range of a moment to 24 hours.

The amount of reagent to be used in the reaction is usually 1 mole of the base for each one mole of compound [II], which is the stoichiometric ratio; however, it can be changed, if necessary.

Examples of the base used in the reaction may include inorganic bases such as sodium hydroxide, lithium hydroxide, lithium hydroxide monohydrate, barium hydroxide and potassium hydroxide.

Examples of the solvent used in the reaction may include aliphatic hydrocarbons such as hexane, heptane, ligroin and petroleum ether; aromatic hydrocarbons such as benzene, toluene and xylene; halogenated hydrocarbons such as chlorobenzene, dichlorobenzene and benzotrifluoride; ethers such as diethyl ether, diisopropyl ether, 1,4-dioxane, tetrahydrofuran, ethylene glycol dimethyl ether and methyl t-butyl ether; alcohols such as methanol, ethanol, ethylene glycol and isopropanol; water; and mixtures thereof.

(3) Step of producing compound [IV] from compound [III]

Compound [IV] can be produced by heating compound [III] in a solvent to cause decarbonization.

The reaction temperature is usually in the range of 50° to 200° C. The reaction time is usually in the range of a moment to 72 hours.

Examples of the solvent used in the reaction may include aliphatic hydrocarbons such as hexane, heptane, ligroin and petroleum ether; aromatic hydrocarbons such as benzene, toluene and xylene; halogenated hydrocarbons such as chloroform, carbon tetrachloride, 1,2-dichloroethane, chlorobenzene, dichlorobenzene and benzotrifluoride; ethers such as diethyl ether, diisopropyl ether, 1,4-dioxane, tetrahydrofuran, ethylene glycol dimethyl ether and methyl t-butyl ether; ketones such as acetone, methyl ethyl ketone, methyl isobutyl ketone and cyclohexanone; acid amides such as N,N-dimethylformamide; tertiary amines such as triethylamine, diisopropylethylamine, N,N-dimethylaniline, N,N-diethylaniline and N-methylmorpholine; nitrogen-containing aromatic compounds such as pyridine and picoline; sulfur-containing compounds such as dimethylsulfoxide and sulforane; fatty acids such as formic acid, acetic acid and propionic acid; alcohols such as methanol, ethanol, ethylene glycol and isopropanol; water; and mixtures thereof.

The reaction can also be effected, if necessary, with a metal catalyst such as copper.

After completion of the reaction, the reaction mixture is filtered for collection of the resulting crystals or subjected to ordinary post-treatments such as extraction with an organic solvent and concentration. If necessary, purification is subsequently carried out by a technique such as chromatography or recrystallization. Thus, the desired products can be isolated.

The hydrazone compound [IV] wherein Q is Q-1, B is $OR^1$ or $SR^1$, and $R^1$ is carboxy $C_1$–$C_6$ alkyl can also be produced by the hydrolysis and decarbonization of compound [II] wherein Q is Q-1, B is $OR^1$ or $SR^1$, and $R^1$ is ($C_1$–$C_8$ alkoxy)carbonyl $C_1$–$C_6$ alkyl.

Tables 1 to 22 show the present compounds and their salts obtained by the above production process, and Tables 23 and 24 show the hydrazone compounds of formula (5) and the malonic acid derivatives of formula (6), respectively, which are used in process 1. These compounds and salts are to be construed as merely illustrative and not limitations of the present invention. In these tables, "c-" means cyclo-; "i-" iso-; "Et" ethyl; and "Bu" butyl.

Compounds of Formula (13)

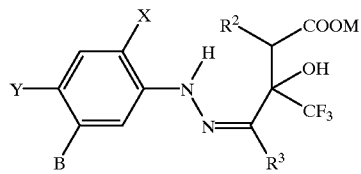

TABLE 1

| Compound | X | Y | M | $R^2$ | $R^3$ | B |
|---|---|---|---|---|---|---|
| 1-1 | F | Cl | H | $CH_3$ | H | H |
| 1-2 | F | Cl | H | $CH_3$ | H | OH |
| 1-3 | F | Cl | H | $CH_3$ | H | $OCH_3$ |
| 1-4 | F | Cl | H | $CH_3$ | H | $OC_2H_5$ |
| 1-5 | F | Cl | H | $CH_3$ | H | $OCH(CH_3)_2$ |
| 1-6 | F | Cl | H | $CH_3$ | H | $OCH_2CH=CH_2$ |

TABLE 1-continued

| Compound | X | Y | M | R² | R³ | B |
|---|---|---|---|---|---|---|
| 1-7 | F | Cl | H | CH₃ | H | OCH₂C≡CH |
| 1-8 | F | Cl | H | CH₃ | H | OCH(CH₃)C≡CH |
| 1-9 | F | Cl | H | CH₃ | H | OCH₂COOH |
| 1-10 | F | Cl | H | CH₃ | H | OCH₂COOCH₃ |
| 1-11 | F | Cl | H | CH₃ | H | OCH₂COOC₂H₅ |
| 1-12 | F | Cl | H | CH₃ | H | OCH₂COOC₃H₇ |
| 1-13 | F | Cl | H | CH₃ | H | OCH₂COOC₄H₉ |
| 1-14 | F | Cl | H | CH₃ | H | OCH₂COOC₅H₁₁ |
| 1-15 | F | Cl | H | CH₃ | H | OCH₂COO-i-C₃H₇ |
| 1-16 | F | Cl | H | CH₃ | H | OCH₂COO-i-C₄H₉ |
| 1-17 | F | Cl | H | CH₃ | H | OCH₂COO-c-C₅H₉ |
| 1-18 | F | Cl | H | CH₃ | H | OCH₂COO-c-C₆H₁₁ |
| 1-19 | F | Cl | H | CH₃ | H | OCH(CH₃)COOH |
| 1-20 | F | Cl | H | CH₃ | H | OCH(CH₃)COOCH₃ |
| 1-21 | F | Cl | H | CH₃ | H | OCH(CH₃)COOC₂H₅ |
| 1-22 | F | Cl | H | CH₃ | H | OCH(CH₃)COOC₃H₇ |
| 1-23 | F | Cl | H | CH₃ | H | OCH(CH₃)COOC₄H₉ |
| 1-24 | F | Cl | H | CH₃ | H | OCH(CH₃)COOC₅H₁₁ |
| 1-25 | F | Cl | H | CH₃ | H | OCH(CH₃)COO-i-C₃H₇ |
| 1-26 | F | Cl | H | CH₃ | H | OCH(CH₃)COO-i-C₄H₉ |

TABLE 2

| Compound | X | Y | M | R² | R³ | B |
|---|---|---|---|---|---|---|
| 1-27 | F | Cl | H | CH₃ | H | OCH(CH₃)COO-c-C₅H₉ |
| 1-28 | F | Cl | H | CH₃ | H | OCH(CH₃)COO-c-C₆H₁₁ |
| 1-29 | F | Cl | H | CH₃ | H | O-c-C₅H₉ |
| 1-30 | F | Cl | H | CH₃ | H | O-c-C₆H₁₁ |
| 1-31 | F | Cl | H | CH₃ | H | SCH₂C≡CH |
| 1-32 | F | Cl | H | CH₃ | H | SCH(CH₃)C≡CH |
| 1-33 | F | Cl | H | CH₃ | H | SCH₂COOH |
| 1-34 | F | Cl | H | CH₃ | H | SCH₂COOCH₃ |
| 1-35 | F | Cl | H | CH₃ | H | SCH₂COOC₂H₅ |
| 1-36 | F | Cl | H | CH₃ | H | SCH₂COOC₃H₇ |
| 1-37 | F | Cl | H | CH₃ | H | SCH₂COOC₄H₉ |
| 1-38 | F | Cl | H | CH₃ | H | SCH₂COOC₅H₁₁ |
| 1-39 | F | Cl | H | CH₃ | H | SCH₂COO-i-C₃H₇ |
| 1-40 | F | Cl | H | CH₃ | H | SCH₂COO-i-C₄H₉ |
| 1-41 | F | Cl | H | CH₃ | H | SCH₂COO-c-C₅H₉ |
| 1-42 | F | Cl | H | CH₃ | H | SCH₂COO-c-C₆H₁₁ |
| 1-43 | F | Cl | H | CH₃ | H | SCH(CH₃)COOH |
| 1-44 | F | Cl | H | CH₃ | H | SCH(CH₃)COOCH₃ |
| 1-45 | F | Cl | H | CH₃ | H | SCH(CH₃)COOC₂H₅ |
| 1-46 | F | Cl | H | CH₃ | H | SCH(CH₃)COOC₃H₇ |
| 1-47 | F | Cl | H | CH₃ | H | SCH(CH₃)COOC₄H₉ |
| 1-48 | F | Cl | H | CH₃ | H | SCH(CH₃)COOC₅H₁₁ |
| 1-49 | F | Cl | H | CH₃ | H | SCH(CH₃)COO-i-C₃H₇ |
| 1-50 | F | Cl | H | CH₃ | H | SCH(CH₃)COO-i-C₄H₉ |
| 1-51 | F | Cl | H | CH₃ | H | SCH(CH₃)COO-c-C₅H₉ |
| 1-52 | F | Cl | H | CH₃ | H | SCH(CH₃)COO-c-C₆H₁₁ |

TABLE 3

| Compound | X | Y | M | R² | R³ | B |
|---|---|---|---|---|---|---|
| 1-53 | F | Cl | H | CH₃ | H | COOH |
| 1-54 | F | Cl | H | CH₃ | H | COOCH₃ |
| 1-55 | F | Cl | H | CH₃ | H | COOC₂H₅ |
| 1-56 | F | Cl | H | CH₃ | H | COOC₃H₇ |
| 1-57 | F | Cl | H | CH₃ | H | COOC₄H₉ |
| 1-58 | F | Cl | H | CH₃ | H | COOCH(CH₃)₂ |
| 1-59 | F | Cl | H | CH₃ | H | CH₂CH₂COOC₂H₅ |
| 1-60 | F | Cl | H | CH₃ | H | CH₂CHClCOOC₂H₅ |
| 1-61 | F | Cl | H | H | H | H |
| 1-62 | F | Cl | H | H | H | OH |
| 1-63 | F | Cl | H | H | H | OCH₃ |
| 1-64 | F | Cl | H | H | H | OC₂H₅ |
| 1-65 | F | Cl | H | H | H | OCH(CH₃)₂ |
| 1-66 | F | Cl | H | H | H | OCH₂CH=CH₂ |

TABLE 3-continued

| Compound | X | Y | M | R² | R³ | B |
|---|---|---|---|---|---|---|
| 1-67 | F | Cl | H | H | H | OCH₂C≡CH |
| 1-68 | F | Cl | H | H | H | OCH(CH₃)C≡CH |
| 1-69 | F | Cl | H | H | H | OCH₂COOH |
| 1-70 | F | Cl | H | H | H | OCH₂COOCH₃ |
| 1-71 | F | Cl | H | H | H | OCH₂COOC₂H₅ |
| 1-72 | F | Cl | H | H | H | OCH₂COOC₃H₇ |
| 1-73 | F | Cl | H | H | H | OCH₂COOC₄H₉ |
| 1-74 | F | Cl | H | H | H | OCH₂COOC₅H₁₁ |
| 1-75 | F | Cl | H | H | H | OCH₂COO-i-C₃H₇ |
| 1-76 | F | Cl | H | H | H | OCH₂COO-i-C₄H₉ |
| 1-77 | F | Cl | H | H | H | OCH₂COO-c-C₅H₉ |
| 1-78 | F | Cl | H | H | H | OCH₂COO-c-C₆H₁₁ |

TABLE 4

| Compound | X | Y | M | R² | R³ | B |
|---|---|---|---|---|---|---|
| 1-79 | F | Cl | H | H | H | OCH(CH₃)COOH |
| 1-80 | F | Cl | H | H | H | OCH(CH₃)COOCH₃ |
| 1-81 | F | Cl | H | H | H | OCH(CH₃)COOC₂H₅ |
| 1-82 | F | Cl | H | H | H | OCH(CH₃)COOC₃H₇ |
| 1-83 | F | Cl | H | H | H | OCH(CH₃)COOC₄H₉ |
| 1-84 | F | Cl | H | H | H | OCH(CH₃)COOC₅H₁₁ |
| 1-85 | F | Cl | H | H | H | OCH(CH₃)COO-i-C₃H₇ |
| 1-86 | F | Cl | H | H | H | OCH(CH₃)COO-i-C₄H₉ |
| 1-87 | F | Cl | H | H | H | OCH(CH₃)COO-c-C₅H₉ |
| 1-88 | F | Cl | H | H | H | OCH(CH₃)COO-c-C₆H₁₁ |
| 1-89 | F | Cl | H | H | H | O-c-C₅H₉ |
| 1-90 | F | Cl | H | H | H | O-c-C₆H₁₁ |
| 1-91 | F | Cl | H | H | H | SCH₂C≡CH |
| 1-92 | F | Cl | H | H | H | SCH(CH₃)C≡CH |
| 1-93 | F | Cl | H | H | H | SCH₂COOH |
| 1-94 | F | Cl | H | H | H | SCH₂COOCH₃ |
| 1-95 | F | Cl | H | H | H | SCH₂COOC₂H₅ |
| 1-96 | F | Cl | H | H | H | SCH₂COOC₃H₇ |
| 1-97 | F | Cl | H | H | H | SCH₂COOC₄H₉ |
| 1-98 | F | Cl | H | H | H | SCH₂COOC₅H₁₁ |
| 1-99 | F | Cl | H | H | H | SCH₂COO-i-C₃H₇ |
| 1-100 | F | Cl | H | H | H | SCH₂COO-i-C₄H₉ |
| 1-101 | F | Cl | H | H | H | SCH₂COO-c-C₅H₉ |
| 1-102 | F | Cl | H | H | H | SCH₂COO-c-C₆H₁₁ |
| 1-103 | F | Cl | H | H | H | SCH(CH₃)COOH |
| 1-104 | F | Cl | H | H | H | SCH(CH₃)COOCH₃ |

TABLE 5

| Compound | X | Y | M | R² | R³ | B |
|---|---|---|---|---|---|---|
| 1-105 | F | Cl | H | H | H | SCH(CH₃)COOC₂H₅ |
| 1-106 | F | Cl | H | H | H | SCH(CH₃)COOC₃H₇ |
| 1-107 | F | Cl | H | H | H | SCH(CH₃)COOC₄H₉ |
| 1-108 | F | Cl | H | H | H | SCH(CH₃)COOC₅H₁₁ |
| 1-109 | F | Cl | H | H | H | SCH(CH₃)COO-i-C₃H₇ |
| 1-110 | F | Cl | H | H | H | SCH(CH₃)COO-i-C₄H₉ |
| 1-111 | F | Cl | H | H | H | SCH(CH₃)COO-c-C₅H₉ |
| 1-112 | F | Cl | H | H | H | SCH(CH₃)COO-c-C₆H₁₁ |
| 1-113 | F | Cl | H | H | H | COOH |
| 1-114 | F | Cl | H | H | H | COOCH₃ |
| 1-115 | F | Cl | H | H | H | COOC₂H₅ |
| 1-116 | F | Cl | H | H | H | COOC₃H₇ |
| 1-117 | F | Cl | H | H | H | COOC₄H₉ |
| 1-118 | F | Cl | H | H | H | COOCH(CH₃)₂ |
| 1-119 | F | Cl | H | H | H | CH₂CH₂COOC₂H₅ |
| 1-120 | F | Cl | H | H | H | CH₂CHClCOOC₂H₅ |
| 1-121 | H | Cl | CH₃ | H | H | H |
| 1-122 | H | Cl | CH₃ | H | H | OH |
| 1-123 | H | Cl | CH₃ | H | H | OCH₃ |
| 1-124 | H | Cl | CH₃ | H | H | OC₂H₅ |
| 1-125 | H | Cl | CH₃ | H | H | OCH(CH₃)₂ |
| 1-126 | H | Cl | CH₃ | H | H | OCH₂C≡CH |

TABLE 5-continued

| Compound | X | Y | M | R² | R³ | B |
|---|---|---|---|---|---|---|
| 1-127 | H | Cl | CH₃ | H | H | OCH(CH₃)C≡CH |
| 1-128 | H | Cl | H | H | H | H |
| 1-129 | H | Cl | H | H | H | OH |
| 1-130 | H | Cl | H | H | H | CH₃ |

TABLE 6

| Compound | X | Y | M | R² | R³ | B |
|---|---|---|---|---|---|---|
| 1-131 | H | Cl | H | H | H | OC₂H₅ |
| 1-132 | H | Cl | H | H | H | OCH(CH₃)₂ |
| 1-133 | H | Cl | H | H | H | OCH₂C≡CH |
| 1-134 | H | Cl | H | H | H | OCH(CH₃)C≡CH |
| 1-135 | Cl | Cl | H | CH₃ | H | H |
| 1-136 | Cl | Cl | H | CH₃ | H | OH |
| 1-137 | Cl | Cl | H | CH₃ | H | OCH₃ |
| 1-138 | Cl | Cl | H | CH₃ | H | OC₂H₅ |
| 1-139 | Cl | Cl | H | CH₃ | H | OCH(CH₃)₂ |
| 1-140 | Cl | Cl | H | CH₃ | H | OCH₂C≡CH |
| 1-141 | Cl | Cl | H | CH₃ | H | OCH(CH₃)C≡CH |
| 1-142 | Cl | Cl | H | H | H | H |
| 1-143 | Cl | Cl | H | H | H | OH |
| 1-144 | Cl | Cl | H | H | H | OCH₃ |
| 1-145 | Cl | Cl | H | H | H | OC₂H₅ |
| 1-146 | Cl | Cl | H | H | H | OCH(CH₃)₂ |
| 1-147 | Cl | Cl | H | H | H | OCH₂C≡CH |
| 1-148 | Cl | Cl | H | H | H | OCH(CH₃)C≡CH |
| 1-149 | F | Cl | H | C₂H₅ | H | H |
| 1-150 | F | Cl | H | C₂H₅ | H | OH |
| 1-151 | F | Cl | H | C₂H₅ | H | OCH₃ |
| 1-152 | F | Cl | H | C₂H₅ | H | OC₂H₅ |
| 1-153 | F | Cl | H | C₂H₅ | H | OCH(CH₃)₂ |
| 1-154 | F | Cl | H | C₂H₅ | H | OCH₂C≡CH |
| 1-155 | F | Cl | H | C₂H₅ | H | OCH(CH₃)CH≡CH |
| 1-156 | F | Cl | H | C₂H₅ | H | OCH₂COOH |

TABLE 7

| Compound | X | Y | M | R² | R³ | B |
|---|---|---|---|---|---|---|
| 1-157 | F | Cl | H | C₂H₅ | H | OCH₂COOCH₃ |
| 1-158 | F | Cl | H | C₂H₅ | H | OCH₂COOC₂H₅ |
| 1-159 | F | Cl | H | C₂H₅ | H | OCH₂COOC₃H₇ |
| 1-160 | F | Cl | H | C₂H₅ | H | OCH₂COOC₄H₉ |
| 1-161 | F | Cl | H | C₂H₅ | H | OCH₂COOC₅H₁₁ |
| 1-162 | F | Cl | H | C₂H₅ | H | OCH(CH₃)COOH |
| 1-163 | F | Cl | H | C₂H₅ | H | OCH(CH₃)COOCH₃ |
| 1-164 | F | Cl | H | C₂H₅ | H | OCH(CH₃)COOC₂H₅ |
| 1-165 | F | Cl | H | C₂H₅ | H | OCH(CH₃)COOC₃H₇ |
| 1-166 | F | Cl | H | C₂H₅ | H | OCH(CH₃)COOC₄H₉ |
| 1-167 | F | Cl | H | C₂H₅ | H | OCH(CH₃)COOC₅H₁₁ |
| 1-168 | F | Cl | H | C₂H₅ | H | COOH |
| 1-169 | F | Cl | H | C₂H₅ | H | COOCH₃ |
| 1-170 | F | Cl | H | C₂H₅ | H | COOC₂H₅ |
| 1-171 | F | Cl | H | C₂H₅ | H | COOC₃H₇ |
| 1-172 | F | Cl | H | C₂H₅ | H | COOC₄H₉ |
| 1-173 | F | Cl | H | C₂H₅ | H | COOCH(CH₃)₂ |
| 1-174 | F | Cl | H | H | CH₃ | H |
| 1-175 | F | Cl | H | H | CH₃ | OH |
| 1-176 | F | Cl | H | H | CH₃ | OCH₃ |
| 1-177 | F | Cl | H | H | CH₃ | OC₂H₅ |
| 1-178 | F | Cl | H | H | CH₃ | OCH(CH₃)₂ |
| 1-179 | F | Cl | H | H | CH₃ | OCH₂C≡CH |
| 1-180 | F | Cl | H | H | CH₃ | OCH(CH₃)C≡CH |
| 1-181 | F | Cl | H | H | CH₃ | OCH₂COOH |
| 1-182 | F | Cl | H | H | CH₃ | OCH₂COOCH₃ |

TABLE 8

| Compound | X | Y | M | R² | R³ | B |
|---|---|---|---|---|---|---|
| 1-183 | F | Cl | H | H | CH₃ | OCH₂COOC₂H₅ |
| 1-184 | F | Cl | H | H | CH₃ | OCH₂COOC₃H₇ |
| 1-185 | F | Cl | H | H | CH₃ | OCH₂COOC₄H₉ |
| 1-186 | F | Cl | H | H | CH₃ | OCH₂COOC₅H₁₁ |
| 1-187 | F | Cl | H | H | CH₃ | OCH(CH₃)COOH |
| 1-188 | F | Cl | H | H | CH₃ | OCH(CH₃)COOCH₃ |
| 1-189 | F | Cl | H | H | CH₃ | OCH(CH₃)COOC₂H₅ |
| 1-190 | F | Cl | H | H | CH₃ | OCH(CH₃)COOC₃H₇ |
| 1-191 | F | Cl | H | H | CH₃ | OCH(CH₃)COOC₄H₉ |
| 1-192 | F | Cl | H | H | CH₃ | OCH(CH₃)COOC₅H₁₁ |
| 1-193 | F | Cl | H | H | CH₃ | SCH₂COOH |
| 1-194 | F | Cl | H | H | CH₃ | SCH₂COOCH₃ |
| 1-195 | F | Cl | H | H | CH₃ | SCH₂COOC₂H₅ |
| 1-196 | F | Cl | H | H | CH₃ | SCH₂COOC₃H₇ |
| 1-197 | F | Cl | H | H | CH₃ | SCH₂COOC₄H₉ |
| 1-198 | F | Cl | H | H | CH₃ | SCH₂COOC₅H₁₁ |
| 1-199 | F | Cl | H | H | CH₃ | SCH₂COO-c-C₅H₉ |
| 1-200 | F | Cl | H | H | CH₃ | SCH₂COO-c-C₆H₁₁ |
| 1-201 | F | Cl | H | H | CH₃ | SCH(CH₃)COOH |
| 1-202 | F | Cl | H | H | CH₃ | SCH(CH₃)COOCH₃ |
| 1-203 | F | Cl | H | H | CH₃ | SCH(CH₃)COOC₂H₅ |
| 1-204 | F | Cl | H | H | CH₃ | SCH(CH₃)COOC₃H₇ |
| 1-205 | F | Cl | H | H | CH₃ | SCH(CH₃)COOC₄H₉ |
| 1-206 | F | Cl | H | H | CH₃ | SCH(CH₃)COOC₅H₁₁ |
| 1-207 | F | Cl | H | H | CH₃ | COOH |
| 1-208 | F | Cl | H | H | CH₃ | COOCH₃ |

TABLE 9

| Compound | X | Y | M | R² | R³ | B |
|---|---|---|---|---|---|---|
| 1-209 | F | Cl | H | H | CH₃ | COOC₂H₅ |
| 1-210 | F | Cl | H | H | CH₃ | COOC₃H₇ |
| 1-211 | F | Cl | H | H | CH₃ | COOC₄H₉ |
| 1-212 | F | Cl | H | H | CH₃ | COOCH(CH₃)₂ |
| 1-213 | F | Cl | Na | H | H | H |
| 1-214 | F | Cl | Na | H | H | OH |
| 1-215 | F | Cl | Na | H | H | OCH₃ |
| 1-216 | F | Cl | Na | H | H | OC₂H₅ |
| 1-217 | F | Cl | Na | H | H | OCH(CH₃)₂ |
| 1-218 | F | Cl | Na | H | H | OCH₂C≡CH |
| 1-219 | F | Cl | Na | H | H | OCH(CH₃)C≡CH |
| 1-220 | F | Cl | Na | H | H | OCH₂COOCH₃ |
| 1-221 | F | Cl | Na | H | H | OCH₂COOC₂H₅ |
| 1-222 | F | Cl | Na | H | H | OCH₂COOC₃H₇ |
| 1-223 | F | Cl | Na | H | H | OCH₂COOC₄H₉ |
| 1-224 | F | Cl | Na | H | H | OCH₂COOC₅H₁₁ |
| 1-225 | F | Cl | Na | H | H | OCH(CH₃)COOCH₃ |
| 1-226 | F | Cl | Na | H | H | OCH(CH₃)COOC₂H₅ |
| 1-227 | F | Cl | Na | H | H | OCH(CH₃)COOC₃H₇ |
| 1-228 | F | Cl | Na | H | H | OCH(CH₃)COOC₄H₉ |
| 1-229 | F | Cl | Na | H | H | OCH(CH₃)COOC₅H₁₁ |
| 1-230 | F | Cl | Na | H | H | SCH₂COOCH₃ |
| 1-231 | F | Cl | Na | H | H | SCH₂COOC₂H₅ |
| 1-232 | F | Cl | Na | H | H | SCH₂COOC₃H₇ |
| 1-233 | F | Cl | Na | H | H | SCH₂COOC₄H₉ |
| 1-234 | F | Cl | Na | H | H | SCH₂COOC₅H₁₁ |

TABLE 10

| Compound | X | Y | M | R² | R³ | B |
|---|---|---|---|---|---|---|
| 1-235 | F | Cl | Na | H | H | SCH₂COO-c-C₅H₉ |
| 1-236 | F | Cl | Na | H | H | SCH₂COO-c-C₆H₁₁ |
| 1-237 | F | Cl | Na | H | H | SCH(CH₃)COO-c-C₅H₉ |
| 1-238 | F | Cl | Na | H | H | SCH(CH₃)COOCH₃ |
| 1-239 | F | Cl | Na | H | H | SCH(CH₃)COOC₂H₅ |
| 1-240 | F | Cl | Na | H | H | SCH(CH₃)COOC₃H₇ |
| 1-241 | F | Cl | Na | H | H | SCH(CH₃)COOC₄H₉ |
| 1-242 | F | Cl | Na | H | H | SCH(CH₃)COOC₅H₁₁ |

TABLE 10-continued

| Compound | X | Y | M | $R^2$ | $R^3$ | B |
|---|---|---|---|---|---|---|
| 1-243 | F | Cl | Na | H | H | COOCH$_3$ |
| 1-244 | F | Cl | Na | H | H | COOC$_2$H$_5$ |
| 1-245 | F | Cl | Na | H | H | COOC$_3$H$_7$ |
| 1-246 | F | Cl | Na | H | H | COOC$_4$H$_9$ |
| 1-247 | F | Cl | Na | H | H | COOCH(CH$_3$)$_2$ |
| 1-248 | F | Cl | K | H | H | H |
| 1-249 | F | Cl | K | H | H | OH |
| 1-250 | F | Cl | K | H | H | OCH$_3$ |
| 1-251 | F | Cl | K | H | H | OC$_2$H$_5$ |
| 1-252 | F | Cl | K | H | H | OCH(CH$_3$)$_2$ |
| 1-253 | F | Cl | K | H | H | OCH$_2$C≡CH |
| 1-254 | F | Cl | K | H | H | OCH(CH$_3$)C≡CH |
| 1-255 | F | Cl | K | H | H | OCH$_2$COOCH$_3$ |
| 1-256 | F | Cl | K | H | H | OCH$_2$COOC$_2$H$_5$ |
| 1-257 | F | Cl | K | H | H | OCH$_2$COOC$_3$H$_7$ |
| 1-258 | F | Cl | K | H | H | OCH$_2$COOC$_4$H$_9$ |
| 1-259 | F | Cl | K | H | H | OCH$_2$COOC$_5$H$_{11}$ |
| 1-260 | F | Cl | K | H | H | OCH(CH$_3$)COOCH$_3$ |

TABLE 11

| Compound | X | Y | M | $R^2$ | $R^3$ | B |
|---|---|---|---|---|---|---|
| 1-261 | F | Cl | K | H | H | OCH(CH$_3$)COOC$_2$H$_5$ |
| 1-262 | F | Cl | K | H | H | OCH(CH$_3$)COOC$_3$H$_7$ |
| 1-263 | F | Cl | K | H | H | OCH(CH$_3$)COOC$_4$H$_9$ |
| 1-264 | F | Cl | K | H | H | OCH(CH$_3$)COOC$_5$H$_{11}$ |
| 1-265 | F | Cl | K | H | H | SCH$_2$COOCH$_3$ |
| 1-266 | F | Cl | K | H | H | SCH$_2$COOC$_2$H$_5$ |
| 1-267 | F | Cl | K | H | H | SCH$_2$COOC$_3$H$_7$ |
| 1-268 | F | Cl | K | H | H | SCH$_2$COOC$_4$H$_9$ |
| 1-269 | F | Cl | K | H | H | SCH$_2$COOC$_5$H$_{11}$ |
| 1-270 | F | Cl | K | H | H | SCH$_2$COO-c-C$_5$H$_9$ |
| 1-271 | F | Cl | K | H | H | SCH$_2$COO-c-C$_6$H$_{11}$ |
| 1-272 | F | Cl | K | H | H | SCH(CH$_3$)COO-c-C$_5$H$_9$ |
| 1-273 | F | Cl | K | H | H | SCH(CH$_3$)COOCH$_3$ |
| 1-274 | F | Cl | K | H | H | SCH(CH$_3$)COOC$_2$H$_5$ |
| 1-275 | F | Cl | K | H | H | SCH(CH$_3$)COOC$_3$H$_7$ |
| 1-276 | F | Cl | K | H | H | SCH(CH$_3$)COOC$_4$H$_9$ |
| 1-277 | F | Cl | K | H | H | SCH(CH$_3$)COOC$_5$H$_{11}$ |
| 1-278 | F | Cl | K | H | H | COOCH$_3$ |
| 1-279 | F | Cl | K | H | H | COOC$_2$H$_5$ |
| 1-280 | F | Cl | K | H | H | COOC$_3$H$_7$ |
| 1-281 | F | Cl | K | H | H | COOC$_4$H$_9$ |
| 1-282 | F | Cl | K | H | H | COOCH(CH$_3$)$_2$ |
| 1-283 | F | Cl | HNEt$_3$ | H | H | H |
| 1-284 | F | Cl | HNEt$_3$ | H | H | OH |
| 1-285 | F | Cl | HNEt$_3$ | H | H | OCH$_3$ |
| 1-286 | F | Cl | HNEt$_3$ | H | H | OC$_2$H$_5$ |

TABLE 12

| Compound | X | Y | M | $R^2$ | $R^3$ | B |
|---|---|---|---|---|---|---|
| 1-287 | F | Cl | HNEt$_3$ | H | H | OCH(CH$_3$)$_2$ |
| 1-288 | F | Cl | HNEt$_3$ | H | H | OCH$_2$C≡CH |
| 1-289 | F | Cl | HNEt$_3$ | H | H | OCH(CH$_3$)C≡CH |
| 1-290 | F | Cl | HNEt$_3$ | H | H | OCH$_2$COOCH$_3$ |
| 1-291 | F | Cl | HNEt$_3$ | H | H | OCH$_2$COOC$_2$H$_5$ |
| 1-292 | F | Cl | HNEt$_3$ | H | H | OCH$_2$COOC$_3$H$_7$ |
| 1-293 | F | Cl | HNEt$_3$ | H | H | OCH$_2$COOC$_4$H$_9$ |
| 1-294 | F | Cl | HNEt$_3$ | H | H | OCH$_2$COOC$_5$H$_{11}$ |
| 1-295 | F | Cl | HNEt$_3$ | H | H | OCH(CH$_3$)COOCH$_3$ |
| 1-296 | F | Cl | HNEt$_3$ | H | H | OCH(CH$_3$)COOC$_2$H$_5$ |
| 1-297 | F | Cl | HNEt$_3$ | H | H | OCH(CH$_3$)COOC$_3$H$_7$ |
| 1-298 | F | Cl | HNEt$_3$ | H | H | OCH(CH$_3$)COOC$_4$H$_9$ |
| 1-299 | F | Cl | HNEt$_3$ | H | H | OCH(CH$_3$)COOC$_5$H$_{11}$ |
| 1-300 | F | Cl | HNEt$_3$ | H | H | SCH$_2$COOCH$_3$ |
| 1-301 | F | Cl | HNEt$_3$ | H | H | SCH$_2$COOC$_2$H$_5$ |
| 1-302 | F | Cl | HNEt$_3$ | H | H | SCH$_2$COOC$_3$H$_7$ |

TABLE 12-continued

| Compound | X | Y | M | $R^2$ | $R^3$ | B |
|---|---|---|---|---|---|---|
| 1-303 | F | Cl | HNEt$_3$ | H | H | SCH$_2$COOC$_4$H$_9$ |
| 1-304 | F | Cl | HNEt$_3$ | H | H | SCH$_2$COOC$_5$H$_{11}$ |
| 1-305 | F | Cl | HNEt$_3$ | H | H | SCH$_2$COO-c-C$_5$H$_9$ |
| 1-306 | F | Cl | HNEt$_3$ | H | H | SCH$_2$COO-c-C$_6$H$_{11}$ |
| 1-307 | F | Cl | HNEt$_3$ | H | H | SCH(CH$_3$)COO-c-C$_5$H$_9$ |
| 1-308 | F | Cl | HNEt$_3$ | H | H | SCH(CH$_3$)COOCH$_3$ |
| 1-309 | F | Cl | HNEt$_3$ | H | H | SCH(CH$_3$)COOC$_2$H$_5$ |
| 1-310 | F | Cl | HNEt$_3$ | H | H | SCH(CH$_3$)COOC$_3$H$_7$ |
| 1-311 | F | Cl | HNEt$_3$ | H | H | SCH(CH$_3$)COOC$_4$H$_9$ |
| 1-312 | F | Cl | HNEt$_3$ | H | H | SCH(CH$_3$)COOC$_5$H$_{11}$ |

TABLE 13

| Compound | X | Y | M | $R^2$ | $R^3$ | B |
|---|---|---|---|---|---|---|
| 1-313 | F | Cl | HNEt$_3$ | H | H | COOCH$_3$ |
| 1-314 | F | Cl | HNEt$_3$ | H | H | COOC$_2$H$_5$ |
| 1-315 | F | Cl | HNEt$_3$ | H | H | COOC$_3$H$_7$ |
| 1-316 | F | Cl | HNEt$_3$ | H | H | COOC$_4$H$_9$ |
| 1-317 | F | Cl | HNEt$_3$ | H | H | COOCH(CH$_3$)$_2$ |
| 1-318 | F | Cl | HNBu$_3$ | H | H | H |
| 1-319 | F | Cl | HNBu$_3$ | H | H | OH |
| 1-320 | F | Cl | HNBu$_3$ | H | H | OCH$_3$ |
| 1-321 | F | Cl | HNBu$_3$ | H | H | OC$_2$H$_5$ |
| 1-322 | F | Cl | HNBu$_3$ | H | H | OCH(CH$_3$)$_2$ |
| 1-323 | F | Cl | HNBu$_3$ | H | H | OCH$_2$C≡CH |
| 1-324 | F | Cl | HNBu$_3$ | H | H | OCH(CH$_3$)C≡CH |
| 1-325 | F | Cl | HNBu$_3$ | H | H | OCH$_2$COOCH$_3$ |
| 1-326 | F | Cl | HNBu$_3$ | H | H | OCH$_2$COOC$_2$H$_5$ |
| 1-327 | F | Cl | HNBu$_3$ | H | H | OCH$_2$COOC$_3$H$_7$ |
| 1-328 | F | Cl | HNBu$_3$ | H | H | OCH$_2$COOC$_4$H$_9$ |
| 1-329 | F | Cl | HNBu$_3$ | H | H | OCH$_2$COOC$_5$H$_{11}$ |
| 1-330 | F | Cl | HNBu$_3$ | H | H | OCH(CH$_3$)COOCH$_3$ |
| 1-331 | F | Cl | HNBu$_3$ | H | H | OCH(CH$_3$)COOC$_2$H$_5$ |
| 1-332 | F | Cl | HNBu$_3$ | H | H | OCH(CH$_3$)COOC$_3$H$_7$ |
| 1-333 | F | Cl | HNBu$_3$ | H | H | OCH(CH$_3$)COOC$_4$H$_9$ |
| 1-334 | F | Cl | HNBu$_3$ | H | H | OCH(CH$_3$)COOC$_5$H$_{11}$ |
| 1-335 | F | Cl | HNBu$_3$ | H | H | SCH$_2$COOCH$_3$ |
| 1-336 | F | Cl | HNBu$_3$ | H | H | SCH$_2$COOC$_2$H$_5$ |
| 1-337 | F | Cl | HNBu$_3$ | H | H | SCH$_2$COOC$_3$H$_7$ |
| 1-338 | F | Cl | HNBu$_3$ | H | H | SCH$_2$COOC$_4$H$_9$ |

TABLE 14

| Compound | X | Y | M | $R^2$ | $R^3$ | B |
|---|---|---|---|---|---|---|
| 1-339 | F | Cl | HNBu$_3$ | H | H | SCH$_2$COOC$_5$H$_{11}$ |
| 1-340 | F | Cl | HNBu$_3$ | H | H | SCH$_2$COO-c-C$_5$H$_9$ |
| 1-341 | F | Cl | HNBu$_3$ | H | H | SCH$_2$COO-c-C$_6$H$_{11}$ |
| 1-342 | F | Cl | HNBu$_3$ | H | H | SCH(CH$_3$)COOH |
| 1-343 | F | Cl | HNBu$_3$ | H | H | SCH(CH$_3$)COOCH$_3$ |
| 1-344 | F | Cl | HNBu$_3$ | H | H | SCH(CH$_3$)COOC$_2$H$_5$ |
| 1-345 | F | Cl | HNBu$_3$ | H | H | SCH(CH$_3$)COOC$_3$H$_7$ |
| 1-346 | F | Cl | HNBu$_3$ | H | H | SCH(CH$_3$)COOC$_4$H$_9$ |
| 1-347 | F | Cl | HNBu$_3$ | H | H | SCH(CH$_3$)COOC$_5$H$_{11}$ |
| 1-348 | F | Cl | HNBu$_3$ | H | H | COOCH$_3$ |
| 1-349 | F | Cl | HNBu$_3$ | H | H | COOC$_2$H$_5$ |
| 1-350 | F | Cl | HNBu$_3$ | H | H | COOC$_3$H$_7$ |
| 1-351 | F | Cl | HNBu$_3$ | H | H | COOC$_4$H$_9$ |
| 1-352 | F | Cl | HNBu$_3$ | H | H | COOCH(CH$_3$)$_2$ |
| 1-353 | F | Cl | Na | CH$_3$ | H | H |
| 1-354 | F | Cl | Na | CH$_3$ | H | OH |
| 1-355 | F | Cl | Na | CH$_3$ | H | OCH$_3$ |
| 1-356 | F | Cl | Na | CH$_3$ | H | OC$_2$H$_5$ |
| 1-357 | F | Cl | Na | CH$_3$ | H | OCH(CH$_3$)$_2$ |
| 1-358 | F | Cl | Na | CH$_3$ | H | OCH$_2$C≡CH |
| 1-359 | F | Cl | Na | CH$_3$ | H | OCH(CH$_3$)C≡CH |
| 1-360 | F | Cl | Na | CH$_3$ | H | OCH$_2$COOCH$_3$ |
| 1-361 | F | Cl | Na | CH$_3$ | H | OCH$_2$COOC$_2$H$_5$ |
| 1-362 | F | Cl | Na | CH$_3$ | H | OCH$_2$COOC$_3$H$_7$ |

TABLE 14-continued

| Compound | X | Y | M | $R^2$ | $R^3$ | B |
|---|---|---|---|---|---|---|
| 1-363 | F | Cl | Na | $CH_3$ | H | $OCH_2COOC_4H_9$ |
| 1-364 | F | Cl | Na | $CH_3$ | H | $OCH_2COOC_5H_{11}$ |

TABLE 15

| Compound | X | Y | M | $R^2$ | $R^3$ | B |
|---|---|---|---|---|---|---|
| 1-365 | F | Cl | Na | $CH_3$ | H | $OCH(CH_3)COOCH_3$ |
| 1-366 | F | Cl | Na | $CH_3$ | H | $OCH(CH_3)COOC_2H_5$ |
| 1-367 | F | Cl | Na | $CH_3$ | H | $OCH(CH_3)COOC_3H_7$ |
| 1-368 | F | Cl | Na | $CH_3$ | H | $OCH(CH_3)COOC_4H_9$ |
| 1-369 | F | Cl | Na | $CH_3$ | H | $OCH(CH_3)COOC_5H_{11}$ |
| 1-370 | F | Cl | Na | $CH_3$ | H | $SCH_2COOCH_3$ |
| 1-371 | F | Cl | Na | $CH_3$ | H | $SCH_2COOC_2H_5$ |
| 1-372 | F | Cl | Na | $CH_3$ | H | $SCH_2COOC_3H_7$ |
| 1-373 | F | Cl | Na | $CH_3$ | H | $SCH_2COOC_4H_9$ |
| 1-374 | F | Cl | Na | $CH_3$ | H | $SCH_2COOC_5H_{11}$ |
| 1-375 | F | Cl | Na | $CH_3$ | H | $SCH_2COO\text{-}c\text{-}C_5H_9$ |
| 1-376 | F | Cl | Na | $CH_3$ | H | $SCH_2COO\text{-}c\text{-}C_6H_{11}$ |
| 1-377 | F | Cl | Na | $CH_3$ | H | $SCH(CH_3)COO\text{-}c\text{-}C_5H_9$ |
| 1-378 | F | Cl | Na | $CH_3$ | H | $SCH(CH_3)COOCH_3$ |
| 1-379 | F | Cl | Na | $CH_3$ | H | $SCH(CH_3)COOC_2H_5$ |
| 1-380 | F | Cl | Na | $CH_3$ | H | $SCH(CH_3)COOC_3H_7$ |
| 1-381 | F | Cl | Na | $CH_3$ | H | $SCH(CH_3)COOC_4H_9$ |
| 1-382 | F | Cl | Na | $CH_3$ | H | $SCH(CH_3)COOC_5H_{11}$ |
| 1-383 | F | Cl | Na | $CH_3$ | H | $COOCH_3$ |
| 1-384 | F | Cl | Na | $CH_3$ | H | $COOC_2H_5$ |
| 1-385 | F | Cl | Na | $CH_3$ | H | $COOC_3H_7$ |
| 1-386 | F | Cl | Na | $CH_3$ | H | $COOC_4H_9$ |
| 1-387 | F | Cl | Na | $CH_3$ | H | $COOCH(CH_3)_2$ |
| 1-388 | F | Cl | K | $CH_3$ | H | H |
| 1-389 | F | Cl | K | $CH_3$ | H | OH |
| 1-390 | F | Cl | K | $CH_3$ | H | $OCH_3$ |

TABLE 16

| Compound | X | Y | M | $R^2$ | $R^3$ | B |
|---|---|---|---|---|---|---|
| 1-391 | F | Cl | K | $CH_3$ | H | $OC_2H_5$ |
| 1-392 | F | Cl | K | $CH_3$ | H | $OCH(CH_3)_2$ |
| 1-393 | F | Cl | K | $CH_3$ | H | $OCH_2C{\equiv}CH$ |
| 1-394 | F | Cl | K | $CH_3$ | H | $OCH(CH_3)C{\equiv}CH$ |
| 1-395 | F | Cl | K | $CH_3$ | H | $OCH_2COOCH_3$ |
| 1-396 | F | Cl | K | $CH_3$ | H | $OCH_2COOC_2H_5$ |
| 1-397 | F | Cl | K | $CH_3$ | H | $OCH_2COOC_3H_7$ |
| 1-398 | F | Cl | K | $CH_3$ | H | $OCH_2COOC_4H_9$ |
| 1-399 | F | Cl | K | $CH_3$ | H | $OCH_2COOC_5H_{11}$ |
| 1-400 | F | Cl | K | $CH_3$ | H | $OCH(CH_3)COOCH_3$ |
| 1-401 | F | Cl | K | $CH_3$ | H | $OCH(CH_3)COOC_2H_5$ |
| 1-402 | F | Cl | K | $CH_3$ | H | $OCH(CH_3)COOC_3H_7$ |
| 1-403 | F | Cl | K | $CH_3$ | H | $OCH(CH_3)COOC_4H_9$ |
| 1-404 | F | Cl | K | $CH_3$ | H | $OCH(CH_3)COOC_5H_{11}$ |
| 1-405 | F | Cl | K | $CH_3$ | H | $SCH_2COOCH_3$ |
| 1-406 | F | Cl | K | $CH_3$ | H | $SCH_2COOC_2H_5$ |
| 1-407 | F | Cl | K | $CH_3$ | H | $SCH_2COOC_3H_7$ |
| 1-408 | F | Cl | K | $CH_3$ | H | $SCH_2COOC_4H_9$ |
| 1-409 | F | Cl | K | $CH_3$ | H | $SCH_2COOC_5H_{11}$ |
| 1-410 | F | Cl | K | $CH_3$ | H | $SCH_2COO\text{-}c\text{-}C_5H_9$ |
| 1-411 | F | Cl | K | $CH_3$ | H | $SCH_2COO\text{-}c\text{-}C_6H_{11}$ |
| 1-412 | F | Cl | K | $CH_3$ | H | $SCH(CH_3)COO\text{-}c\text{-}C_5H_9$ |
| 1-413 | F | Cl | K | $CH_3$ | H | $SCH(CH_3)COOCH_3$ |
| 1-414 | F | Cl | K | $CH_3$ | H | $SCH(CH_3)COOC_2H_5$ |
| 1-415 | F | Cl | K | $CH_3$ | H | $SCH(CH_3)COOC_3H_7$ |
| 1-416 | F | Cl | K | $CH_3$ | H | $SCH(CH_3)COOC_4H_9$ |

TABLE 17

| Compound | X | Y | M | $R^2$ | $R^3$ | B |
|---|---|---|---|---|---|---|
| 1-417 | F | Cl | K | $CH_3$ | H | $SCH(CH_3)COOC_5H_{11}$ |
| 1-418 | F | Cl | K | $CH_3$ | H | $COOCH_3$ |
| 1-419 | F | Cl | K | $CH_3$ | H | $COOC_2H_5$ |
| 1-420 | F | Cl | K | $CH_3$ | H | $COOC_3H_7$ |
| 1-421 | F | Cl | K | $CH_3$ | H | $COOC_4H_9$ |
| 1-422 | F | Cl | K | $CH_3$ | H | $COOCH(CH_3)_2$ |
| 1-423 | F | Cl | $HNEt_3$ | $CH_3$ | H | H |
| 1-424 | F | Cl | $HNEt_3$ | $CH_3$ | H | OH |
| 1-425 | F | Cl | $HNEt_3$ | $CH_3$ | H | $OCH_3$ |
| 1-426 | F | Cl | $HNEt_3$ | $CH_3$ | H | $OC_2H_5$ |
| 1-427 | F | Cl | $HNEt_3$ | $CH_3$ | H | $OCH(CH_3)_2$ |
| 1-428 | F | Cl | $HNEt_3$ | $CH_3$ | H | $OCH_2C{\equiv}CH$ |
| 1-429 | F | Cl | $HNEt_3$ | $CH_3$ | H | $OCH(CH_3)C{\equiv}CH$ |
| 1-430 | F | Cl | $HNEt_3$ | $CH_3$ | H | $OCH_2COOCH_3$ |
| 1-431 | F | Cl | $HNEt_3$ | $CH_3$ | H | $OCH_2COOC_2H_5$ |
| 1-432 | F | Cl | $HNEt_3$ | $CH_3$ | H | $OCH_2COOC_3H_7$ |
| 1-433 | F | Cl | $HNEt_3$ | $CH_3$ | H | $OCH_2COOC_4H_9$ |
| 1-434 | F | Cl | $HNEt_3$ | $CH_3$ | H | $OCH_2COOC_5H_{11}$ |
| 1-435 | F | Cl | $HNEt_3$ | $CH_3$ | H | $OCH(CH_3)COOCH_3$ |
| 1-436 | F | Cl | $HNEt_3$ | $CH_3$ | H | $OCH(CH_3)COOC_2H_5$ |
| 1-437 | F | Cl | $HNEt_3$ | $CH_3$ | H | $OCH(CH_3)COOC_3H_7$ |
| 1-438 | F | Cl | $HNEt_3$ | $CH_3$ | H | $OCH(CH_3)COOC_4H_9$ |
| 1-439 | F | Cl | $HNEt_3$ | $CH_3$ | H | $OCH(CH_3)COOC_5H_{11}$ |
| 1-440 | F | Cl | $HNEt_3$ | $CH_3$ | H | $SCH_2COOCH_3$ |
| 1-441 | F | Cl | $HNEt_3$ | $CH_3$ | H | $SCH_2COOC_2H_5$ |
| 1-442 | F | Cl | $HNEt_3$ | $CH_3$ | H | $SCH_2COOC_3H_7$ |

TABLE 18

| Compound | X | Y | M | $R^2$ | $R^3$ | B |
|---|---|---|---|---|---|---|
| 1-443 | F | Cl | $HNEt_3$ | $CH_3$ | H | $SCH_2COOC_4H_9$ |
| 1-444 | F | Cl | $HNEt_3$ | $CH_3$ | H | $SCH_2COOC_5H_{11}$ |
| 1-445 | F | Cl | $HNEt_3$ | $CH_3$ | H | $SCH_2COO\text{-}c\text{-}C_5H_9$ |
| 1-446 | F | Cl | $HNEt_3$ | $CH_3$ | H | $SCH_2COO\text{-}c\text{-}C_6H_{11}$ |
| 1-447 | F | Cl | $HNEt_3$ | $CH_3$ | H | $SCH(CH_3)COO\text{-}c\text{-}C_5H_9$ |
| 1-448 | F | Cl | $HNEt_3$ | $CH_3$ | H | $SCH(CH_3)COOCH_3$ |
| 1-449 | F | Cl | $HNEt_3$ | $CH_3$ | H | $SCH(CH_3)COOC_2H_5$ |
| 1-450 | F | Cl | $HNEt_3$ | $CH_3$ | H | $SCH(CH_3)COOC_3H_7$ |
| 1-451 | F | Cl | $HNEt_3$ | $CH_3$ | H | $SCH(CH_3)COOC_4H_9$ |
| 1-452 | F | Cl | $HNEt_3$ | $CH_3$ | H | $SCH(CH_3)COOC_5H_{11}$ |
| 1-453 | F | Cl | $HNEt_3$ | $CH_3$ | H | $COOCH_3$ |
| 1-454 | F | Cl | $HNEt_3$ | $CH_3$ | H | $COOC_2H_5$ |
| 1-455 | F | Cl | $HNEt_3$ | $CH_3$ | H | $COOC_3H_7$ |
| 1-456 | F | Cl | $HNEt_3$ | $CH_3$ | H | $COOC_4H_9$ |
| 1-457 | F | Cl | $HNEt_3$ | $CH_3$ | H | $COOCH(CH_3)_2$ |
| 1-458 | F | Cl | $HNBu_3$ | $CH_3$ | H | H |
| 1-459 | F | Cl | $HNBu_3$ | $CH_3$ | H | OH |
| 1-460 | F | Cl | $HNBu_3$ | $CH_3$ | H | $OCH_3$ |
| 1-461 | F | Cl | $HNBu_3$ | $CH_3$ | H | $OC_2H_5$ |
| 1-462 | F | Cl | $HNBu_3$ | $CH_3$ | H | $OCH(CH_3)_2$ |
| 1-463 | F | Cl | $HNBu_3$ | $CH_3$ | H | $OCH_2C{\equiv}CH$ |
| 1-464 | F | Cl | $HNBu_3$ | $CH_3$ | H | $OCH(CH_3)C{\equiv}CH$ |
| 1-465 | F | Cl | $HNBu_3$ | $CH_3$ | H | $OCH_2COOCH_3$ |
| 1-466 | F | Cl | $HNBu_3$ | $CH_3$ | H | $OCH_2COOC_2H_5$ |
| 1-467 | F | Cl | $HNBu_3$ | $CH_3$ | H | $OCH_2COOC_3H_7$ |
| 1-468 | F | Cl | $HNBu_3$ | $CH_3$ | H | $OCH_2COOC_4H_9$ |

TABLE 19

| Compound | X | Y | M | $R^2$ | $R^3$ | B |
|---|---|---|---|---|---|---|
| 1-469 | F | Cl | $HNBu_3$ | $CH_3$ | H | $OCH_2COOC_5H_{11}$ |
| 1-470 | F | Cl | $HNBu_3$ | $CH_3$ | H | $OCH(CH_3)COOCH_3$ |
| 1-471 | F | Cl | $HNBu_3$ | $CH_3$ | H | $OCH(CH_3)COOC_2H_5$ |
| 1-472 | F | Cl | $HNBu_3$ | $CH_3$ | H | $OCH(CH_3)COOC_3H_7$ |
| 1-473 | F | Cl | $HNBu_3$ | $CH_3$ | H | $OCH(CH_3)COOC_4H_9$ |
| 1-474 | F | Cl | $HNBu_3$ | $CH_3$ | H | $OCH(CH_3)COOC_5H_{11}$ |

TABLE 19-continued

| Compound | X | Y | M | R² | R³ | B |
|---|---|---|---|---|---|---|
| 1-475 | F | Cl | HNBu₃ | CH₃ | H | SCH₂COOCH₃ |
| 1-476 | F | Cl | HNBu₃ | CH₃ | H | SCH₂COOC₂H₅ |
| 1-477 | F | Cl | HNBu₃ | CH₃ | H | SCH₂COOC₃H₇ |
| 1-478 | F | Cl | HNBu₃ | CH₃ | H | SCH₂COOC₄H₉ |
| 1-479 | F | Cl | HNBu₃ | CH₃ | H | SCH₂COOC₅H₁₁ |
| 1-480 | F | Cl | HNBu₃ | CH₃ | H | SCH₂COO-c-C₅H₉ |
| 1-481 | F | Cl | HNBu₃ | CH₃ | H | SCH₂COO-c-C₆H₁₁ |
| 1-482 | F | Cl | HNBu₃ | CH₃ | H | SCH(CH₃)COO-c-C₅H₉ |
| 1-483 | F | Cl | HNBu₃ | CH₃ | H | SCH(CH₃)COOCH₃ |
| 1-484 | F | Cl | HNBu₃ | CH₃ | H | SCH(CH₃)COOC₂H₅ |
| 1-485 | F | Cl | HNBu₃ | CH₃ | H | SCH(CH₃)COOC₃H₇ |
| 1-486 | F | Cl | HNBu₃ | CH₃ | H | SCH(CH₃)COOC₄H₉ |
| 1-487 | F | Cl | HNBu₃ | CH₃ | H | SCH(CH₃)COOC₅H₁₁ |
| 1-488 | F | Cl | HNBu₃ | CH₃ | H | COOCH₃ |
| 1-489 | F | Cl | HNBu₃ | CH₃ | H | COOC₂H₅ |
| 1-490 | F | Cl | HNBu₃ | CH₃ | H | COOC₃H₇ |
| 1-491 | F | Cl | HNBu₃ | CH₃ | H | COOC₄H₉ |
| 1-492 | F | Cl | HNBu₃ | CH₃ | H | COOCH(CH₃)₂ |
| 1-493 | F | Cl | HNC₅H₅ | H | H | OCH(CH₃)₂ |
| 1-494 | F | Cl | HNC₅H₅ | H | H | COOCH(CH₃)₂ |

TABLE 20

| Compound | X | Y | M | R² | R³ | B |
|---|---|---|---|---|---|---|
| 1-495 | F | Cl | HNC₅H₅ | CH₃ | H | OCH(CH₃)₂ |
| 1-496 | F | Cl | HNC₅H₅ | CH₃ | H | OH |
| 1-497 | F | Cl | H(CH₃)₂NC₆H₅ | H | H | OCH₂COOC₅H₁₁ |
| 1-498 | F | Cl | H(CH₃)₂NC₆H₅ | H | H | CH₂CHClCOOC₂H₅ |
| 1-499 | F | Cl | H(CH₃)₂NC₆H₅ | CH₃ | H | SCH₂COO-c-C₅H₉ |
| 1-500 | F | Cl | Li | CH₃ | H | OCH(CH₃)₂ |
| 1-501 | F | Cl | Li | CH₃ | H | OCOOCH₃ |
| 1-502 | F | Cl | Li | CH₃ | H | OCOOC₂H₅ |
| 1-503 | F | Cl | Li | CH₃ | H | OCOOC₃H₇ |
| 1-504 | F | Cl | Li | CH₃ | H | OCOOC₄H₉ |
| 1-505 | F | Cl | Li | CH₃ | H | OH |

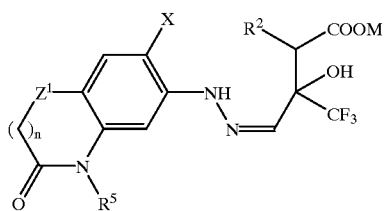

TABLE 21

| Compound | X | Z¹ | M | n | R² | R⁵ |
|---|---|---|---|---|---|---|
| 2-1 | F | O | H | 1 | CH₃ | CH₂C≡CH |
| 2-2 | F | O | H | 1 | CH₃ | CH(CH₃)C≡CH |
| 2-3 | F | O | H | 1 | CH₃ | CH₂COOCH₃ |
| 2-4 | F | O | H | 1 | CH₃ | CH₂COOC₂H₅ |
| 2-5 | F | O | H | 1 | CH₃ | CH(CH₃)COOC₂H₅ |
| 2-6 | F | O | H | 1 | CH₃ | CH₂CN |
| 2-7 | F | O | H | 1 | CH₃ | CH(CH₃)₂ |
| 2-8 | F | O | H | 1 | CH₃ | CH(CH₃)C₂H₅ |
| 2-9 | F | O | H | 1 | H | CH₂C≡CH |
| 2-10 | F | O | H | 1 | H | CH(CH₃)C≡CH |
| 2-11 | F | O | H | 1 | H | CH₂COOCH₃ |
| 2-12 | F | O | H | 1 | H | CH₂COOC₂H₅ |
| 2-13 | F | O | H | 1 | H | CH(CH₃)COOC₂H₅ |
| 2-14 | F | O | H | 1 | H | CH₂CN |

TABLE 21-continued

| Compound | X | Z¹ | M | n | R² | R⁵ |
|---|---|---|---|---|---|---|
| 2-15 | F | O | H | 1 | H | CH(CH₃)₂ |
| 2-16 | F | O | H | 1 | H | CH(CH₃)C₂H₅ |
| 2-17 | H | O | H | 1 | CH₃ | CH₂C≡CH |
| 2-18 | H | O | H | 1 | CH₃ | CH(CH₃)C≡CH |
| 2-19 | H | O | H | 1 | CH₃ | CH₂COOCH₃ |
| 2-20 | H | O | H | 1 | CH₃ | CH₂COOC₂H₅ |
| 2-21 | H | O | H | 1 | CH₃ | CH(CH₃)COOC₂H₅ |
| 2-22 | H | O | H | 1 | CH₃ | CH₂CN |
| 2-23 | H | O | H | 1 | CH₃ | CH(CH₃)₂ |
| 2-24 | H | O | H | 1 | CH₃ | CH(CH₃)C₂H₅ |
| 2-25 | H | O | H | 1 | H | CH₂C≡CH |
| 2-26 | H | O | H | 1 | H | CH(CH₃)C≡CH |

TABLE 22

| Compound | X | Z¹ | M | n | R² | R⁵ |
|---|---|---|---|---|---|---|
| 2-27 | H | O | H | 1 | H | CH₂COOCH₃ |
| 2-28 | H | O | H | 1 | H | CH₂COOC₂H₅ |
| 2-29 | H | O | H | 1 | H | CH(CH₃)COOC₂H₅ |
| 2-30 | H | O | H | 1 | H | CH₂CN |
| 2-31 | H | O | H | 1 | H | CH(CH₃)₂ |
| 2-32 | H | O | H | 1 | H | CH(CH₃)C₂H₅ |
| 2-33 | F | S | H | 0 | CH₃ | CH₂C≡CH |
| 2-34 | F | S | H | 0 | CH₃ | CH(CH₃)C≡CH |
| 2-35 | F | S | H | 0 | CH₃ | CH₂COOCH₃ |
| 2-36 | F | S | H | 0 | CH₃ | CH₂COOC₂H₅ |
| 2-37 | F | S | H | 0 | CH₃ | CH(CH₃)COOC₂H₅ |
| 2-38 | F | S | H | 0 | CH₃ | CH₂CN |
| 2-39 | F | S | H | 0 | CH₃ | CH(CH₃)₂ |
| 2-40 | F | S | H | 0 | CH₃ | CH(CH₃)C₂H₅ |
| 2-41 | F | S | H | 0 | H | CH₂C≡CH |
| 2-42 | F | S | H | 0 | H | CH(CH₃)C≡CH |
| 2-43 | F | S | H | 0 | H | CH₂COOCH₃ |
| 2-44 | F | S | H | 0 | H | CH₂COOC₂H₅ |
| 2-45 | F | S | H | 0 | H | CH(CH₃)COOC₂H₅ |
| 2-46 | F | S | H | 0 | H | CH₂CN |
| 2-47 | F | S | H | 0 | H | CH(CH₃)₂ |
| 2-48 | F | S | H | 0 | H | CH(CH₃)C₂H₅ |
| 2-49 | F | O | HNEt₃ | 1 | CH₃ | CH₂C≡CH |
| 2-50 | F | S | HNEt₃ | 0 | H | CH₂C≡CH |

Hydrazone compounds of formula (5):

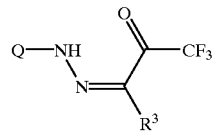

TABLE 23

| Compound | Q | X | Y | B | R³ |
|---|---|---|---|---|---|
| 3-1 | Q-1 | F | Cl | OH | H |
| 3-2 | Q-1 | F | Cl | H | H |
| 3-3 | Q-1 | F | Cl | OCH(CH₃)₂ | H |
| 3-4 | Q-1 | F | Cl | OCH₂C≡CH | H |
| 3-5 | Q-1 | F | Cl | OCH(CH₃)C≡CH | H |
| 3-6 | Q-1 | F | Cl | OCH₂COOH | H |
| 3-7 | Q-1 | F | Cl | OCH₂COOCH₃ | H |
| 3-8 | Q-1 | F | Cl | OCH₂COOC₂H₅ | H |
| 3-9 | Q-1 | F | Cl | COOCH₃ | H |
| 3-10 | Q-1 | F | Cl | COOC₂H₅ | H |
| 3-11 | Q-1 | H | Cl | H | H |

TABLE 23-continued

| Compound | Q | X | Y | B | R³ |
|---|---|---|---|---|---|
| 3-12 | Q-1 | H | Cl | OCH(CH₃)₂ | H |
| 3-13 | Q-1 | Cl | Cl | OCH(CH₃)₂ | H |

Malonic acid derivatives of formula (6):

R²CH(COOH)₂

TABLE 24

| Compound | R² |
|---|---|
| 4-1 | H |
| 4-2 | CH₃ |
| 4-3 | C₂H₅ |

The following illustrates the process for producing pyridazin-3-one derivatives of formula (7) from the present compounds, which process is hereinafter referred to as process 2.

Process 2 can be carried out under various reaction conditions. Among these conditions there are some typical examples described below for seven different processes 2-1, 2-2, 2-3, 2-4, 2-5, 2-6 and 2-7.

The present compounds may be used as the starting material compounds in process 2; however, depending upon the reaction conditions, for example, under those described in process 2-3 or 2-4, the reaction can be effected as the present compounds are formed from their salts in the reaction system.

1) Process 2-1

The present compounds are ring closed under heating conditions to produce pyridazin-3-one derivatives of formula (7).

The reaction is usually effected without solvent or in a solvent. The reaction temperature is usually in the range of 80° to 250° C., preferably 120° to 160° C. The reaction time is usually in the range of a moment to 72 hours.

Examples of the solvent used in the reaction may include aliphatic hydrocarbons such as heptane, octane and ligroin; aromatic hydrocarbons such as benzene, toluene, ethylbenzene, xylene and mesitylene; halogenated hydrocarbons such as 1,2-dichloroethane, chlorobenzene, dichlorobenzene, trichlorobenzene and benzotrifluoride; ethers such as 1,4-dioxane, ethylene glycol dimethyl ether and methyl t-butyl ether; ketones such as methyl isobutyl ketone and cyclohexanone; acid amides such as N,N-dimethylformamide; alcohols such as propanol, butanol, amyl alcohol, ethylene glycol and diethylene glycol; and mixtures thereof.

After completion of the reaction, the reaction mixture is directly concentrated or subjected to post-treatments that the reaction mixture is poured into water, which is then extracted with an organic solvent, and the organic layer is dried and concentrated. If necessary, purification is subsequently carried out by a technique such as chromatography or recrystallization. Thus, the pyridazin-3-one derivatives of formula (7) can be obtained.

2) Process 2-2

The present compounds are ring closed in the presence of a base to produce pyridazin-3-one derivatives of formula (7).

Examples of the base used in the reaction may include nitrogen-containing aromatic compounds such as pyridine, quinoline, isoquinoline, 4-dimethylaminopyridine, 2-picoline, 3-picoline, 4-picoline, 2,3-lutidine, 2,4-lutidine, 2,5-lutidine, 2,6-lutidine, 3,4-lutidine, 3,5-lutidine, 3-chloropyridine, 2-ethyl-3-methylpyridine and 5-ethyl-2-methylpyridine; dialkylaniline derivatives such as N,N-dimethylaniline and N,N-diethylaniline; and tertiary amines such as triethylamine, diisopropylethylamine, tri-n-propylamine, tri-n-butylamine, benzyldimethylamine, phenethyldimethylamine, N-methylmorpholine, 1,8-diazabicyclo[5.4.0]undec-7-ene, 1,5-diazabicyclo[4.3.0] non-5-ene and 1,4-diazabicyclo[2.2.2]octane. Preferred are trialkylamines such as triethylamine, diisopropylethylamine, tri-n-propylamine and tri-n-butylamine; and pyridine compounds optionally substituted with alkyl, such as pyridine, 2-picoline, 3-picoline, 4-picoline, 2,3-lutidine, 2,4-lutidine, 2,5-lutidine, 2,6-lutidine, 3,4-lutidine, 3,5-lutidine, 2-ethyl-3-methylpyridine and 5-ethyl-2-methylpyridine.

The amount of base to be used is usually a catalytic amount to a larger excess, preferably a catalytic amount to 10 moles, for each one mole of the present compound. The reaction temperature may vary depending upon the base used, and is usually in the range of 80° to 250° C., preferably 120° to 160° C. The reaction time is usually in the range of a moment to 72 hours.

The reaction is usually effected in a solvent or without solvent. Examples of the solvent used in the reaction may include aliphatic hydrocarbons such as hexane, heptane, octane and ligroin; aromatic hydrocarbons such as benzene, toluene, ethylbenzene, xylene and mesitylene; halogenated hydrocarbons such as chlorobenzene, dichlorobenzene, trichlorobenzene and benzotrifluoride; ethers such as 1,4-dioxane, tetrahydrofuran, ethylene glycol dimethyl ether and methyl t-butyl ether; ketones such as methyl isobutyl ketone and cyclohexanone; acid amides such as N,N-dimethylformamide; alcohols such as ethanol, propanol, butanol, amyl alcohol, ethylene glycol and diethylene glycol; and mixtures thereof.

After completion of the reaction, the reaction mixture is directly concentrated or subjected to post-treatments that the reaction mixture is poured into water, which is then extracted with an organic solvent, and the organic layer is dried and concentrated. If necessary, purification is subsequently carried out by a technique such as chromatography or recrystallization. Thus, the pyridazin-3-one derivatives of formula (7) can be obtained.

The reaction can also be effected under dehydration from the reaction system, for example, with a desiccant such as molecular sieve.

3) Process 2-3

The present compounds are ring closed in the presence of an acid to produce pyridazin-3-one derivatives of formula (7).

Examples of the acid used in the reaction may include organic acids such as fatty acids, e.g., acetic acid, propionic acid, trimethylacetic acid, chloroacetic acid, trifluoroacetic acid, phenylacetic acid, butyric acid, isobutyric acid, valeric acid, isovaleric acid; benzoic acid and derivatives, e.g., 4-nitrobenzoic acid, 4-chlorobenzoic acid, 3,5-dinitrobenzoic acid, 4-methoxybenzoic acid; and sulfonic acids, e.g., p-toluenesulfonic acid, benzenesulfonic acid, methanesulfonic acid, trifluoromethanesulfonic acid; inorganic acids such as sulfuric acid, hydrochloric acid and phosphoric acid; and acidic type cation exchange resins such as Amberlite CG-50 and Amberlite IR-120.

The amount of acid to be used in the reaction is usually a catalytic amount to a larger excess, preferably a catalytic amount to 10 moles, for each one mole of the present compound. The reaction temperature may vary depending upon the acid used, and is usually in the range of 50° to 250° C. The reaction time is usually in the range of a moment to 72 hours.

The reaction is usually effected without solvent or in a solvent. Examples of the solvent used in the reaction may include aliphatic hydrocarbons such as hexane, heptane, octane and ligroin; aromatic hydrocarbons such as benzene, toluene, ethylbenzene, xylene and mesitylene; halogenated hydrocarbons such as dichloromethane, chloroform, carbon tetrachloride, 1,2-dichloroethane, chlorobenzene, dichlorobenzene, trichlorobenzene and benzotrifluoride; ethers such as 1,4-dioxane, tetrahydrofuran, ethylene glycol dimethyl ether and methyl t-butyl ether; ketones such as methyl isobutyl ketone and cyclohexanone; and mixtures thereof.

After completion of the reaction, the reaction mixture is directly concentrated or subjected to post-treatments that the reaction mixture is poured into water, which is then extracted with an organic solvent, and the organic layer is dried and concentrated. If necessary, purification is subsequently carried out by a technique such as chromatography or recrystallization. Thus, the pyridazin-3-one derivatives of formula (7) can be obtained. When an acidic type cation exchange resin is used, the above post-treatments are carried out after the removal of the acidic type cation exchange resin by filtration.

4) Process 2-4

The present compounds are ring closed in the presence of at least one acid and at least one base to produce pyridazin-3-one derivatives of formula (7).

Examples of the acid used in the reaction may include organic acids such as fatty acids, e.g., acetic acid, propionic acid, trimethylacetic acid, trichloroacetic acid, trifluoroacetic acid, phenylacetic acid, butyric acid, isobutyric acid, valeric acid, isovaleric acid; benzoic acid and derivatives thereof, e.g., 4-nitrobenzoic acid, 4-chlorobenzoic acid, 3,5-dinitrobenzoic acid, 4-methoxybenzoic acid; and sulfonic acids, e.g., p-toluenesulfonic acid, methanesulfonic acid, trifluoromethanesulfonic acid; and inorganic acids such as sulfuric acid, hydrochloric acid and phosphoric acid.

Examples of the base used in the reaction may include nitrogen-containing aromatic compounds such as pyridine, quinoline, 4-dimethylaminopyridine, 2-picoline, 3-picoline, 4-picoline, 2,3-lutidine, 2,4-lutidine, 2,5-lutidine, 2,6-lutidine, 3,4-lutidine, 3,5-lutidine, 3-chloropyridine, 2-ethyl-3-methylpyridine and 5-ethyl-2-methylpyridine; dialkylaniline derivatives such as N,N-dimethylaniline and N,N-diethylaniline; secondary amines such as piperidine, pyrrolidine, morpholine and diethylamine; tertiary amines such as triethylamine, diisopropylethylamine, tri-n-propylamine, tri-n-butylamine, benzyldimethylamine, phenethyldimethylamine, N-methylmorpholine, 1,8-diazabicyclo[5.4.0]-undec-7-ene, 1,5-diazabicyclo[4.3.0]non-5-ene and 1,4-diazabicyclo[2.2.2]octane; inorganic bases such as lithium hydroxide, sodium hydroxide and potassium hydroxide; and ammonia.

The reaction can be effected with any combination of these acids and bases; however, preferred combinations of acids and bases are those of fatty acids, e.g., acetic acid, propionic acid, trimethylacetic acid, chloroacetic acid, trifluoroacetic acid, phenylacetic acid, or benzoic acid or derivatives thereof, e.g., 4-nitrobenzoic acid, 4-chlorobenzoic acid, 3,5-dinitrobenzoic acid, 4-methoxybenzoic acid, and nitrogen-containing compounds, e.g., pyridine, quinoline, 4-dimethylaminopyridine, 2-picoline, 3-picoline, 4-picoline, 2,3-lutidine, 2,4-lutidine, 2,5-lutidine, 2,6-lutidine, 3,4-lutidine, 3,5-lutidine, 3-chloropyridine, 2-ethyl-3-methylpyridine, 5-ethyl-2-methylpyridine, or tertiary amines, e.g., triethylamine, diisopropylethylamine, tri-n-propylamine, tri-n-butylamine, benzyldimethylamine, phenethyldimethylamine, N-methylmorpholine, 1,8-diazabicyclo[5.4.0]-undec-7-ene, 1,5-diazabicyclo[4.3.0]non-5-ene, 1,4-diazabicyclo[2.2.2]octane.

The amount of acid to be used in the reaction is usually a catalytic amount to a larger excess for each one mole of the present compound. The amount of base used in the reaction is usually a catalytic amount to a larger excess for each one mole of the present compound.

The reaction can also be effected by use of salts obtained from acids and bases. Typical examples of the salt may include salts obtained from the above preferred acids and the above preferred bases, such as sodium, potassium and ammonium salts of fatty acids, e.g., acetic acid, propionic acid, pivalic acid, trifluoroacetic acid, phenylacetic acid; sodium, potassium and ammonium salts of benzoic acid or derivatives thereof, e.g., 4-nitrobenzoic acid, 4-chlorobenzoic acid, 3,5-dinitrobenzoic acid, 4-methoxybenzoic acid; hydrochloride and sulfate salts of nitrogen-containing compounds, e.g., pyridine, quinoline, 4-dimethylaminopyridine, 2-picoline, 3-picoline, 4-picoline, 2,3-lutidine, 2,4-lutidine, 2,5-lutidine, 2,6-lutidine, 3,4-lutidine, 3,5-lutidine, 3-chloropyridine, 2-ethyl-3-methylpyridine, 5-ethyl-2-methylpyridine; hydrochloride and sulfate salts of tertiary amines, e.g., triethylamine, diisopropylethylamine, tri-n-propylamine, tri-n-butylamine, benzyldimethylamine, phenethyldimethylamine, N-methylmorpholine; ammonium chloride and ammonium sulfate.

The reaction time is usually in the range of an moment to 72 hours. The reaction temperature may vary depending upon the acid and base used, and is usually in the range of 80° to 250° C.

The reaction is usually effected without solvent or in a solvent. Examples of the solvent used in the reaction may include aliphatic hydrocarbons such as hexane, heptane, octane and ligroin; aromatic hydrocarbons such as benzene, toluene, ethylbenzene, xylene and mesitylene; halogenated hydrocarbons such as chlorobenzene, dichlorobenzene, trichlorobenzene and benzotrifluoride; ethers such as 1,4-dioxane, tetrahydrofuran, ethylene glycol dimethyl ether and methyl t-butyl ether; acid amides such as N,N-dimethylformamide; alcohols such as ethanol, propanol, butanol, amyl alcohol, ethylene glycol and diethylene glycol; and mixtures thereof. In addition, ketones such as methyl isobutyl ketone and cyclohexanone can also be used as the solvent; however, when secondary amines are used as the base, it is not preferred to use such ketones as the solvent.

After completion of the reaction, the reaction mixture is directly concentrated or subjected to post-treatments that the reaction mixture is poured into water, which is then extracted with an organic solvent, and the organic layer is dried and concentrated. If necessary, purification is subsequently carried out by a technique such as chromatography or recrystallization. Thus, the pyridazin-3-one derivatives of formula (7) can be obtained.

The reaction can also be effected under dehydration from the reaction system, for example, with a desiccant such as molecular sieve.

5) Process 2-5

The present compounds are reacted with haloformic acid esters in the presence of a base to produce pyridazin-3-one derivatives of formula (7).

Examples of the haloformic acid ester used in the reaction may include methyl chloroformate, ethyl chloroformate, propyl chloroformate and methyl bromoformate.

Examples of the base used in the reaction may include organic bases, e.g., nitrogen-containing aromatic compounds such as pyridine, quinoline, 4-dimethylaminopyridine, 2-picoline, 3-picoline, 4-picoline, 2,3-lutidine, 2,4-lutidine, 2,5-lutidine, 2,6-lutidine, 3,4-lutidine, 3,5-lutidine, 3-chloropyridine, 2-ethyl-3-methylpyridine and 5-ethyl-2-methylpyridine; dialkylaniline derivatives such as N,N-dimethylaniline and N,N-diethylaniline; and tertiary amines such as triethylamine, diisopropylethylamine, tri-n-propylamine, tri-n-butylamine, benzyldimethylamine, phenethyldimethylamine, N-methylmorpholine, 1,8-diazabicyclo[5.4.0]undec-7-ene, 1,5-diazabicyclo[4.3.0]non-5-ene and 1,4-diazabicyclo[2.2.2]octane.

The amounts of reagents to be used in the reaction are usually 1 to 10 moles of the haloformic acid ester and usually 1 to 20 moles of the base, for each one mole of the present compound. The reaction time is usually in the range of a moment to 72 hours. The reaction temperature is usually in the range of −20° to 100° C.

The reaction is usually effected without solvent or in a solvent. Examples of the solvent used in the reaction may include aliphatic hydrocarbons such as hexane, heptane, octane and ligroin; aromatic hydrocarbons such as benzene, toluene, ethylbenzene, xylene and mesitylene; halogenated hydrocarbons such as dichloromethane, chloroform, carbon tetrachloride, 1,2-dichloroethane, chlorobenzene, dichlorobenzene, trichlorobenzene and benzotrifluoride; ethers such as 1,4-dioxane, tetrahydrofuran, ethylene glycol dimethyl ether and methyl t-butyl ether; and mixtures thereof.

After completion of the reaction, the reaction mixture is directly concentrated or subjected to post-treatments that the reaction mixture is poured into water, which is then extracted with an organic solvent, and the organic layer is dried and concentrated. If necessary, purification is subsequently carried out by a technique such as chromatography or recrystallization. Thus, the pyridazin-3-one derivatives of formula (7) can be obtained.

6) Process 2-6

The present compounds are reacted with condensing agents in the presence of a base to produce pyridazin-3-one derivatives of formula (7).

Examples of the condensing agent used in the reaction may include 1,3-di-cyclohexylcarbodiimide, 1-ethyl-3-(3'-dimethylaminopropyl)carbodiimide, diethylphosphoric cyanide, acetic anhydride and acetyl chloride.

Examples of the base used in the reaction may include organic bases, e.g., nitrogen-containing aromatic compounds such as pyridine and 4-dimethylaminopyridine; and tertiary amines such as triethylamine, diisopropylethylamine and tri-n-butylanine.

The amounts of reagents to be used in the reaction are usually 1 to 10 moles of the condensing agent and usually 1 to 20 moles of the base, for each one mole of the present compound.

The reaction time is usually in the range of a moment to 72 hours. The reaction temperature is usually in the range of −20° to 150° C.

The reaction is usually effected without solvent or in a solvent. Examples of the solvent used in the reaction may include aliphatic hydrocarbons such as hexane, heptane, octane and ligroin; aromatic hydrocarbons such as benzene, toluene, ethyl-benzene, xylene and mesitylene; halogenated hydrocarbons such as dichloromethane, chloroform, carbon tetrachloride, 1,2-dichloroethane, chlorobenzene, dichlorobenzene, trichlorobenzene and benzotrifluoride; ethers such as 1,4-dioxane, tetrahydrofuran, ethylene glycol dimethyl ether and methyl t-butyl ether; and mixtures thereof.

After completion of the reaction, the reaction mixture is directly concentrated or subjected to post-treatments that the reaction mixture is poured into water, which is then extracted with an organic solvent, and the organic layer is dried and concentrated. If necessary, purification is subsequently carried out by a technique such as chromatography or recrystallization. Thus, the pyridazin-3-one derivatives of formula (7) can be obtained.

7) Process 2-7

The present compounds are reacted with halogenating agents in the presence of a base to produce pyridazin-3-one derivatives of formula (7).

Examples of the halogenating agent used in the reaction may include thionyl chloride, phosgene, oxalyl chloride, phosphorous trichloride, phosphorus pentachloride and phosphorus oxychloride.

Examples of the base used in the reaction may include organic bases, e.g., nitrogen-containing aromatic compounds such as pyridine, quinoline, 4-dimethylaminopyridine, 2-picoline, 3-picoline, 4-picoline, 2,3-lutidine, 2,4-lutidine, 2,5-lutidine, 2,6-lutidine, 3,4-lutidine, 3,5-lutidine, 3-chloropyridine, 2-ethyl-3-methylpyridine and 5-ethyl-2-methylpyridine; dialkylaniline derivatives such as N,N-dimethylaniline and N,N-diethylaniline; and tertiary amines such as triethylamine, diisopropylethylamine, tri-n-propylamine, tri-n-butylamine, benzyldimethylamine, phenethyldimethylamine, N-methylmorpholine, 1,8-diazabicyclo[5.4.0]undec-7-ene, 1,5-diazabicyclo[4.3.0]non-5-ene and 1,4-diazabicyclo[2.2.2]octane.

The amounts of reagents to be used in the reaction are usually 1 to 10 moles of the halogenating agent and usually 1 to 20 moles of the base, for each one mole of the present compound.

The reaction time is usually in the range of a moment to 72 hours. The reaction temperature is usually in the range of −20° to 150° C.

The reaction is usually effected without solvent or in a solvent. Examples of the solvent used in the reaction may include aliphatic hydrocarbons such as hexane, heptane, octane and ligroin; aromatic hydrocarbons such as benzene, toluene, ethyl-benzene, xylene and mesitylene; halogenated hydrocarbons such as dichloromethane, chloroform, carbon tetrachloride, 1,2-dichloroethane, chlorobenzene, dichlorobenzene, trichlorobenzene and benzotrifluoride; ethers such as 1,4-dioxane, tetrahydrofuran, ethylene glycol dimethyl ether and methyl t-butyl ether; and mixtures thereof.

The reaction can also be effected with the addition of N,N-dimethylformamide in a catalytic amount.

After completion of the reaction, the reaction mixture is directly concentrated or subjected to post-treatments that the reaction mixture is poured into water, which is then extracted with an organic solvent, and the organic layer is dried and concentrated. If necessary, purification is subsequently carried out by a technique such as chromatography or recrystallization. Thus, the pyridazin-3-one derivatives of formula (7) can be obtained.

When process 2-2 or 2-4 is conducted, the present compounds obtained in process 1 can also be directly subjected to process 2 without isolation.

In this case, the pyridazin-3-one derivatives of formula (7) can be obtained by reacting hydrazone compounds of formula (5) and malonic acid derivatives of formula (6) with the procedures described in process 1-1 or 1-2 to produce the present compounds, and 1) subsequently effecting the reaction under the conditions described in process 2-2; or
2) adding an acid as exemplified in process 2-4 to the reaction mixture and then effecting the reaction under the conditions described in process 2-4.

In process 2, depending upon the conditions, the formation of a pyridazin-3-one ring may be accompanied by the replacement of a substituent on the benzene ring. For example, when the present compounds of formula (1) wherein Q is Q-1, B is OR$^1$, and R$^1$ is C$_1$–C$_6$ alkyl are used in process 2-3, the pyridazin-3-one derivatives of formula (7) wherein Q is Q-1 and B is OH may be obtained.

Examples of the compounds which can be produced by process 2 are shown in Table 25.

Compounds of formula (25):

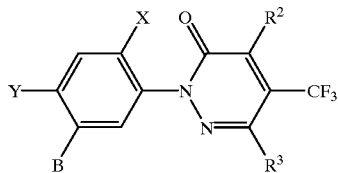

TABLE 25

| Compound | X | Y | B | R$^2$ | R$^3$ |
|---|---|---|---|---|---|
| 5-1 | F | Cl | OH | CH$_3$ | H |
| 5-2 | F | Cl | OCH(CH$_3$)$_2$ | CH$_3$ | H |
| 5-3 | F | Cl | OCH$_2$C≡CH | CH$_3$ | H |
| 5-4 | F | Cl | OCH(CH$_3$)C≡CH | CH$_3$ | H |
| 5-5 | F | Cl | OCH$_2$COOCH$_3$ | CH$_3$ | H |
| 5-6 | F | Cl | OCH$_2$COOC$_2$H$_5$ | CH$_3$ | H |
| 5-7 | F | Cl | COOCH$_3$ | CH$_3$ | H |
| 5-8 | F | Cl | COOC$_2$H$_5$ | CH$_3$ | H |
| 5-9 | F | Cl | OCH(CH$_3$)$_2$ | C$_2$H$_5$ | H |
| 5-10 | F | Cl | OCH(CH$_3$)$_2$ | H | H |
| 5-11 | F | Cl | OCH$_2$COOH | CH$_3$ | H |
| 5-12 | H | Cl | H | CH$_3$ | H |

The pyridazin-3-one derivatives of formula (7) have excellent herbicidal activity in the foliar and soil treatments on upland fields, for example, against various unfavorable weeds as described below.

Polygonaceae:
  wild buckwheat (*Polygonum convolvulus*), pale smartweed (*Polygonum lapathiolium*), Pennsylvania smartweed (*Polygonum pensylvanicum*), ladysthumb (*Polygonum persicaria*), curly dock (*Rumex crispus*), broadleaf dock (*Rumex obtusifolius*), Japanese knotweed (*Polygonum cuspidatum*)
Portulacaceae:
  common purslane (*Portulaca oleracea*)
Caryophyllaceae:
  common chickweed (*Stellaria media*)
Chenopodiaceae:
  common lambsquarters (*Chenopodium album*), kochia (*Kochia scoparia*)
Amaranthaceae:
  redroot pigweed (*Amaranthus retroflexus*), smooth pigweed (*Amaranthus hybridus*)
Cruciferae:
  wild radish (*Raphanus raphanistrium*), wild mustard (*Sinapis arvensis*), shepherdspurse (*Capsella bursapastoris*)
Leguminosae:
  hemp sesbania (*Sesbania exaltata*), sicklepod (*Cassia obtusifolia*), Florida beggarweed (*Desmodium tortuosum*), white clover (*Trifolium repens*)
Malvaceae:
  velvetleaf (*Abutilon theophrasti*), prickly sida (*Sida spinosa*)
Violaceae:
  field pansy (*Viola arvensis*), wild pansy (*Viola tricolor*)
Rubiaceae:
  catchweed bedstraw (cleavers) (*Galium aparine*)
Convolvulaceae:
  ivyleaf morningglory (*Ipomoea hederacea*), tall morningglory (*Ipomoea purpurea*), entireleaf momningglory (*Ipomoea hederacea* var. *integriuscuila*), pitted morningglory (*Ipomoea lacunosa*), field bindweed (*Convolvulus arvensis*)
Labiatae:
  red deadnettle (*Lamium purpureuim*), henbit (*Lamiuim amplexicaule*)
Solanaceae:
  jimsonweed (*Datura stramoniuim*), black nightshade (*Solanum nigrum*)
Scrophulariaceae:
  birdseye speedwell (*Veronica persica*), ivyleaf speedwell (*Veronica hederaefolia*)
Compositae:
  common cocklebur (*Xanthiuim pensylvanicuim*), common sunflower (*Helianthus annuus*), scentless chamomile (*Matricaria perforata* or *inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*), Japanese mugwort (*Artemisia princeps*), tall goldenrod (*Solidago altissima*)
Boraginaceae:
  field forget-me-not (*Myosotis arvensis*)
Asclepiadaceae:
  common milkweed (*Asclepias syriaca*)
Euphorbiaceae:
  sun spurge (*Euphorbia helioscopia*), spotted spurge (*Euphorbia maculata*)
Gramineae:
  barnyardgrass (*Echinochloa crus-galli*), green foxtail (*Setaria viridis*), giant foxtail (*Setaria faberi*), large crabgrass (*Digitaria sanguinalis*), goosegrass (*Eletisine indica*), annual bluegrass (*Poa annua*), blackgrass (*Alopecurus myosuroides*), wild oat (*Avena fatua*), johnsongrass (*Sorghum halepense*), quackgrass (*Agropyron repens*), downy brome (*Bromus tectorum*), bermudagrass (*Cynodon dactylon*), fall panicum (*Panicum dichotomiflorum*), Texas panicum (*Panicum texantum*), shattercane (*Sorghum vulgare*)
Commelinaceae:
  common dayflower (*Commelina communis*)
Equisetaceae:
  field horsetail (*Equisetum arvense*)
Cyperaceae:
  rice flatsedge (*Cyperus iria*), purple nutsedge (*Cyperus rotundus*), yellow nutsedge (*Cyperus esculentits*)

The pyridazin-3-one derivatives of formula (7) can attain effective control of various unfavorable weeds in the no-tillage cultivation of soybean (*Glycine max*), corn (*Zea mays*) and wheat (*Triticum aestivum*).

The pyridazin-3-one derivatives of formula (7) have herbicidal activity in the flooding treatment on paddy fields against various unfavorable weeds as described below.

Gramineae:
　barnyardgrass (*Echinochloa oryzicola*)

Scrophulariaceae:
　common falsepimpemel (*Lindernia procumbens*)

Lythraceae:
　*Rotala indica, Ammannia multiflora*

Elatinaceae:
　*Elatine triandra*

Cyperaceae:
　smallflower umbrellaplant (*Cyperus difformis*), hardstem bulrush (*Scirpus juncoides*), needle spikerush (*Eleocharis acicularis*), *Cyperus serotinus, Eleocharis kiurogitwai*

Pontederiaceae:
　*Monochoria vaginalis*

Alismataceae:
　*Sagittaria pygmaea, Sagittaria trifolia, Alisma canaticulattim*

Potamogetonaceae:
　roundleaf pondweed (*Potamogeton distinctus*)

Umbelliferae:
　*Oenanthe javanica*

The pyridazin-3-one derivatives of formula (7) can attain effective control of various unfavorable weeds that will grow in orchards, grasslands, lawns, forests, waterways, canals or other non-cultivated lands.

The pyridazin-3-one derivatives of formula (7) have herbicidal activity against various aquatic unfavorable weeds such as water hyacinth (*Eichhornia crassipes*) that will grow in waterways, canals or other watersides.

The pyridazin-3-one derivatives of formula (7) can exhibit selectivity between crop plants and unfavorable weeds for main crops such as corn (*Zea mays*), wheat (*Tritictim aestivum*), barley (*Hordeum vulgare*), rice (*Oryza sativa*), sorghum (*Sorghum bicolor*), soybean (*Glycine max*), cotton (*Gossypium spp.*), sugar beet (*Beta vulgaris*), peanut (*Arachis hypogaea*), sunflower (*Helianthus annuus*) and canola (*Brassica naputs*); garden crops such as flowers, ornamental plants and vegetable crops; and transplanted paddy rice.

The pyridazin-3-one derivatives of formula (7) are usually mixed, when used as active ingredients of herbicides, with solid or liquid carriers or diluents, surfactants and other adjuvants to give formulations such as emulsifiable concentrates, wettable powders, flowables, granules, concentrated emulsions or water-dispersible granules.

These formulations contain at least one of the pyridazin-3-one derivatives of formula (7) as an active ingredient at an amount of 0.001% to 80% by weight, preferably 0.005% to 70% by weight, based on the total weight of the formulation.

Examples of the solid carrier or diluent may include fine powders or granules of the following materials: mineral matters such as kaolin clay, attapulgite clay, bentonite, terra alba, pyrophyllite, talc, diatomaceous earth and calcite; organic substances such as walnut shell powder; water-soluble organic substances such as urea; inorganic salts such as ammonium sulfate; and synthetic hydrated silicon oxide. Examples of the liquid carrier or diluent may include aromatic hydrocarbons such as methylnaphthalene, phenylxylylethane, and alkylbenzenes, e.g., xylene; alcohols such as isopropanol, ethylene glycol and 2-ethoxyethanol; esters such as phthalic acid dialkyl esters; ketones such as acetone, cyclohexanone and isophorone; mineral oils such as machine oil; vegetable oils such as soybean oil and cotton seed oil; dimethylsulfoxide, N,N-dimethylformamide, acetonitrile, N-methylpyrrolidone, and water.

Examples of the surfactant used for emulsification, dispersing or spreading may include surfactants of the anionic type, such as alkylsulfates, alkylsulfonates, alkylarylsulfonates, dialkylsulfosuccinates and phosphates of polyoxyethylene alkyl aryl ethers; and surfactants of the nonionic type, such as polyoxyethylene alkyl ethers, polyoxyethylene alkyl aryl ethers, polyoxyethylene polyoxypropylene block copolymers, sorbitan fatty acid esters and polyoxyethylene sorbitan fatty acid esters.

Examples of the adjuvant used for formulation may include ligninsulfonates, alginates, polyvinyl alcohol, gum arabic, carboxymethyl cellulose (CMC) and isopropyl acid phosphate (PAP).

The pyridazin-3-one derivatives of formula (7) are usually formulated and used in the soil, foliar or flooding treatment before or after the emergence of unfavorable weeds. The soil treatment may include soil surface treatment and soil incorporation. The foliar treatment may include application over the plants and directed application in which a chemical is applied only to unfavorable weeds so as to keep off the crop plants.

When the pyridazin-3-one derivatives of formula (7) are used as active ingredients of herbicides, the application amount is usually in the range of 0.01 to 10,000 g, preferably 1 to 8000 g, per hectare, although it may vary depending upon the weather conditions, formulation type, application timing, application method, soil conditions, crop plants, unfavorable weeds and other factors. Formulations such as emulsifiable concentrates, wettable powders, flowables, concentrated emulsions or water-dispersible granules are usually applied after diluted at a prescribed amount with about 10 to 1000 liters per hectare of water optionally containing an adjuvant such as a spreading agent. Formulations such as granules or some types of flowables are usually applied without dilution.

Examples of the adjuvant used, if necessary, may include, in addition to the above surfactants, polyoxyethylene resin acids (esters), ligninsulfonates, abietates, dinaphthylmethanedisulfonates, crop oil concentrates, and vegetable oils such as soybean oil, corn oil, cotton seed oil and sunflower oil.

EXAMPLES

The present invention will be further illustrated by the following production examples, formulation examples and test examples; however, the present invention is not limited to these examples.

1) Production of the Present Compounds by Process 1

Production Example 1-1

Under a stream of nitrogen gas, 3.086 g of 3,3,3-trifluoro-2-oxopropanal 1-(4-chloro-2-fluoro-5-hydroxyphenylhydrazone), compound 3-1 was dissolved in 20 ml of pyridine. To this solution were added 1.07 ml of piperidine and 2.561 g of methylmalonic acid, and the mixture was heated to 80° C. and stirred for 1.5 hours. The reaction solution was left cooling to room temperature and concentrated under reduced pressure. The residue was diluted with 100 ml of diethyl ether. The diluted solution was washed twice with 20 ml of 3 N HCl and once with 30 ml of saturated aqueous sodium bicarbonate solution, dried with magnesium sulfate, filtered, and concentrated under reduced pressure. The residue was subjected to column chromatography to give 2.164 g of a compound of formula (13) wherein X=F, Y=Cl, B=OH, $R^2$=$CH_3$, $R^3$=H, and M=H, i.e., present compound 1-2, as a mixture of the following two isomers.

Isomer A $^1$H-NMR (300 MHz, acetone-$d_6$, TMS) δ (ppm): 1.34 (d, 3H), 3.20 (q, 1H), 7.08 (d, 1H), 7.22 (d, 1H), 7.72 (brs, 1H), 9.68 (brs, 1H).

Isomer B $^1$H-NMR (300 MHz, acetone-$d_6$, TMS) δ (ppm): 1.35 (d, 3H), 3.20 (q, 1H), 7.08 (d, 1H), 7.19 (d, 1H), 7.52 (brs, 1H), 9.58 (brs, 1H).

Production Example 1-2

Under a stream of nitrogen gas, 2.00 g of 3,3,3-trifluoro-2-oxopropanal 1-(4-chloro-2-fluoro-5-hydroxyhenylhydrazone), compound 3-1 was dissolved in 7.0 g of toluene. To this solution were added 1.7 g of triethylamine and 1.1 g of methylmalonic acid, and the mixture was heated to 80° C. and stirred for 2 hours. The reaction mixture was left cooling to room temperature. The precipitated crystals were collected by filtration and washed twice with 2.0 ml of toluene to give a compound of formula (13) wherein X=F, Y=Cl, B=OH, $R^2$=$CH_3$, $R^3$=H, and M=HN($C_2H_5$)$_3$, i.e., compound 1-424.

$^1$H-NMR (300 MHz, DMSO-$d_6$, TMS) δ(ppm): 1.0–1.4 (m, 12H), 2.6–3.2 (m, 7H), 6.8–7.6 (m, 3H), 9.9–10.3 (m, 1H).

Production Example 1-3

To present compound 1-424 obtained in Production Example 1-2 were added 100 ml of ethyl acetate and 50 ml of 10% HCl, followed by phase separation. The organic layer was dried with magnesium sulfate and concentrated under reduced pressure to give 2.6 g of a compound of formula (13) wherein X=F, Y=Cl, B=OH, $R^2$=$CH_3$, $R^3$=H, and M=H, i.e., present compound 1-2, as a crude product.

Production Example 1-4

Under a stream of nitrogen gas, 0.50 g of 3,3,3-trifluoro-2-oxopropanal 1-(4-chloro-2-fluoro-5-hydroxyphenylhydrazone), compound 3-3 was dissolved in 3.0 ml of pyridine. To this solution were added 0.167 ml of piperidine and 0.199 g of methylmalonic acid, and the mixture was heated to 80° C. and stirred for 3.5 hours. The reaction solution was left cooling to room temperature and concentrated under reduced pressure. The residue was diluted with 100 ml of diethyl ether. The diluted solution was washed twice with 20 ml of 3 N HCl and once with 30 ml of saturated aqueous sodium bicarbonate solution, dried with magnesium sulfate, filtered, and concentrated under reduced pressure. The residue was subjected to column chromatography to give 0.467 g of a compound of formula (13) wherein X=F, Y=Cl, B=OCH($CH_3$)$_2$, $R^2$=$CH_3$, $R^3$=H, and M=H, i.e., present compound 1-5, as a mixture of the following two isomers.

Isomer A $^1$H-NMR (300 MHz, CDCl$_3$, TMS) δ(ppm): 1.32 (d, 3H), 1.35 (d, 3H), 1.37 (d, 3H), 3.26 (q, 1H), 4.48 (m, 1H), 7.02–7.10 (m, 2H), 7.25 (brs, 1H), 8.04 (brs, 1H).

Isomer B $^1$H-NMR (300 MHz, CDCl$_3$, TMS) δ(ppm): 1.35–1.43 (m, 9H), 3.22 (brq, 1H), 4.47 (m, 1H), 6.98 (d, 1H), 7.07 (d, 1H), 7.16 (brs, 1H), 7.90 (brs, 1H).

Production Example 1-5

First, 0.25 g of 3,3,3-trifluoro-2-oxopropanal 1-(4-chloro-2-fluoro-5-iso-propoxyphenylhydrazone), compound 3-3 was dissolved in 1.0 g of ethanol. To this solution were added 0.15 g of triethylamine and 0.18 g of methylmalonic acid. The reaction was allowed to proceed at 80° C. for 3.5 hours to give present compound 1-5 in 95% yield as determined by the internal standard method using liquid chromatography.

Production Example 1-6

First, 3.0 g of 3,3,3-trifluoro-2-oxopropanal 1-(4-chloro-2-fluoro-5-iso-propoxyphenylhydrazone), compound 3-3 was dissolved in 10.0 g of toluene. To this solution were added 1.4 g of triethylamine and 1.6 g of methylmalonic acid, and the mixture was heated to 80° C. and stirred for 3.5 hours. The reaction solution was left cooling to room temperature, and the precipitated crystals were collected by filtration to give 2.85 g of a compound of formula (13) wherein X=F, Y=Cl, B=OCH($CH_3$)$_2$, $R^2$=$CH_3$, $R^3$=H, and M=HN($C_2H_5$)$_3$, i.e., present compound 1-427.

$^1$H-NMR (250 MHz, CDCl$_3$, TMS) δ(ppm): 1.1–1.5 (m, 18H), 2.6–3.2 (m, 7H), 4.4–4.7 (m, 1H), 6.1 (s, 1H), 6.9–7.2 (m, 3H), 7.7 (s, 1H), 10.9 (s, 1H).

Production Example 1-7

Under a stream of nitrogen gas, 0.425 g of 3,3,3-trifluoro-2-oxopropanal 1-(4-chloro-2-fluoro-5-(1-methyl-2-propynyl)oxyphenylhydrazone), compound 3-5 was added to 3.0 ml of toluene. To this solution were added 0.26 ml of triethylarnine and 0.179 g of methylmalonic acid, and the mixture was heated to 80° C. and stirred for 2 hours. The reaction solution was left cooling to room temperature and concentrated under reduced pressure. The residue was diluted with 100 ml of diethyl ether. The diluted solution was washed twice with 20 ml of 3 N HCl. The organic layer was washed once with 100 ml of saturated aqueous sodium bicarbonate solution. After removal of the organic layer, the residue was subjected to column chromatography to give two isomers (140 mg+58 mg) of a compound of formula (13) wherein X=F, Y=Cl, B=OCH—($CH_3$)C≡CH, $R^2$=$CH_3$, $R^3$=H, and M=H, i.e., present compound 1-8.

Isomer 1, component of 140 mg $^1$H-NMR (300 MHz, CDCl$_3$, TMS) δ(ppm): 1.35 (brd, 3H), 1.69 (d, 3H), 2.54 (s, 1H), 3.19 (brs, 1H), 4.83 (brs, 1H), 7.07 (d, 1H), 7.16 (brs, 1H), 7.28 (m, 1H), 7.98 (brs, 1H).

Isomer 2, component of 58 mg $^1$H-NMR (300 MHz, CDCl$_3$, TMS) δ(ppm): 1.34 (brd, 3H), 1.71 (m, 3H), 2.54 (m, 1H), 3.24 (brt, 1H), 4.86 (brq, 1H), 7.07 (d, 1H), 7.26 (m, 1H), 7.35 (brs, 1H), 8.09 (brd, 1H).

Production Example 1-8

Under a stream of nitrogen gas, 0.466 g of 3,3,3-trifluoro-2-oxopropanal 1-(4-chloro-2-fluoro-5-(ethoxycarbonyl)methoxyphenylhydrazone), compound 3-8 was added to 5.0 ml of toluene. To this solution were added 0.46 ml of triethylamine and 0.356 g of methylmalonic acid, and the mixture was heated to 80° C. and stirred for 2 hours. The reaction solution was left cooling to room temperature and concentrated under reduced pressure. The residue was diluted with 100 ml of diethyl ether. The diluted solution was washed twice with 20 ml of 3 N HCl. The organic layer was extracted with 100 ml of saturated aqueous sodium bicarbonate solution. The water layer was adjusted to pH 4 by the addition of 3 N HCl. The water layer was extracted with 100 ml of diethyl ether. The organic layer was dried with magnesium sulfate and concentrated under reduced pressure to give 0.338 g of a compound of formula (13) wherein X=F, Y=Cl, B=OCH$_2$COOC$_2$H$_5$, R$^2$=CH$_3$, R$^3$=H, and M=H, i.e., present compound 1-11.

$^1$H-NMR (300 MHz, CDCl$_3$, TMS) δ(ppm): 1.17 (t, 3H), 1.23 (d, 3H), 3.08 (q, 1H), 4.16 (q, 2H), 4.59 (s, 2H), 6.82 (d, 1H), 6.92 (d, 1H), 7.13 (s, 1H), 8.22 (s, 1H).

Production Example 1-9

Under a stream of nitrogen gas, 1.00 g of 3,3,3-trifluoro-2-oxopropanal 1-(4-chloro-2-fluoro-5-isopropoxyphenylhydrazone), compound 3-3 was dissolved in 3 g of toluene. To this solution were added 0.4 g of triethylamine and 0.4 g of malonic acid, and the mixture was heated to 80° C. and stirred for 3.5 hours. The reaction solution was left cooling to room temperature and concentrated under reduced pressure. The residue was diluted with 30 ml of ethyl acetate. The diluted solution was washed once with 20 ml of 10% hydrochloric acid, dried with magnesium sulfate, filtered, and concentrated under reduced pressure. The residue was subjected to column chromatography to give 0.9 g of a compound of formula (13) wherein X=F, Y=Cl, B=OCH(CH$_3$)$_2$, R$^2$=H, R$^3$=H, and M=H, i.e., present compound 1-65.

$^1$H-NMR (250 MHz, CDCl$_3$, TMS) δ(ppm): 1.31 (d, 3H), 1.37 (d, 3H), 2.91 (d, 1H), 3.14 (d, 1H), 4.30–4.50 (m, 1H), 6.96 (d, 1H), 7.04 (s, 1H), 7.06 (d, 1H), 7.57 (brs, 1H).

Production Example 1-10

First, 0.65 g of 3,3,3-trifluoro-2-oxopropanal 1-(4-chloro-2-fluoro-5-isopro-poxyphenylhydrazone), compound 3-3 and 0.53 g of ethylmalonic acid were dissolved in 4.0 ml of triethylamine. The solution was stirred at room temperature for 30 minutes and heated under reflux for 1.5 hours. The reaction solution was left cooling to room temperature, and the solvent was distilled out under reduced pressure. The residue was subjected to silica gel column chromatography to give a compound of formula (13) wherein X=F, Y=Cl, B=OCH(CH$_3$)$_2$, R$^2$=CH$_2$CH$_3$, R$^3$=H, and M=H, i.e., present compound 1-153, as a crude product.

$^1$H-NMR (300 MHz, CDCl$_3$, TMS) δ(ppm): 1.03 (t, 3H), 1.37 (d, 6H), 1.81 (m, 2H), 3.05 (m, 1H), 4.48 (m, 1H), 6.98 (d, 1H), 7.08 (d, 1H), 7.15 (s, 1H), 7.90 (brs, 1H).

2) Production of Pyridazin-3-one Derivatives from the Present Compounds by Process 2

Production Example 2-1

Under a stream of nitrogen gas, 0.315 g of present compound 1-2 was dissolved in 1.0 ml of acetic acid and 1.0 ml of pyridine, and the solution was stirred at 120° C. for 8 hours. The reaction solution was left cooling to room temperature and concentrated under reduced pressure. The residue was diluted with 100 ml of diethyl ether. The diluted solution was washed twice with 20 ml of 3 N HCl and once with 30 ml of saturated aqueous sodium bicarbonate solution, dried with magnesium sulfate, filtered, and concentrated under reduced pressure. The residue was subjected to column chromatography to give 0.227 g of 2-(2-fluoro-4-chloro-5-hydroxyphenyl)-4-methyl-5-trifluoromethylpyridazin-3-one, compound 5-1, m.p., 177.6° C.

Production Example 2-2

First, 0.5025 g of present compound 1-2 was dissolved in 2.0 ml of propionic acid. The solution was heated at 130° C. for 7.5 hours to give 2-(2-fluoro-4-chloro-5-hydroxyphenyl)-4-methyl-5-trifluoromethylpyridazin-3-one in 54.6% yield as determined by the LC-ES method. This method refers to a technique of determining the concentration of a desired product in the reaction solution by measuring the detection intensity in liquid chromatography of a previously isolated product at a constant concentration; measuring the detection intensity in liquid chromatography of a desired product under the same conditions, in which the desired product has been prepared in a solution obtained by adjusting the reaction solution to have the constant concentration after completion of the reaction; and comparing these detection intensities to determine the concentration of the desired product in the reaction solution.

Production Example 2-3

First, 27.87 g of present compound 1-2 was dissolved in 551.94 g of chlorobenzene. To this solution were added 44.18 g of 5-ethyl-2-methylpyridine and 16 ml of valeric acid, and the mixture was heated under reflux to cause azeotropic dehydration for 24 hours. This gave 2-(2-fluoro-4-chloro-5-hydroxyphenyl)-4-methyl-5-trifluoromethyl-pyridazin-3-one in 73.7% yield as determined by the LC-ES method.

Production Example 2-4

First, 20.94 g of present compound 1-2 was dissolved in 26.18 g of toluene. To this solution were added 13.32 g of 5-ethyl-2-methylpyridine and 8.16 g of propionic acid, and the mixture was heated under reflux to cause azeotropic dehydration for 22.5 hours. This gave 2-(2-fluoro-4-chloro-5-hydroxyphenyl)-4-methyl-5-trifluoro-methylpyridazin-3-one in 74.2% yield as determined by the LC-ES method.

Production Example 2-5

First, 0.1182 g of present compound 1-2 was dissolved in 3.0 g of chlorobenzene. To this solution was added 0.0498 g of 5-ethyl-2-methylpyridine, and the mixture was heated under reflux for 21.5 hours. This gave 2-(2-fluoro-4-chloro-5-hydroxyphenyl)-4-methyl-5-trifluoromethylpyridazin-3-one in 58.2% yield as determined by the LC-ES method.

Production Example 2-6

First, 0.3469 g of present compound 1-2 was dissolved in 5.0 ml of chlorobenzene. To this solution were added 0.38 ml of 5-ethyl-2-methylpyridine and a catalytic amount of N,N-dimethylformamide. Then, 0.14 ml of thionyl chloride was added at 30° C., and the mixture was heated at 60° C. for 1 hour. This gave 2-(2-fluoro-4-chloro-5-hydroxyphenyl)-4-methyl-5-trifluoromethylpyridazin-3-one in 45.0% yield as determined by the LC-ES method.

Production Example 2-7

First, 1.0 g of present compound 1-5 was dissolved in 3 ml of xylene, and the solution was heated under reflux for 4 hours. The reaction solution was left cooling to room temperature and concentrated under reduced pressure. The residue was subjected to column chromatography to give 0.36 g of 2-(2-fluoro-4-chloro-5-isopropoxyphenyl)-4-methyl-5-trifluoromethylpyridazin-3-one, compound 5-2.

$^1$H-NMR (300 MHz, CDCl$_3$, TMS) δ(ppm): 1.38 (d, 6H, J=6.3 Hz), 2.43 (q, 3H, J=2.0 Hz), 4.47 (m, 1H), 6.99 (d, 1H, J=5.0 Hz), 7.29 (d, 1H, J=9.5 Hz), 8.00 (s, 1H).

Production Example 2-8

Under a stream of nitrogen gas, 0.467 g of present compound 1-5 was dissolved in 2.0 ml of acetic acid, and the solution was stirred at 120° C. for 11.5 hours. The reaction solution was left cooling to room temperature, and concentrated under reduced pressure. The residue was diluted with 100 ml of diethyl ether. The diluted solution was washed once with 30 ml of saturated aqueous sodium bicarbonate solution, dried with magnesium sulfate, filtered, and concentrated under reduced pressure. The residue was column chromatography to give 0.334 g of 2-(2-fluoro-4-chloro-5-isopro-poxyphenyl)-4-methyl-5-trifluoromethylpyridazin-3-one, compound 5-2.

Production Example 2-9

First, 0.512 g of present compound 1-5 was dissolved in 2.0 g of xylene. To this solution was added 0.215 g of 4-nitrobenzoic acid, and the mixture was stirred with heating under reflux for 6 hours to give 2-(2-fluoro-4-chloro-5-isopropoxyphenyl)-4-methyl-5-trifluoromethylpyridazin-3-one, compound 5-2 in 56% yield as determined by the internal standard method using liquid chromatography.

Production Example 2-10

First, 15.0 g of present compound 1-5 was dissolved in 75.0 g of xylene. To this solution was added 0.72 g of p-toluenesulfonic acid monohydrate, and the mixture was stirred at 81° C. for 15 hours to give 2-(2-fluoro-4-chloro-5-isopropoxyphenyl)-4-methyl-5-trifluoromethylpyridazin-3-one, compound 5-2 in 49% yield as determined by the internal standard method using liquid chromatography.

Production Example 2-11

First, 5.0 g of present compound 1-5 was dissolved in 25 g of xylene. To this solution was added 2.3 g of tri-n-butylarnine, and the mixture was refluxed at 145° to 160° C. for 26 hours under dehydration with molecular sieve 3A. After completion of the reaction, the reaction solution was left cooling to room temperature, to which ethyl acetate and 10% hydrochloric acid were added, and the mixture was subjected to phase separation. The organic layer was dried and concentrated. The residue was subjected to column chromatography to give 3.4 g of 2-(2-fluoro-4-chloro-5-isopropoxyphenyl)-4-methyl-5-trifluoromethylpyridazin-3-one, compound 5-2.

Production Example 2-12

First, 15.04 g of present compound 1-5 was dissolved in 75.12 g of xylene. To this solution was added 3.84 g of triethylamine, and the mixture was stirred at 132° C. for 21 hours under dehydration with molecular sieve 3A. This gave 2-(2-fluoro-4-chloro-5-isopropoxyphenyl)-4-methyl-5-trifluoromethylpyridazin-3-one in 71% yield as determined by the internal standard method using liquid chromatography.

Production Example 2-13

First, 14.99 g of present compound 1-5 was dissolved in 74.9 g of xylene. To this solution was added 3.49 g of 4-picoline, and the mixture was stirred at 131° to 137° C. for 26 hours under dehydration with a Dean-Stalk trap. This gave 2-(2-fluoro-4-chloro-5-isopropoxyphenyl)-4-methyl-5-trifluoromethylpyridazin-3-one, compound 5-2 in 85% yield as determined by the internal standard method using liquid chromatography.

Production Example 2-14

First, 0.25 g of present compound 1-5 was dissolved in 1.0 g of xylene at room temperature. To this solution was added 0.14 g of quinoline, and the mixture was heated under reflux for 4 hours to give 2-(2-fluoro-4-chloro-5-isoporpoxyphenyl)-4-methyl-5-trifluoromethylpyridazin-3-one, compound 5-2 in 55% yield as determined by the internal standard method using liquid chromatography.

Production Example 2-15

First, 0.25 g of present compound 1-5 was dissolved in 1.0 g of xylene at room temperature. To this solution was added 0.09 g of N,N-dimethylaniline, and the mixture was heated under reflux for 4 hours to give 2-(2-fluoro-4-chloro-5-isopropoxy-phenyl)-4-methyl-5-trifluoromethylpyridazin-3-one, compound 5-2 in 60% yield as determined by the internal standard method using liquid chromatography.

Production Example 2-16

First, 15.05 g of present compound 1-5 was dissolved in 6.03 g of acetic acid and 29.45 g of pyridine, and the solution was stirred at 127° C. for 8 hours to give 2-(2-fluoro-4-chloro -5-isopropoxyphenyl)-4-methyl -5-trifluoromethylpyridazin-3-one, compound 5-2 in 82% yield as determined by the internal standard method using liquid chromatography.

Production Example 2-17

First, 5.00 g of present compound 1-5 was dissolved in 25 g of xylene. To this solution were added 0.919 g of propionic acid and 1.159 g of 4-picoline, and the mixture was stirred at 142° C. for 13.5 hours under dehydration with molecular sieve 3A. This gave 2-(2-fluoro-4-chloro-5-isopropoxyphenyl)-4-methyl-5-trifluoromethylpyridazin-3-one, compound 5-2 in 90.1 % yield as determined by the internal standard method using liquid chromatography.

Production Example 2-18

First, 5.001 g of present compound 1-5 was dissolved in 25 g of xylene. To this solution were added 2.084 g of 4-nitrobenzoic acid and 1.160 g of 4-picoline, and the mixture was stirred at 148° C. for 6 hours under dehydration with molecular sieve 3A. This gave 2-(2-fluoro-4-chloro-5-isopropoxyphenyl)-4-methyl-5-trifluoromethylpyridazin-3-one, compound 5-2 in 93.5% yield as determined by the internal standard method using liquid chromatography.

Production Example 2-19

First, 6.77 g of present compound 1-5 was dissolved in 59 g of xylene. The solution was mixed with 2.45 g of 5-ethyl-2-methylpyridine, 1.25 g of propionic acid, and 0.68 g of calcium carbonate. The mixture was azeotropically dehydrated with heating under reflux for 10 hours. After completion of the reaction, the reaction solution was cooled to room temperature and poured into 20 ml of 5% hydrochloric acid. The mixture was extracted with ethyl acetate. The organic layer was washed 20 ml of 20% aqueous sodium chloride solution, dried with magnesium sulfate, and concentrated. The residue was purified by silica gel chromatography to give 4.91 g (80% yield) of 2-(2-fluoro-4-chloro-5-isopropoxyphenyl)-4-methyl-5-trifluoromethylpyridazin-3-one.

Production Example 2-20

First, 0.5 g of present compound 1-5 was dissolved in 10 ml of tetrahydrofuran. To this solution was added 0.25 g of triethylamine, and the mixture was stirred at 30° C. for 10 minutes. Then, a solution of 0.2 g of ethyl chloroformate dissolved in 3 ml of tetrahydrofuran was added dropwise at the same temperature over 20 minutes. After completion of the dropwise addition, the reaction solution was poured into water, and the mixture was extracted with ethyl acetate. The organic layer was washed with 5% hydrochloric acid, dried with magnesium sulfate, and concentrated. The residue was subjected to column chromatography to give 0.19 g of 2-(2-fluoro-4-chloro-5-isopropoxyphenyl)-4-methyl-5-trifluoromethylpyridazin-3-one.

Production Example 2-21

First, 0.25 g of present compound 1-427 was dissolved in 2.0 g of xylene. The solution was heated under reflux for 9 hours to give 2-(2-fluoro-4-chloro-5-isopro-poxyphenyl)-4-methyl-5-trifluoromethylpyridazin-3-one, compound 5-2 in 20% yield as determined by the internal standard method using liquid chromatography.

Production Example 2-22

First, 1 ml of pyridine and 1 ml of acetic acid were added to 0.198 g of present compound 1-8, and the mixture was stirred at 120° C. for 5 hours. The reaction solution was left cooling to room temperature and concentrated under reduced pressure. The residue was subjected to column chromatography to give 0.086 g of 2-(4-chloro-2-fluoro-5-((1-methyl-2-propionyl)oxy)phenyl)-4-methyl-5-trifluoromethylpyridazin-3-one, compound 5-4, m.p., 114.1° C.

Production Example 2-23

First, 1 ml of pyridine and 1 ml of acetic acid were added to 0.321 g of present compound 1-11, and the mixture was stirred at 120° C. for 5 hours. The reaction solution was left cooling to room temperature and concentrated under reduced pressure. The residue was subjected to column chromatography to give 0.189 g of ethyl 2-(2-chloro-4-fluoro-5-(5-methyl-6-oxo-4-trifluoromethyl-1,6-dihydro-1-pyridazinyl)phenoxy)-acetate, compound 5-6, m.p., 102.0° C.

Production Example 2-24

A mixture of 0.43 g of present compound 1-153, 2.0 ml of acetic acid, and 1.0 ml of pyridine was heated under reflux for 3 hours. The reaction solution was left cooling to room temperature, and the acetic acid and pyridine were distilled out under reduced pressure. The residue was subjected to silica gel column chromatography to 84 mg of 2-(4-chloro-2-fluoro-5-isopropoxyphenyl)-4-ethyl-5-trifluoromethylpyridazin-3-one, compound 5-9.

$^1$H-NMR (300 MHz, CDCl$_3$, TMS) δ(ppm): 1.26 (t, 3H, J=7.5 Hz), 1.38 (d, 6H, J=6.2 Hz), 2.86 (dq, 2H, J=7.5 Hz, 1.3 Hz), 4.49 (qq, 1H, J=6.2 Hz), 7.00 (d, 1H, J=6.5 Hz), 7.29 (d, 1H, J=9.3 Hz), 7.99 (s, 1H).

Production Example 2-25

First, 1.0 g of present compound 1-65 was dissolved in 4.35 g of acetic acid and 2.17 g of pyridine, and the solution was stirred at 120° C. for 8.5 hours. The reaction solution was left cooling to room temperature and poured into diluted hydrochloric acid. The mixture was extracted with ethyl acetate. The organic layer was washed with saturated aqueous sodium bicarbonate solution, dried with magnesium sulfate, and concentrated to give a crude product. The crude product was subjected to column chromatography to give 0.47 g of 2-(2-fluoro-4-chloro-5-isopropoxyphenyl)-5-trifluoromethyl-pyridazin-3-one, compound 5-10, m.p., 68.6° C.

3) Production without Isolation of the Present Compounds

Production Example 3-1

Under a stream of nitrogen gas, 0.295 g of 3,3,3-trifluoro-2-oxopropanal 1-(4-chloro-2-fluoro-5-hydroxyphenylhydrazone), compound 3-1 was dissolved in 2.0 ml of pyridine. To this solution were added 0.113 ml of piperidine and 0.295 g of methylmalonic acid, and the mixture was heated to 70° C. and stirred for 2.5 hours. Then, 2.0 ml of acetic acid was added, and stirring was further continued at 130° C. for 7 hours. The reaction solution was left cooling to room temperature and concentrated under reduced pressure. The residue was diluted with 100 ml of diethyl ether. The diluted solution was washed twice with 20 ml of 3 N hydrochloric acid and once with 30 ml of saturated aqueous sodium bicarbonate solution, dried with magnesium sulfate, filtered, and concentrated under reduced pressure. The residue was subjected to column chromatography to give 0.184 g of 2-(2-fluoro-4-chloro-5-hydroxyphenyl)-4-methyl-5-trifluoro-methylpyridazin-3-one, compound 5-1.

Production Example 3-2

Under a stream of nitrogen gas, 0.399 g of 3,3,3-trifluoro-2-oxopropanal 1-(4-chloro-2-fluoro-5-isopropoxyphenylhydrazone), compound 3-3 was dissolved in 2.4 ml of pyridine at room temperature. To this solution were added 0.133 ml of piperidine and 0.159 g of methylmalonic acid, and the mixture was heated to 70° C. and stirred for 3.5 hours. Then, 2.4 ml of acetic acid was added, and stirring was further continued at 130° C. for 8 hours. The reaction solution was left cooling to room temperature and concentrated under reduced pressure. The residue was diluted with 100 ml of diethyl ether. The diluted solution was washed twice with 20 ml of 3 N hydrochloric acid and once with 30 m of saturated sodium bicarbonate solution, dried with magnesium sulfate, filtered, and concentrated under reduced pressure. The residue was subjected to column chromatography to give 0.255 g of 2-(2-fluoro-4-chloro-5-isopropoxyphenyl)-4-methyl-5-trifluoromethylpyridazin-3-one, compound 5-2.

Production Example 3-3

First, 0.62 g of 3,3,3-trifluoro-2-oxopropanal 1-(4-chloro-2-fluoro-5-(carboxymethoxy)phenylhydrazone, compound 3-6 was dissolved in 4.6 ml of pyridine, to which 0.5 g of methylmalonic acid and 0.14 g of piperidine were added, and the mixture was stirred at 70° C. for 3 hours. Then, 4.6 ml of acetic acid was added, and the mixture was stirred at an external temperature of 130° C. for 10 hours. After completion of the reaction, the reaction solution was poured into water, and the mixture was extracted with diethyl ether. The organic layer was washed with water and then with diluted hydrochloric acid, dried with anhydrous magnesium sulfate, and evaporated to remove the diethyl ether. The resulting crystals were recrystallized from a mixed solvent of hexane: diethyl ether=3:1. This gave 0.34 g of 2-(2-fluoro-4-chloro-5-(carboxymethoxy)-phenyl)-4-methyl-5-trifluoromethylpyridazin-3-one, compound 5-11.

Production Example 3-4

First, 0.25 g of 3,3,3-trifluoro-2-oxopropanal 1-(4-chlorophenylhydrazone), compound 3-11 was dissolved in 2 ml of pyridine. To this solution were added 0.24 g of methylmalonic acid and 0.09 g of piperidine, and the mixture was stirred at 80° C. for 4 hours. Then, 2.0 ml of acetic acid was added, and the mixture was stirred at 80° C. for 6.5 hours and further at 120° C. for 4 hours. After completion of the reaction, the reaction solution was poured into water, and this mixture was extracted with diethyl ether. The organic layer was washed with water and then with diluted hydrochloric acid, dried with anhydrous magnesium sulfate, and evaporated to remove the diethyl ether. The residue was subjected to silica gel column chromatography to give 0.15 g of 2-(4-chlorophenyl)-4-methyl-5-trifluoromethylpyridazin-3-one, compound 5-12, m.p., 80.8° C.

The following reference examples illustrate the preparation of starting material compounds used in process 1.

Reference Example 1

To a solution of 5.3 g (53.3 mmol) of sodium acetate dissolved in about 100 ml of water was added 6.6 g (24.3 mmol) of 1,1-dibromo-3,3,3-trifluoroacetone under ice cooling, and the reaction was allowed to proceed at 70° C. for 20 minutes. The reaction solution was left cooling to room temperature, to which a solution of 5.8 g (21.5 mmol) of 2-fluoro-4-chloro-5-isopropoxyphenylhydrazine dissolved in about 20 ml of diethyl ether was added, and the mixture was stirred at room temperature for 1 hour. The organic layer was separated, washed once with 10 ml of saturated aqueous sodium chloride solution, dried with anhydrous magnesium sulfate, and evaporated to remove the diethyl ether. This gave 6.5 g (20.0 mmol) of 3,3,3-trifluoro-2-oxo-propanal 1-(4-chloro-2-fluoro-5-isopropoxyphenylhydrazone), compound 3-3.

$^1$H-NMR (250 MHz, CDCl$_3$, TMS) δ(ppm): 1.39 (d, 6H, J=6.0 Hz), 4.38–4.52 (m, 1H), 7.15 (d, 1H, J=10.5 Hz), 7.22 (d, 1H, J=7.3 Hz), 7.43 (q, 1H, J=1.7 Hz), 9.18 (brs, 1H).

Reference Example 2

First, 32.3 g of 5-amino-2-chloro-4-fluorophenol, which had been produced in accordance with the method as described in European Patent Publication No. 61741-A, was mixed with 150 ml of concentrated hydrochloric acid, and the mixture was stirred at 50° C. for 30 minutes. To this mixture was added dropwise a solution of 15 g of sodium nitrite dissolved in 40 ml of water at 0° C. over 10 minutes. The reaction mixture was stirred at 0° C. for 1 hour and cooled to −50° C., to which a solution of 132 g of stannous chloride dissolved in 132 g of concentrated hydrochloric acid was quickly added dropwise at −50° C. The mixture was gradually returned to room temperature and stirred for 1 hour. The resulting solid product was collected by filtration and dried at 80° C. under reduced pressure to give 75 g of 2-fluoro-4-chloro-5-hydroxyphenylhydrazone hydrochloride as crude crystals.

$^1$H-NMR (250 MHz, DMSO-d$_6$, TMS) δ(ppm): 3–5 (br, 2H), 6.73 (d, 1H), 7.22 (d, 1H), 8.20 (s, 1H), 9–11 (brs, 2H).

Then, 49.2 g of sodium acetate and 40.5 g of 1,1-dibromo-3,3,3-trifluoro-acetone were dissolved in 400 ml of water, and the solution was heated at 80° to 90° C. for 40 minutes. The solution was cooled to 0° C., to which 75 g of crude crystals of 2-fluoro-4-chloro-5-hydroxyphenylhydrazone hydrochloride obtained by the above method was added. The reaction solution was stirred at room temperature for 70 minutes, and the resulting crystals were collected by filtration and dried under reduced pressure to give 35.4 g of 3,3,3-trifluoro-2-oxopropanal 1-(4-chloro-2-fluoro-5-hydroxyphenylhydrazone), compound 3-1.

$^1$H-NMR (300 MHz, CDCl$_3$, TMS) δ(ppm): 5.49 (s, 1H), 7.15 (d, 1H, J=10.5 Hz), 7.24 (d, 1H, J=7.4 Hz), 7.38 (q, 1H, J=1.8 Hz), 8.75 (s, 1H).

Reference Example 3

Production process based on the following scheme:

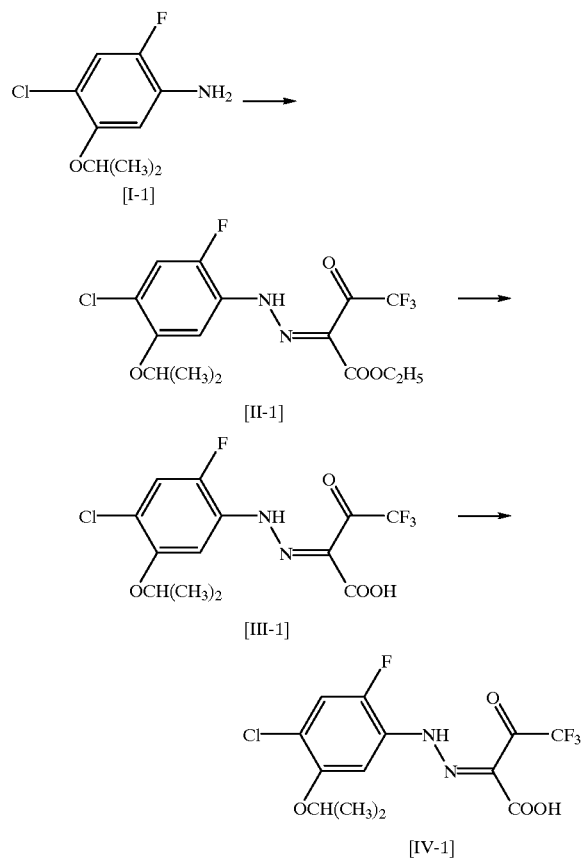

To a solution of 20.1 g of ethyl 4,4,4-trifluoroacetoacetate and 25 g of sodium acetate dissolved in 150 ml of water were added dropwise at a temperature below 10° C. a solution of a diazonium salt in acid derived from compound [I-1], which had been prepared from 20.3 g of 4-chloro-2-fluoro-5-isopropoxyaniline, 20 ml of concentrated hydrochloric acid, 20 ml of water, and 7.3 g of sodium nitrite. After completion of the dropwise addition, the mixture was stirred at room temperature for 1 hour, and the resulting crystals were collected by filtration, washed with water, and dried to give 34 g (85% yield) of compound [II-1] in the above scheme as crystals.

To a mixture of 30 ml of 1.4-dioxane and 3 ml of water were added 15.9 g of compound [II-1] obtained by the above reaction and 1.7 g of lithium hydroxide monohydrate, and the mixture was heated under reflux for 6 hours. The reaction solution was poured into ice water, neutralized with diluted hydrochloric acid, and extracted with ethyl acetate. The organic layer was dried and concentrated. The residue was washed with hexane to give 11.3 g (76.3% yield) of compound [III-1].

Then, 7.4 g of compound [III-1] obtained by the above reaction was dissolved in 42 ml of N,N-dimethylformamide. The reaction solution was heated to 100° C., kept at the same temperature for 30 minutes, and then cooled to room temperature. The reaction solution was poured into water and extracted with ethyl acetate. The organic layer was washed with diluted hydrochloric acid, dried with anhydrous magnesium sulfate, and concentrated to give 5.9 g (90% yield) of compound 3-3, compound [IV-1] in the above scheme.

$^1$H-NMR (250 MHz, CDCl$_3$, TMS) δ(ppm): 1.39 (d, 6H, J=6.0 Hz), 4.38–4.52 (m, 1H), 7.15 (d, 1H, J=10.5 Hz), 7.22 (d, 1H, J=7.3 Hz), 7.43 (q, 1H, J=1.7 Hz), 9.18 (br, 1H).

Reference Example 4

Production process based on the following scheme:

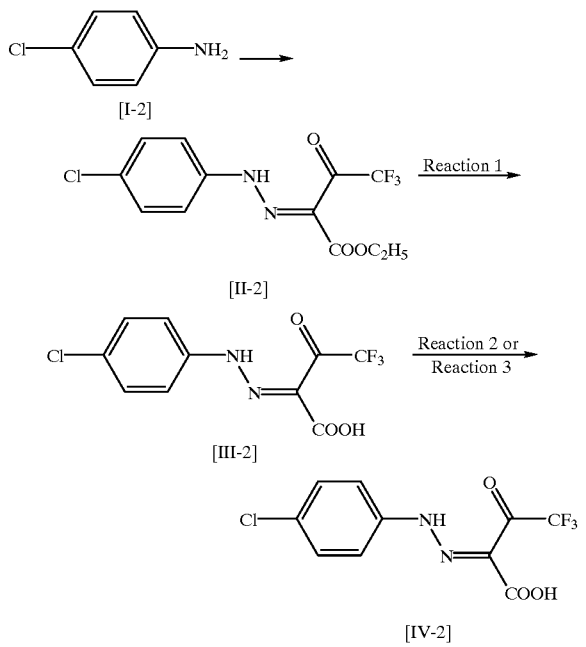

Reference Example 5

Production process based on the following scheme:

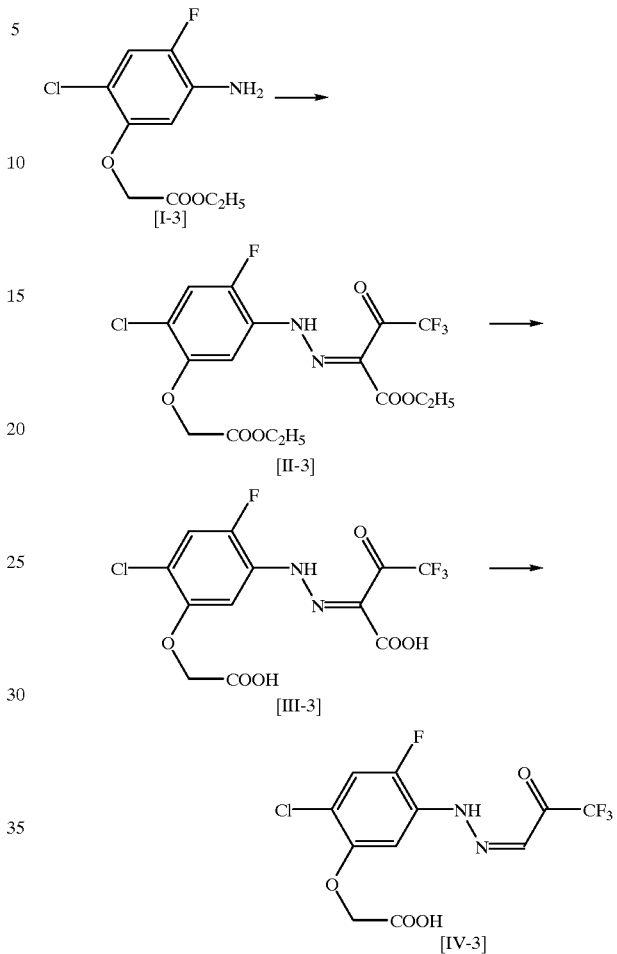

According to the process of Reference Example 3, compound [II-2] was produced from compound [I-2].

Reaction 1: To a mixture of 30 ml of 1,4-dioxane and 2 ml of water were added 5.0 of compound [II-2] and 0.67 of lithium hydroxide monohydrate, and the mixture was heated under reflux for 1.5 hours. The reaction solution was poured into ice water, neutralized with diluted hydrochloric acid, and extracted with ethyl acetate. The extract was dried and concentrated. The resulting crystals were washed with a mixed solvent of hexane-diethyl ether (hexane:diethyl ether=2:1) to give 3.3 g (73% yield) of compound [III-2].

Reaction 2: Then, 3.3 g of compound [III-2] obtained by reaction 1 above was dissolved in 10 m of dimethylsulfoxide, and the reaction solution was heated to 100° C. and kept at the same temperature for 10 minutes. The reaction solution was cooled to room temperature and directly subjected to silica gel column chromatography (eluent, hexane:ethyl acetate=7:1) to give 2.55 g (91% yield) of compound [IV-2].

Reaction 3: To 40 ml of toluene were added 5.0 g of compound [III-2] obtained by reaction 1 above, 0.5 ml of quinoline, and 0.1 g of copper powder. The reaction solution was heated to 100° C. and kept at the same temperature for 20 minute. The reaction solution was cooled to room temperature and directly subjected to silica gel chromatography (eluent, hexane:ethyl acetate=8:1) to give 3.6 g (86% yield) of compound 3-11, compound [IV-2] in the above scheme.

First, 24.7 g of ethyl 5-amino-2-chloro-4-fluorophenoxyacetate was suspended in 40 ml of water. To this suspension was added dropwise 40 ml of concentrated hydrochloric acid at room temperature, and the mixture was stirred for 30 minutes. The solution was cooled to 0° C., to which a solution of 7.6 g of sodium nitrite dissolved in 20 ml of water was added dropwise below 5° C., and the mixture was further stirred for 1 hour. The diazonium solution obtained by the above procedure was added dropwise to an aqueous solution consisting of 21 g of ethyl 4,4,4-trifluoroacetoacetate, 52 g of sodium acetate, and 105 ml of water at a temperature below 10° C., and the mixture was stirred for 30 minutes. The precipitated crystals were collected by filtration and dissolved in ethyl acetate. The solution was dried with magnesium sulfate and concentrated under reduced pressure. The residue was subjected to silica gel chromatography to give 19.5 g of compound [11-3].

$^1$H-NMR (250 MHz, CDCl$_3$, TMS) δ(ppm): 1.31 (t, 3H, J=7.16 Hz), 1.42 (t, 3H, J=7.1 Hz), 4.27 (q, 2H, J=7.16 Hz), 4.43 (q, 2H, J=7.12 Hz), 4.72 (s, 2H), 7.18 (d, 1H, J=6.73 Hz), 7.27 (d, 1H, J=10.0 Hz).

Then, 4.4 g of compound [II-3] obtained by the above reaction was dissolved in 20 ml of 1,4-dioxane. To this solution was added 1.26 g of lithium hydroxide monohydrate, and the mixture was refluxed for 3 hours. After completion of the reaction, the reaction solution was poured into water. The water layer was washed with ethyl acetate and acidified by the addition of diluted hydrochloric acid. The water layer was extracted with ethyl acetate. The organic layer was washed with water, dried with magnesium sulfate, and concentrated to remove the solvent under reduced pressure to give 2.92 g of compound [III-3].

$^1$H-NMR (250 MHz, CDCl$_3$, TMS) δ(ppm): 4.78 (s, 2H), 7.25 (d, 1H, J=6.42 Hz), 7.35 (d, 1H, J=9.82 Hz).

Then, 2.5 g of compound [III-3] obtained by the above reaction was dissolved in 10 ml of pyridine, and the solution was stirred at 100° C. for 1 hour. After completion of the reaction, the reaction solution was poured into water, and the mixture was extracted with diethyl ether. The organic layer was washed with diluted hydrochloric acid, dried with magnesium sulfate, and concentrated under reduced pressure to give 1.81 g of 3,3,3-trifluoro-2-oxopropanal 1-[4-chloro-2-fluoro-5-(carboxymethoxy)phenyl hydrazone, compound 3-6 or compound [IV-3] in the above scheme.

$^1$H-NMR (250 MHz, CDCl$_3$, TMS) δ(ppm): 4.77 (s, 2H), 7.25 (d, 1H, J=10.1 Hz), 7.30 (d, 1H, J=6.75 Hz), 7.44 (s, 1H).

Reference Example 6

To a solution of 1.249 g of sodium acetate dissolved in 10 ml of water was added 1.366 g of 1,1-dibromo-3,3,3-trifluoroacetone, and the mixture was stirred at 80° C. for 30 minutes. The reaction solution was left cooling to room temperature, to which a solution of 1.00 g of 4-chloro-2-fluoro-5-(ethoxycarbonyl)methoxyphenylhydrazine dissolved in 10 ml of diethyl ether was added, and the mixture was stirred at room temperature for 2 hours. The reaction solution was extracted with 100 ml of ethyl acetate. The organic layer was washed with 100 ml of saturated aqueous sodium bicarbonate solution and then with 100 ml of saturated aqueous sodium chloride solution, dried with anhydrous magnesium sulfate, and concentrated to give a crude product. The crude product was recrystallized from toluene to give 1.151 g of 3,3,3-trifluoro-2-oxopropanal 1-(4-chloro-2-fluoro-5-(ethoxycarbonyl)methoxyphenylphenylhydrazone), compound 3-8.

$^1$H-NMR (250 MHz, CDCl$_3$, TMS) δ(ppm): 1.32 (t, 3H), 4.29 (q, 2H), 4.71 (s, 2H), 7.06 (d, 1H), 7.20 (d, 1H), 7.36 (m, 1H), 8.77 (brs, 1H).

Reference Example 7

To a solution of 2.870 g of sodium acetate dissolved in 20 ml of water was added 3.139 g of 1,1-dibromo-3,3,3-trifluoroacetone, and the mixture was stirred at 80° C. for 30 minutes. The reaction solution was left cooling to room temperature, to which a solution of 2.000 g of 4-chloro-2-fluoro-5-(1-methyl-2-propynyl)oxyphenylhydrazine dissolved in 10 ml of diethyl ether was added, and the mixture was stirred at room temperature for 2 hours. After completion of the reaction, the reaction solution was extracted with 100 ml of ethyl acetate. The organic layer was washed with 100 ml of saturated aqueous sodium bicarbonate solution and then with 100 ml of saturated aqueous sodium chloride solution, dried with anhydrous magnesium sulfate, and concentrated to give a crude product. The crude product was recrystallized from toluene to give 2.120 g of 3,3,3-trifluoro-2-oxopropanal 1-(4-chloro-2-fluoro-5-(1-methyl-2-propynyl)oxyphenylphenylhydrazone), compound 3-5.

$^1$H-NMR (300 MHz, CDCl$_3$, TMS) δ(ppm): 1.74 (d, 3H), 2.55 (d, 1H), 4.83 (m, 1H), 7.17 (d, 1H), 7.39 (m, 1H), 7.53 (d, 1H), 8.91 (brs, 1H).

Reference Example 8

To a solution of 5.3 g of sodium acetate dissolved in 100 ml of water was added 4.4 g of 1,1-dichloro-3,3,3-trifluoroacetone under ice cooling, and the reaction was allowed to proceed at 90° C. for 30 minutes. The reaction solution was left cooling to room temperature, to which a solution of 5.8 g of 2-fluoro-4-chloro-5-isopropoxyphenylhydrazine dissolved in 20 ml of diethyl ether was added, and the mixture was stirred at room temperature for 1 hour. The organic layer was separated, washed once with 10 ml of saturated aqueous sodium chloride solution, dried with anhydrous magnesium sulfate, and evaporated to remove the diethyl ether to give 6.5 g of 3,3,3-trifluoro-2-oxopropanal 1-(4-chloro-2-fluoro-5-isopropoxyphenylhydrazone), compound 3-3.

The following formulation examples illustrate the use of pyridazin-3-one derivatives of formula (7) as active ingredients of herbicides, in which these derivatives are designated by their compound numbers shown in Table 25 above and "parts" is by weight.

Formulation Example 1

Fifty parts of each of compounds 5-1 to 5-9, 3 parts of calcium lignin-sulfonate, 2 parts of sodium laurylsulfate, and 45 parts of synthetic hydrated silicon oxide are well pulverized and mixed to give a wettable powder for each compound.

Formulation Example 2

Ten parts of each of compounds 5-1 to 5-9, 14 parts of polyoxyethylene styryl phenyl ether, 6 parts of calcium dodecylbenzenesulfonate, 35 parts of xylene, and 35 parts of cyclohexanone are well mixed to give an emulsifiable concentrate for each compound.

Formulation Example 3

Two parts of each of compounds 5-1 to 5-9, 2 parts of synthetic hydrated silicon oxide, 2 parts of calcium ligninsulfonate, 30 parts of bentonite, and 64 parts of kaolin clay are well pulverized and mixed, to which water is added, and the mixture is well kneaded, granulated, and dried to give a granule for each compound.

Formulation Example 4

Twenty-five parts of each of compounds 5-1 to 5-9, 50 parts of 10% aqueous polyvinyl alcohol solution, and 25 parts of water are mixed and the mixture is pulverized until the mean particle size becomes 5 μm or less to give a flowable for each compound.

The following test examples demonstrate that the pyridazin-3-one derivatives of formula (7) are useful as active ingredients of herbicides.

The herbicidal activity was evaluated at 6 levels with indices of 0 to 5, i.e., designated by numeral "0", "1", "2", "3", "4" or "5", wherein "0" means that no or little difference was observed in the degree of germination or growth between the treated and untreated test plants, i.e., unfavorable weeds and crop plants, at the time of examination and "5" means that the treated test plants died complete or their germination or growth was completely inhibited. The herbicidal activity is excellent when rated at "4" or "5" but insufficient when rated at "3" or lower.

Test Example 1 Foliar treatment on upland fields

Cylindrical plastic pots of 10 cm in diameter and 10 cm in depth were filled with soil. The seeds of entireleaf morningglory (*Ipomoea hederacea* var. *integriuscila*) and velvetleaf (*Abutilon theophrasti*) were sowed in the soil, and the test plants were grown in a greenhouse for 19 days. Each of the test compounds listed below was formulated into an emulsifiable concentrate according to Formulation Example 2, which was diluted with water containing a spreading agent to a prescribed concentration. The dilution was uniformly sprayed over the foliage of the test plants with a sprayer at a volume of 1000 liters per hectare. After the application, the test plants were grown in the greenhouse for 19 days, and the herbicidal activity was examined. The results are shown in Table 26.

TABLE 26

| Test compound | Application amount of active ingredient (g/ha) | Herbicidal activity Entireleaf morningglory | Velvetleaf |
|---|---|---|---|
| 5-2 | 500 | 5 | 5 |
| 5-3 | 500 | 5 | 5 |
| 5-6 | 500 | 5 | 5 |

Test Example 2 Soil surface treatment on upland fields

Cylindrical plastic pots of 10 cm in diameter and 10 cm in depth were filled with soil. The seeds of entireleaf morningglory (*Ipomoea hederacea* var. *integriuscula*) and velvetleaf (*Abutilon theophrasti*) were sowed in the soil. Each of the test compounds listed below was formulated into an emulsifiable concentrate according to Formulation Example 2, which was diluted with water to a prescribed concentration. The dilution was uniformly sprayed over the soil surface in the pots with a sprayer at a volume of 1000 liters per hectare. After the application, the test plants were grown in a greenhouse for 19 days, and the herbicidal activity was examined. The results are shown in Table 27.

TABLE 27

| Test compound | Application amount of active ingredient (g/ha) | Herbicidal activity Entireleaf morningglory | Velvetleaf |
|---|---|---|---|
| 5-2 | 500 | 5 | 5 |
| 5-3 | 500 | 5 | 5 |
| 5-6 | 500 | 5 | 5 |

Test Example 3 Flooding treatment on paddy fields

Cylindrical plastic pots of 9 cm in diameter and 11 cm in depth were filled with soil, in which the seeds of barnyardgrass (*Echinochloa oryzicola*) were sowed. These pots were flooded to form a paddy field, and the test plants were grown in a greenhouse for 7 days. Each of the test compounds listed below was formulated into an emulsifiable concentrate according to Formulation Example 2, which was diluted with water to a prescribed concentration. The dilution was applied to the water surface in the pots with a syringe at a volume of 50 liters per are. After the application, the test plants were grown in the greenhouse for 19 days, and the herbicidal activity was examined. The results are shown in Table 28.

TABLE 28

| Test compound | Application amount of active ingredient (g/ha) | Herbicidal activity Barnyardgrass |
|---|---|---|
| 5-2 | 250 | 5 |
| 5-3 | 250 | 5 |
| 5-6 | 250 | 5 |

Industrial Applicability

The carboxylic acids disclosed herein can be easily converted into pyridazin-3-one derivatives and therefore serve as their important intermediates. The process for producing pyridazin-3-one derivatives from these intermediates in a favorable manner makes a great contribution to the development of pyridazine herbicides with excellent activity.

What is claimed is:

1. A process for producing a pyridazin-3-one derivative of formula (7):

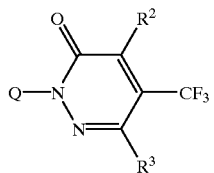

wherein $R^2$ and $R^3$ are independently hydrogen or $C_1$–$C_3$ alkyl, and Q is optionally substituted phenyl comprising ring closing a compound of formula (1) at a temperature of 80° to 250° C., wherein formula (1) is:

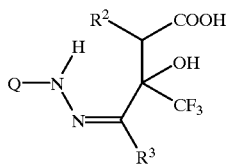

wherein Q is Q-1, Q-2, Q-3, Q-4 or Q-5 of formula (2):

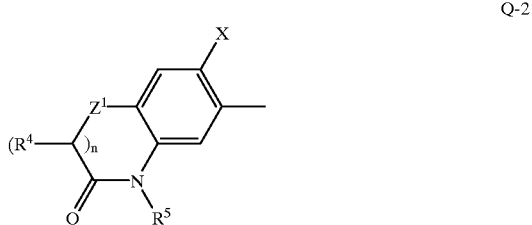

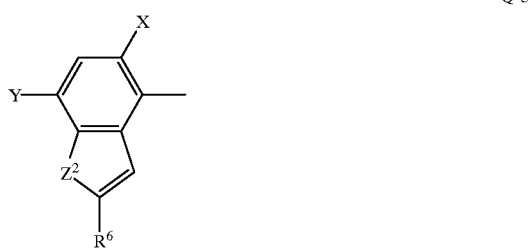

-continued

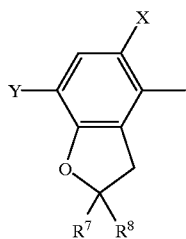

Q-4

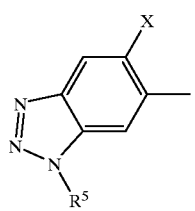

Q-5 wherein

X is hydrogen or halogen;

Y is halogen, nitro, cyano or trifluoromethyl;

$Z^1$ and $Z^2$ are independently oxygen or sulfur;

n is 0 or 1;

$R^4$ is hydrogen or $C_1$–$C_3$ alkyl;

$R^5$ is $C_1$–$C_6$ alkyl, $C_1$–$C_6$ haloalkyl, ($C_3$–$C_6$ cycloalkyl) $C_1$–$C_6$ alkyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_1$–$C_4$ alkoxy $C_1$–$C_4$ alkyl, $C_1$–$C_3$ alkoxy $C_1$–$C_3$ alkoxy alkyl, carboxy $C_1$–$C_6$ alkyl, ($C_1$–$C_6$ alkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, —$CH_2CON(R^{12})R^{13}$, —$CH_2COON(R^{12})R^{13}$, —CH($C_1$–$C_4$ alkyl)CON($R^{12}$)$R^{13}$, —CH($C_1$–$C_4$ alkyl)COON($R^{12}$)$R^{13}$, $C_1$–$C_4$ alkylthio $C_1$–$C_4$ alkyl or hydroxy $C_1$–$C_6$ alkyl;

$R^{12}$ and $R^{13}$ are independently hydrogen, $C_1$–$C_6$ alkyl, $C_3$–$C_8$ cycloalkyl, $C_1$–$C_6$ haloalkyl, $C_3$–$C_6$ alkenyl, $C_3$–$C_6$ alkynyl, cyano $C_1$–$C_6$ alkyl, $C_1$–$C_4$ alkoxy $C_1$–$C_4$ alkyl, $C_1$–$C_4$ alkylthio $C_1$–$C_4$ alkyl, carboxy $C_1$–$C_6$ alkyl, ($C_1$–$C_6$ alkoxy)carbonyl $C_1$–$C_6$ alkyl, ($C_3$–$C_8$ cycloalkoxy)carbonyl $C_1$–$C_6$ alkyl, ($C_1$–$C_6$ alkyl)carbonyloxy $C_2$–$C_6$ alkyl, ($C_1$–$C_6$ alkyl)carbonylamino $C_2$–$C_6$ alkyl, hydroxy $C_2$–$C_6$ alkyl, benzyl, phenyl or {($C_1$–$C_4$ alkoxy) $C_1$–$C_4$ alkyl}carbonyl $C_1$–$C_6$ alkyl, or $R^{12}$ and $R^{13}$ are taken together to form trimethylene, tetramethylene, pentamethylene, ethyleneoxyethylene or ethylenethioethylene;

$R^6$ is $C_1$–$C_6$ alkyl, $C_1$–$C_6$ haloalkyl, cyano, carboxyl, hydroxy $C_1$–$C_6$ alkyl, $C_1$–$C_6$ alkoxy $C_1$–$C_6$ alkyl, $C_1$–$C_6$ alkoxy $C_1$–$C_6$ alkoxy $C_1$–$C_6$ alkyl, ($C_1$–$C_6$ alkyl)carbonyloxy $C_1$–$C_6$ alkyl, ($C_1$–$C_6$ haloalkyl) carbonyloxy $C_1$–$C_6$ alkyl or ($C_1$–$C_6$ alkoxy) carbonyl;

$R^7$ is hydrogen or $C_1$–$C_6$ alkyl;

$R^8$ is $C_1$–$C_6$ alkyl, $C_1$–$C_6$ haloalkyl, hydroxy $C_1$–$C_6$ alkyl, $C_1$–$C_4$ alkoxy $C_1$–$C_4$ alkyl, $C_1$–$C_3$ alkoxy $C_1$–$C_3$ alkoxy $C_1$–$C_3$ alkyl, ($C_1$–$C_6$ alkyl) carbonyloxy $C_1$–$C_6$ alkyl, ($C_1$–$C_6$ haloalkyl) carbonyl $C_1$–$C_6$ alkyl, carboxyl, carboxy $C_1$–$C_6$ alkyl, ($C_1$–$C_8$ alkoxy)carbonyl, ($C_1$–$C_6$ haloalkoxy) carbonyl, ($C_3$–$C_{10}$ cycloalkoxy)carbonyl, ($C_3$–$C_8$ alkenyloxy)carbonyl, ($C_3$–$C_8$ alkynyloxy)carbonyl, ($C_1$–$C_6$ alkyl)aminocarbonyl, di($C_1$–$C_6$ alkyl) aminocarbonyl, ($C_1$–$C_6$ alkyl)aminocarbonyloxy $C_1$–$C_6$ alkyl or di($C_1$–$C_6$ alkyl)aminocarbonyloxy $C_1$–$C_6$ alkyl;

B is hydrogen, halogen, nitro, cyano, chlorosulfonyl, $OR^1$, $SR^1$, $SO_2OR^{21}$, $COOR^{22}$, $CR^{23}$=$CR^{24}COOR^{25}$ or $CH_2CHWCOOR^{25}$;

W is hydrogen, chlorine or bromine;

$R^1$ is hydrogen, $C_1$–$C_6$ alkyl, $C_1$–$C_6$ haloalkyl, $C_3$–$C_8$ cycloalkyl, benzyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_1$–$C_4$ alkoxy $C_1$–$C_4$ alkyl, $C_1$–$C_4$ alkylthio $C_1$–$C_4$alkyl, carboxy $C_1$–$C_6$ alkyl, ($C_1$–$C_8$ alkoxy)carbonyl $C_1$–$C_6$ alkyl, ($C_1$–$C_6$ haloalkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, ($C_3$–$C_8$ cycloalkyl) $C_1$–$C_6$ alkoxycarbonyl $C_1$–$C_6$ alkyl, —$CH_2COON(R^{12})R^{13}$, —CH—($C_1$–$C_4$ akyl) COON($R^{12}$)$R^{13}$, —$CH_2CON(R^{12})R^{13}$, —CH ($C_1$–$C_4$ alkyl)CON($R^{12}$)$R^{13}$, $C_2$–$C_6$ alkenyloxycarbonyl $C_1$–$C_6$ alkyl, $C_3$–$C_6$ haloalkenyloxycarbonyl $C_1$–$C_6$ alkyl, $C_3$–$C_6$ alkynyloxycarbonyl $C_1$–$C_6$ alkyl, $C_3$–$C_6$ haloalkynyloxycarbonyl $C_1$–$C_6$ alkyl, ($C_1$–$C_6$ alkylthio)carbonyl $C_1$–$C_6$ alkyl, ($C_1$–$C_6$ haloalkylthio)carbonyl $C_1$–$C_6$ alkyl, ($C_3$–$C_6$ alkenylthio)carbonyl $C_1$–$C_6$ alkyl, ($C_3$–$C_6$ haloalkenylthio)carbonyl $C_1$–$C_6$ alkyl, ($C_3$–$C_6$ alkynylthio)carbonyl $C_1$–$C_6$ alkyl, ($C_3$–$C_6$ haloalkynylthio)carbonyl $C_1$–$C_6$ alkyl, ($C_3$–$C_8$ cycloalkylthio)carbonyl $C_1$–$C_6$ alkyl, ($C_3$–$C_8$ cyclohaloalkylthio)carbonyl $C_1$–$C_6$ alkyl, (($C_3$–$C_8$ cycloalkyl) $C_1$–$C_6$ alkylthio)carbonyl $C_1$–$C_6$ alkyl, di($C_1$–$C_6$ alkyl)C=NO carbonyl $C_1$–$C_6$ alkyl, (optionally substituted benzylthio)carbonyl $C_1$–$C_6$ alkyl, (optionally substituted phenylthio)carbonyl $C_1$–$C_6$ alkyl, hydroxy $C_2$–$C_6$ alkoxycarbonyl $C_1$–$C_6$ alkyl, ($C_1$–$C_6$ alkyl)carbonyloxy $C_2$–$C_6$ alkoxycarbonyl $C_1$–$C_6$ alkyl, ($C_1$–$C_6$ alkyl)carbonylamino $C_2$–$C_6$ alkoxycarbonyl $C_1$–$_6$ alkyl, {($C_1$–$C_6$ alkoxy) carbonyl $C_1$–$C_6$ alkyl}oxycarbonyl $C_1$–$C_6$ alkyl, hydroxy $C_1$–$C_6$ alkyl, $C_1$–$C_6$ alkoxycarbonyl, $C_1$–$C_6$ haloalkoxycarbonyl, $C_3$–$C_8$ cycloalkoxycarbonyl, $C_3$–$C_3$ alkenyloxycarbonyl, benzyloxycarbonyl, $C_1$–$C_6$ alkylcarbonyl, benzyloxycarbonyl $C_1$–$C_6$ alkyl, phenoxycarbonyl $C_1$–$C_6$ alkyl, furyloxycarbonyl $C_1$–$C_6$ alkyl, furyl $C_1$–$C_6$ alkyloxycarbonyl $C_1$–$C_6$ alkyl, thienyloxycarbonyl $C_1$–$C_6$ alkyl, thienyl $C_1$–$C_6$ alkyloxycarbonyl $C_1$–$C_6$ alkyl, pyrrolyloxycarbonyl $C_1$–$C_6$ alkyl, pyrrolyl $C_1$–$C_6$ alkyloxycarbonyl $C_1$–$C_6$ alkyl, imidazoloxycarbonyl $C_1$–$C_6$ alkyl, imidazoyl $C_1$–$C_6$ alkyloxycarbonyl $C_1$–$C_6$ alkyl, pyrazoyloxycarbonyl $C_1$–$C_6$ alkyl, pyrazoyl $C_1$–$C_6$ alkyloxycarbonyl $C_1$–$C_6$ alkyl, thiazoyloxycarbonyl $C_1$–$C_6$ alkyl, thiazoyl $C_1$–$C_6$ alkyloxycarbonyl $C_1$–$C_6$ alkyl, oxazoyloxycarbonyl $C_1$–$C_6$ alkyl, oxazoyl $C_1$–$C_6$ alkyloxycarbonyl $C_1$–$C_6$ alkyl, isothiazoyloxycarbonyl $C_1$–$C_6$ alkyl, isothiazoyl $C_1$–$C_6$ alkyloxycarbonyl $C_1$–$C_6$ alkyl, isoxazoyloxycarbonyl $C_1$–$C_6$ alkyl, isoxazoyl $C_1$–$C_6$ alkyloxycarbonyl $C_1$–$C_6$ alkyl, pyridyloxycarbonyl $C_1$–$C_6$ alkyl, pyridyl $C_1$–$C_6$ alkyloxycarbonyl $C_1$–$C_6$ alkyl, pyrazinyloxycarbonyl $C_1$–$C_6$ alkyl, pyrazinyl $C_1$–$C_6$ alkyloxycarbonyl $C_1$–$C_6$ alkyl, pyrimidinyloxycarbonyl $C_1$–$C_6$ alkyl, pyrimidinyl $C_1$–$C_6$ alkyloxycarbonyl $C_1$–$C_6$ alkyl, pyridazinyloxycarbonyl $C_1$–$C_6$ alkyl, pyridazinyl $C_1$–$C_6$ alkyloxycarbonyl $C_1$–$C_6$ alkyl, indolidinyloxycarbonyl $C_1$–$C_6$ alkyl, indolidinyl $C_1$–$C_6$ alkyloxycarbonyl $C_1$–$C_6$ alkyl, indolyloxycarbonyl $C_1$–$C_6$ alkyl, indolyl $C_1$–$C_6$ alkyloxycarbonyl $C_1$–$C_6$ alkyl, indazolyloxycarbonyl $C_1$–$C_6$ alkyl, indazolyl $C_1$–$C_6$ alkyloxycarbonyl $C_1$–$C_6$ alkyl, quinolyloxycarbonyl $C_1$–$C_6$ alkyl, quinolyl $C_1$–$C_6$ alkyloxycarbonyl $C_1$–$C_6$ alkyl, isoquinolyloxycarbonyl $C_1$–$C_6$ alkyl, isoquinolyl $C_1$–$C_6$ alkyloxycarbonyl $C_1$–$C_6$ alkyl, or a group of formula (3):

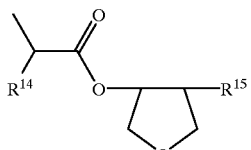

wherein $R^{14}$ is $C_1$–$C_5$ alkyl; $R^{15}$ is hydrogen, hydroxyl or a group of —O—$COR^{16}$; $R^{16}$ is $C_1$–$C_6$ alkyl, $C_1$–$C_6$ haloalkyl, $C_3$–$C_6$ alkenyl, $C_3$–$C_8$ cycloalkyl, phenyl, [optionally substituted] benzyl or $C_1$–$C_6$ alkoxy, or a group of formula (4):

wherein $R^{17}$ is hydrogen, halogen or $C_1$–$C_6$ alkyl; $R^{18}$ is $C_3$–$C_8$ cycloalkyl, benzyl, $C_2$–$C_{10}$ alkyl with an epoxide group, $C_3$–$C_8$ cycloalkyl $C_1$–$C_6$ alkyl, $C_3$–$C_8$ cycloalkyl $C_2$–$C_6$ alkenyl, $C_1$–$C_6$ alkyl substituted with $OR^{19}$ and $OR^{20}$ on the same carbon atom, $C_2$–$C_6$ alkenyl substituted with $OR^{19}$ and $OR^{20}$ on the same carbon atom, $C_1$–$C_6$ alkyl substituted with $SR^{19}$ and $SR^{20}$ on the same carbon atom, $C_2$–$C_6$ alkenyl substituted with $SR^{19}$ and $SR^{20}$ on the same carbon atom, carboxy $C_2$–$C_6$ alkenyl, ($C_1$–$C_8$ alkoxy)carbonyl $C_2$–$C_6$ alkenyl, ($C_1$–$C_8$ haloalkoxy)carbonyl $C_2$–$C_6$ alkenyl, {($C_1$–$C_4$ alkoxy) $C_1$–$C_4$ alkoxy}carbonyl $C_2$–$C_6$ alkenyl or ($C_3$–$C_8$ cycloalkoxy)carbonyl $C_2$–$C_6$ alkenyl; $R^{19}$ and $R^{20}$ are independently $C_1$–$C_6$ alkyl or $C_1$–$C_6$ haloalkyl, or $R^{19}$ and $R^{20}$ are taken together with to form ethylene optionally substituted with halogen, trimethylene optionally substituted with halogen, tetramethylene optionally substituted with halogen, pentamethylene optionally substituted with halogen, or ethyleneoxyethylene optionally substituted with halogen;

$R^{21}$ is $C_1$–$C_6$ alkyl, $C_1$–$C_6$ haloalkyl, $C_3$–$C_8$ cycloalkyl, $C_3$–$C_6$ alkenyl, $C_3$–$C_6$ haloalkenyl, $C_3$–$C_6$ alkynyl, $C_3$–$C_6$ haloalkynyl or benzyl;

$R^{22}$ is hydrogen, $C_1$–$C_6$ alkyl, $C_1$–$C_6$ haloalkyl, $C_3$–$C_8$ cycloalkyl, benzyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_1$–$C_4$ alkoxy $C_1$–$C_4$ alkyl, $C_1$–$C_4$ alkylthio $C_1$–$C_4$ alkyl, carboxy $C_1$–$C_6$ alkyl, ($C_1$–$C_8$ alkoxy)carbonyl $C_1$–$C_6$ alkyl, ($C_1$–$C_6$ haloalkoxy)carbonyl $C_1$–$C_6$ alkyl, {($C_1$–$C_6$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, ($C_1$–$C_6$ alkyl)carbonyl $C_1$–$C_6$ alkyl, ($C_1$–$C_6$ haloalkyl)carbonyl $C_1$–$C_6$ alkyl, {($C_1$–$C_4$ alkoxy) $C_1$–$C_4$ alkyl}carbonyl $C_1$–$C_6$ alkyl, ($C_3$–$C_8$ cycloalkyl)carbonyl $C_1$–$C_6$ alkyl, —$CH_2COON(R^{26})R^{27}$, —$CH(C_1$–$C_4$alkyl) COON $(R^{26})R^{27}$, —$CH_2CON(R^{26})R^{27}$, —CH—($C_1$–$C_4$ alkyl)$CON(R^{26})R^{27}$, {($C_1$–$C_6$ alkoxy) carbonyl $C_1$–$C_6$ alkyl}oxycarbonyl $C_1$–$C_6$ alkyl or hydroxy $C_1$–$C_6$ alkyl;

$R^{26}$ and $R^{27}$ are independently hydrogen, $C_1$–$C_6$ alkyl, $C_1$–$C_6$ haloalkyl, $C_3$–$C_6$ alkenyl, $C_3$–$C_6$ alkynyl, cyano $C_1$–$C_6$ alkyl, $C_1$–$C_4$ alkoxy $C_1$–$C_4$ alkyl, $C_1$–$C_4$ alkylthio $C_1$–$C_4$ alkyl, carboxy $C_1$–$C_6$ alkyl, ($C_1$–$C_6$ alkoxy)carbonyl $C_1$–$C_6$ alkyl, ($C_3$–$C_8$ cycloalkoxy)carbonyl $C_1$–$C_6$ alkyl or {($C_1$–$C_4$ alkoxy) $C_1$–$C_4$ alkyl}carbonyl $C_1$–$C_6$ alkyl, or $R^{26}$ and $R^{27}$ are taken together to form tetramethylene, pentamethylene or ethyleneoxyethylene;

$R^{23}$ and $R^{24}$ are independently hydrogen, halogen or $C_1$–$C_6$ alkyl; and $R^{25}$ is hydrogen, $C_1$–$C_6$ alkyl, $C_1$–$C_6$ haloalkyl, $C_3$–$C_8$ cycloalkyl or $C_3$–$C_6$ alkenyl.

2. The process according to claim 1 for producing a pyridazin-3-one derivative of formula (7), comprising ring closing a compound of formula (1) in the presence of a base.

3. The process according to claim 1 for producing a pyridazin-3-one derivative of formula (7), comprising ring closing a compound of formula (1) in the presence of an acid.

4. The process according to claim 1 for producing a pyridazin-3-one derivative of formula (7), comprising ring closing a compound of formula (1) in the presence of an acid and base.

5. The process according to claim 1 for producing a pyridazin-3-one derivative of formula (7), comprising ring closing a compound of formula (1) in the presence of a haloformic acid alkyl ester and a base.

* * * * *